United States Patent
Jaffrey et al.

(10) Patent No.: US 11,685,923 B2
(45) Date of Patent: Jun. 27, 2023

(54) METHODS OF ENHANCING TRANSLATION ABILITY OF RNA MOLECULES, TREATMENTS, AND KITS

(71) Applicant: CORNELL UNIVERSITY, Ithaca, NY (US)

(72) Inventors: Samie R. Jaffrey, New York, NY (US); Kate D. Meyer, Durham, NC (US)

(73) Assignee: CORNELL UNIVERSITY, Ithaca, NY (US)

( * ) Notice: Subject to any disclaimer, the term of this patent is extended or adjusted under 35 U.S.C. 154(b) by 223 days.

(21) Appl. No.: 16/795,216

(22) Filed: Feb. 19, 2020

(65) Prior Publication Data

US 2020/0199601 A1 Jun. 25, 2020

Related U.S. Application Data

(62) Division of application No. 15/744,246, filed as application No. PCT/US2016/042550 on Jul. 15, 2016, now Pat. No. 10,584,343.

(60) Provisional application No. 62/193,464, filed on Jul. 16, 2015.

(51) Int. Cl.
  *C12N 15/67* (2006.01)
  *C12P 21/02* (2006.01)
  *C12P 19/34* (2006.01)

(52) U.S. Cl.
  CPC .............. *C12N 15/67* (2013.01); *C12P 19/34* (2013.01); *C12P 21/02* (2013.01); *C12N 2310/333* (2013.01); *C12N 2740/16043* (2013.01)

(58) Field of Classification Search
  None
  See application file for complete search history.

(56) References Cited

U.S. PATENT DOCUMENTS

| | | |
|---|---|---|
| 8,604,183 B2 | 12/2013 | Mlerson et al. |
| 10,584,343 B2 | 3/2020 | Jaffrey et al. |

| | | |
|---|---|---|
| 2012/0046346 A1 | 2/2012 | Rossi et al. |
| 2015/0064236 A1 | 3/2015 | Bancel et al. |
| 2016/0264934 A1 | 9/2016 | Giallourakis et al. |
| 2017/0043037 A1 | 2/2017 | Kariko et al. |
| 2018/0195077 A1 | 7/2018 | Jaffrey et al. |

FOREIGN PATENT DOCUMENTS

| | | |
|---|---|---|
| WO | 2013/123481 A1 | 8/2013 |
| WO | 2014/093924 A1 | 6/2014 |

OTHER PUBLICATIONS

Dominissini etal., "Topology of the Human and Mouse m6A RNA Methylomes Revealed by m6A-seq," Nature 485(7397):201-206 (2012).
Li et al., "Transcriptome-wide N6-methyladenosine Profiling of Rice Callus and Leaf Reveals the Presence of Tissue-specific competitors Involved in Selective mRNA Modification," RNA Biology 11(9):1180-1188 (2014).
Meyer et al., "The Dynamic Epitranscriptome: N6-methyladenosine and Gene Expression Control," Nature Reviews Molecular Cell Biology 15(5):313-326 (2014).
Schwartz et al., "Perturbation of m6A Writers Reveals Two Distinct Classes of mRNA Methylation at Internal and 5' Sites," Cell Reports 8(1):284-296 (2014).
PCT International Search Report and Written Opinion corresponding to PCT/US2016/042550, dated Nov. 4, 2016.
Costello et al., "Improved Yield of rhEPO in CHO Cells With Synthetic 5' UTR," Biotechnol Lett. 41(2):231-239 (2019).
Meyer et al., "5' UTR m(6)A Promotes Cap-Independent Translation," Cell 163(4):999-1010 (2015).
Shikawa et al., "Preparation of Eukaryotic mRNA Having Differently Methylated Adenosine at the 5'-terminus and the Effect of the Methyl Group in Translation," Nucleic Acids Symposium Series No. 53:129-130 (2009).

*Primary Examiner* — Sean McGarry
(74) *Attorney, Agent, or Firm* — Troutman Pepper Hamilton Sanders LLP (Rochester)

(57) ABSTRACT

The present invention relates to methods and a kit for enhancing the translation ability of an RNA molecule. The methods involve the use of an RNA molecule comprising a methylated adenosine residue in a 5' untranslated region (UTR). Also disclosed are methods for eIF4E-independent translation of an RNA molecule and treatment methods.

16 Claims, 24 Drawing Sheets

Specification includes a Sequence Listing.

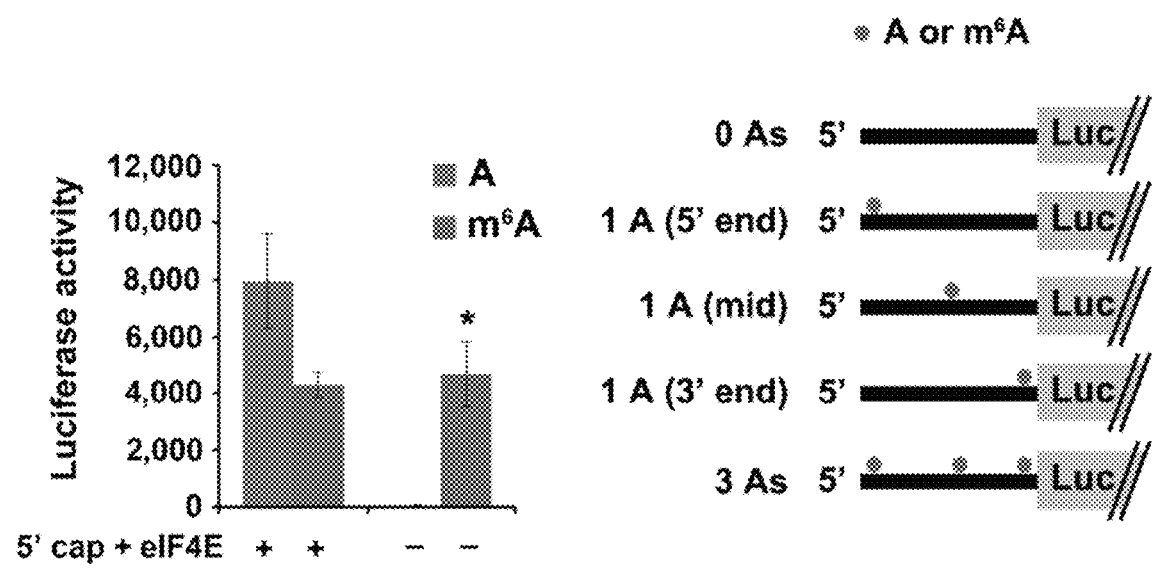
*FIG. 3C*
*FIG. 3D*
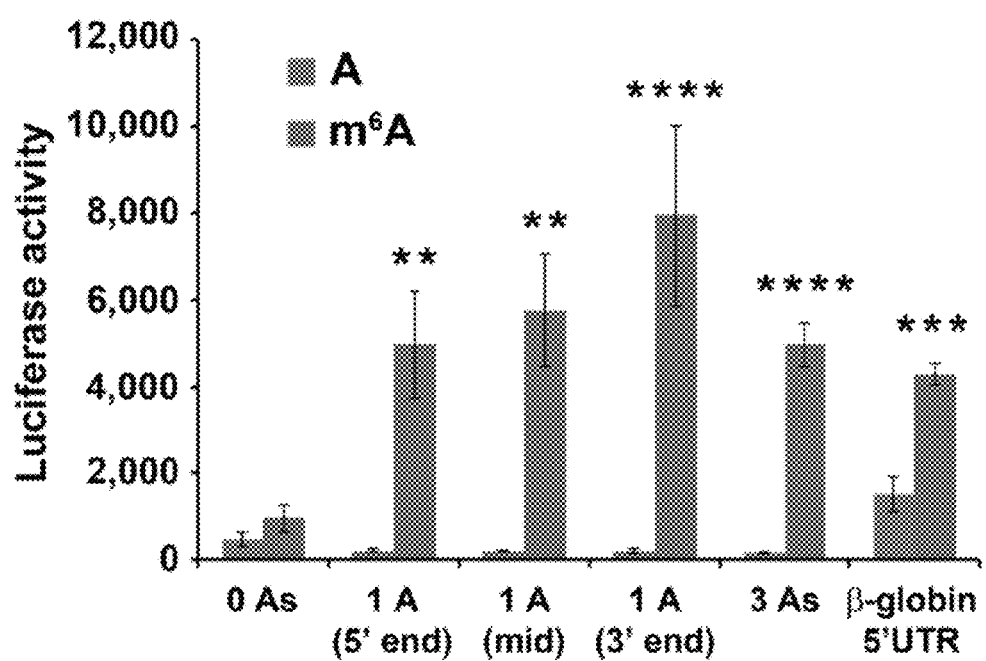
*FIG. 3D (Cont.)*

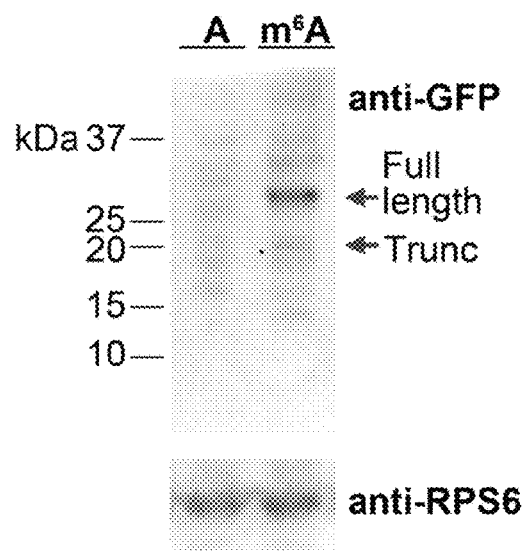
*FIG. 4B*
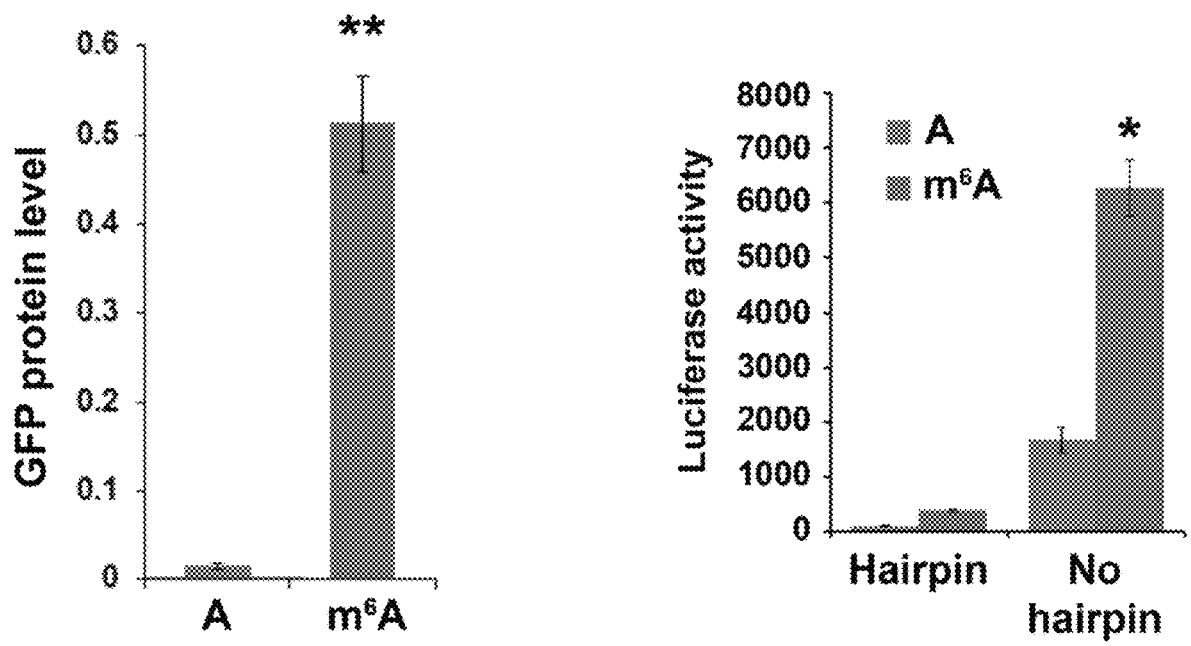
*FIG. 4C*

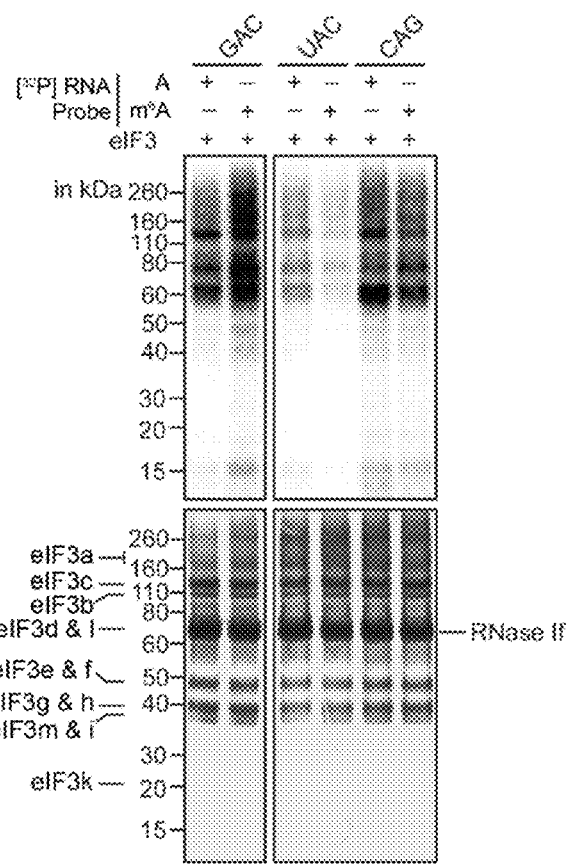
*FIG. 6E*
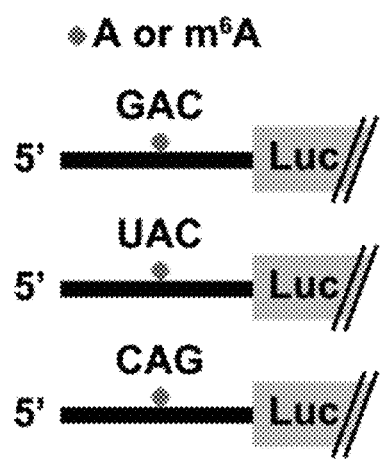
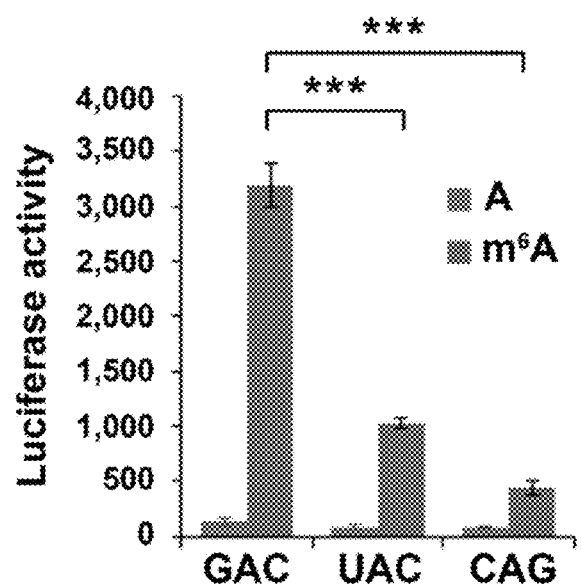
*FIG. 6F*

| Accession | Description | MW [kDa] | # Peptides |
|---|---|---|---|
| EIF3D_HUMAN | Eukaryotic translation initiation factor 3 subunit D | 63.9 | 75 |
| EIF3I_HUMAN | Eukaryotic translation initiation factor 3 subunit I | 36.5 | 42 |
| EIF3M_HUMAN | Eukaryotic translation initiation factor 3 subunit M | 42.5 | 28 |
| EIF3E_HUMAN | Eukaryotic translation initiation factor 3 subunit E | 52.2 | 54 |
| EIF3H_HUMAN | Eukaryotic translation initiation factor 3 subunit H | 39.9 | 36 |
| EIF3K_HUMAN | Eukaryotic translation initiation factor 3 subunit K | 25.0 | 23 |
| EIF3G_HUMAN | Eukaryotic translation initiation factor 3 subunit G | 35.6 | 31 |
| EIF3L_HUMAN | Eukaryotic translation initiation factor 3 subunit L | 66.7 | 37 |
| EIF3F_HUMAN | Eukaryotic translation initiation factor 3 subunit F | 37.5 | 22 |
| EIF3C_HUMAN | Eukaryotic translation initiation factor 3 subunit C | 105.3 | 13 |
| IF4A2_HUMAN | Eukaryotic initiation factor 4A-II | 46.4 | 6 |
| EIF3B_HUMAN | Eukaryotic translation initiation factor 3 subunit B | 92.4 | 4 |
| ELP3_HUMAN | Elongator complex protein 3 | 62.2 | 2 |
| ATLA2_HUMAN | Atlastin-2 | 66.2 | 2 |
| IF4G1_HUMAN | Eukaryotic translation initiation factor 4 gamma 1 | 175.4 | 1 |

*FIG. 7C*

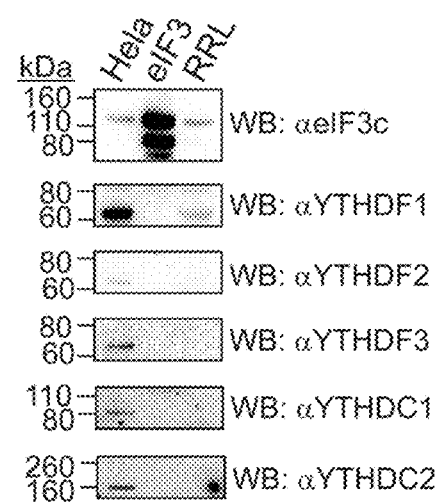

*FIG. 7D*

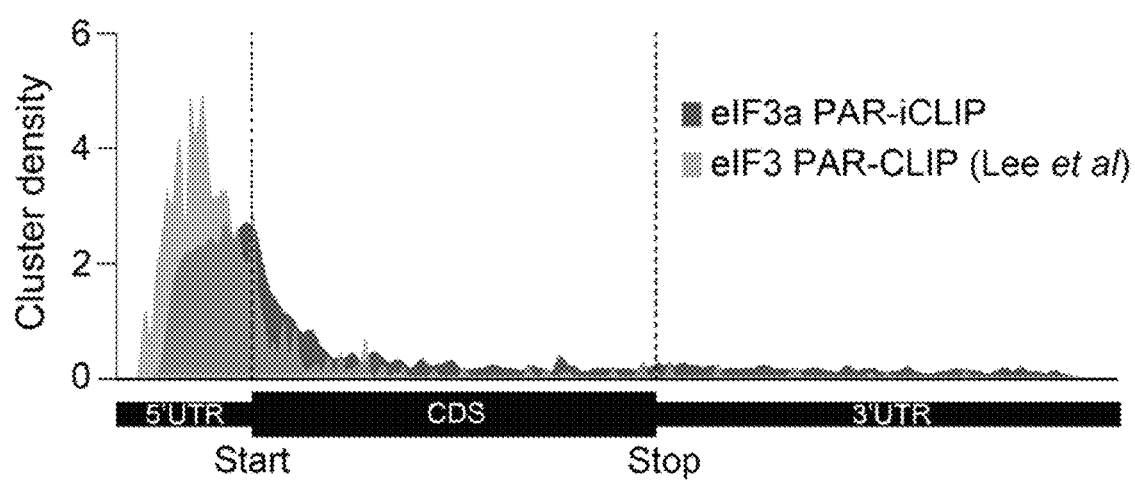

| Window size | % overlap | % overlap expected by chance | p-value |
|---|---|---|---|
| 25 nt | 35% | 25% | p<0.01 |
| 20 nt | 31.4% | 21% | p<0.01 |
| 10 nt | 29.5% | 19.5% | p<0.01 |

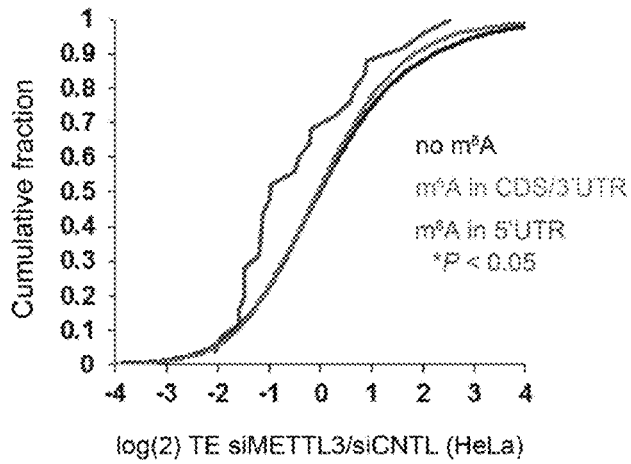
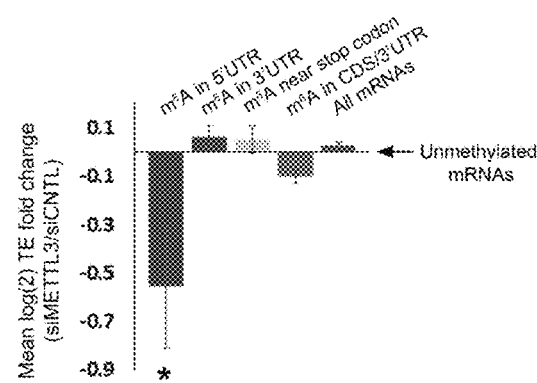
FIG. 10A    FIG. 10B
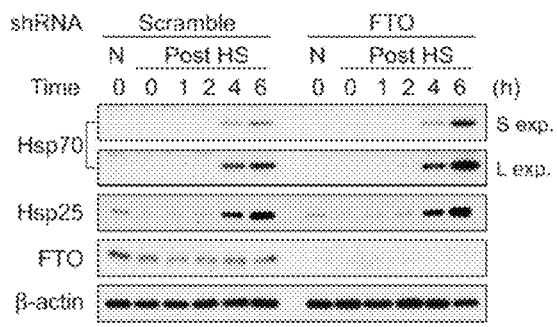
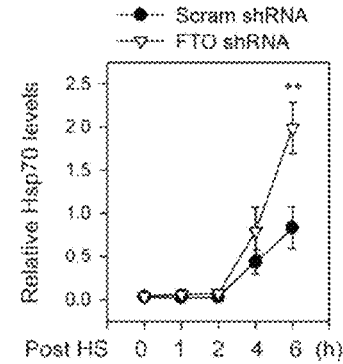
FIG. 10C
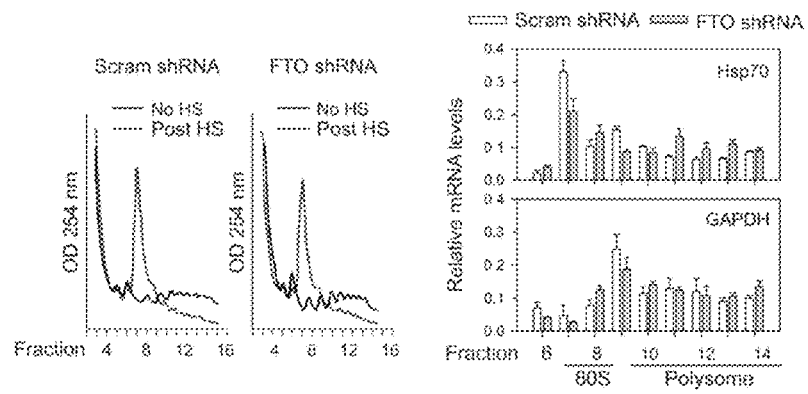
FIG. 10D

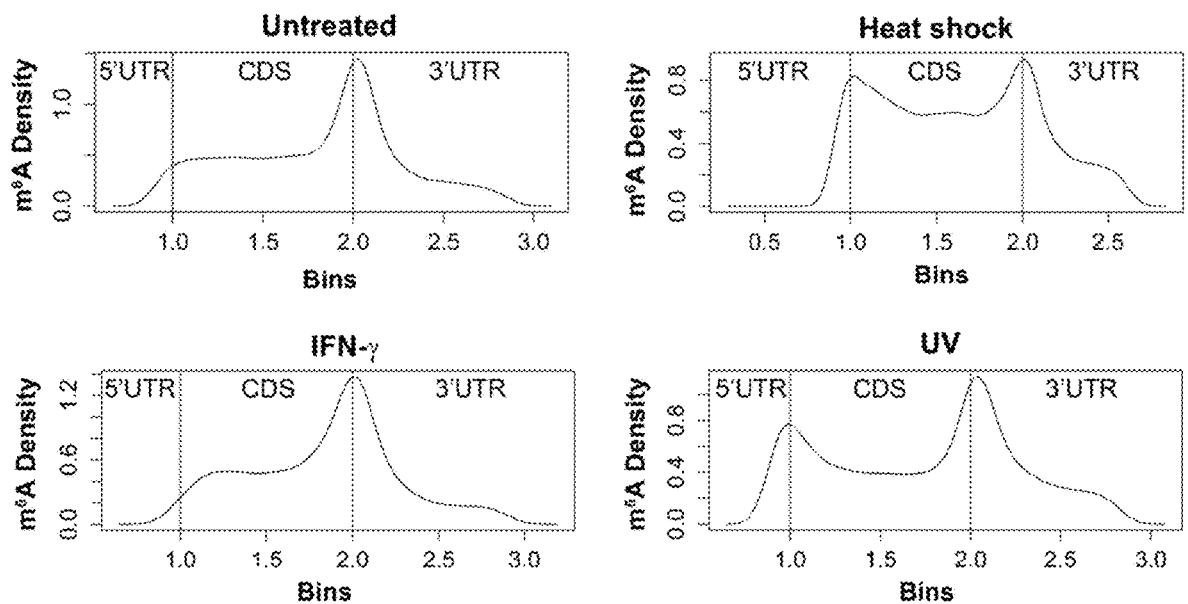
*FIG. 12D*
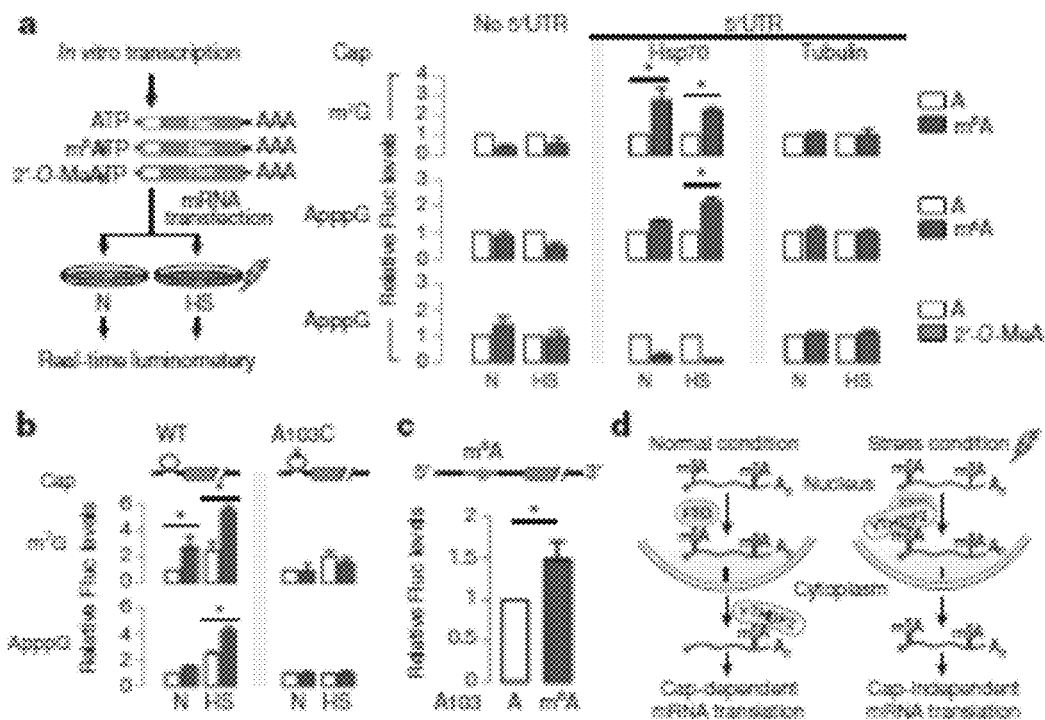
*FIGS. 13A-D*

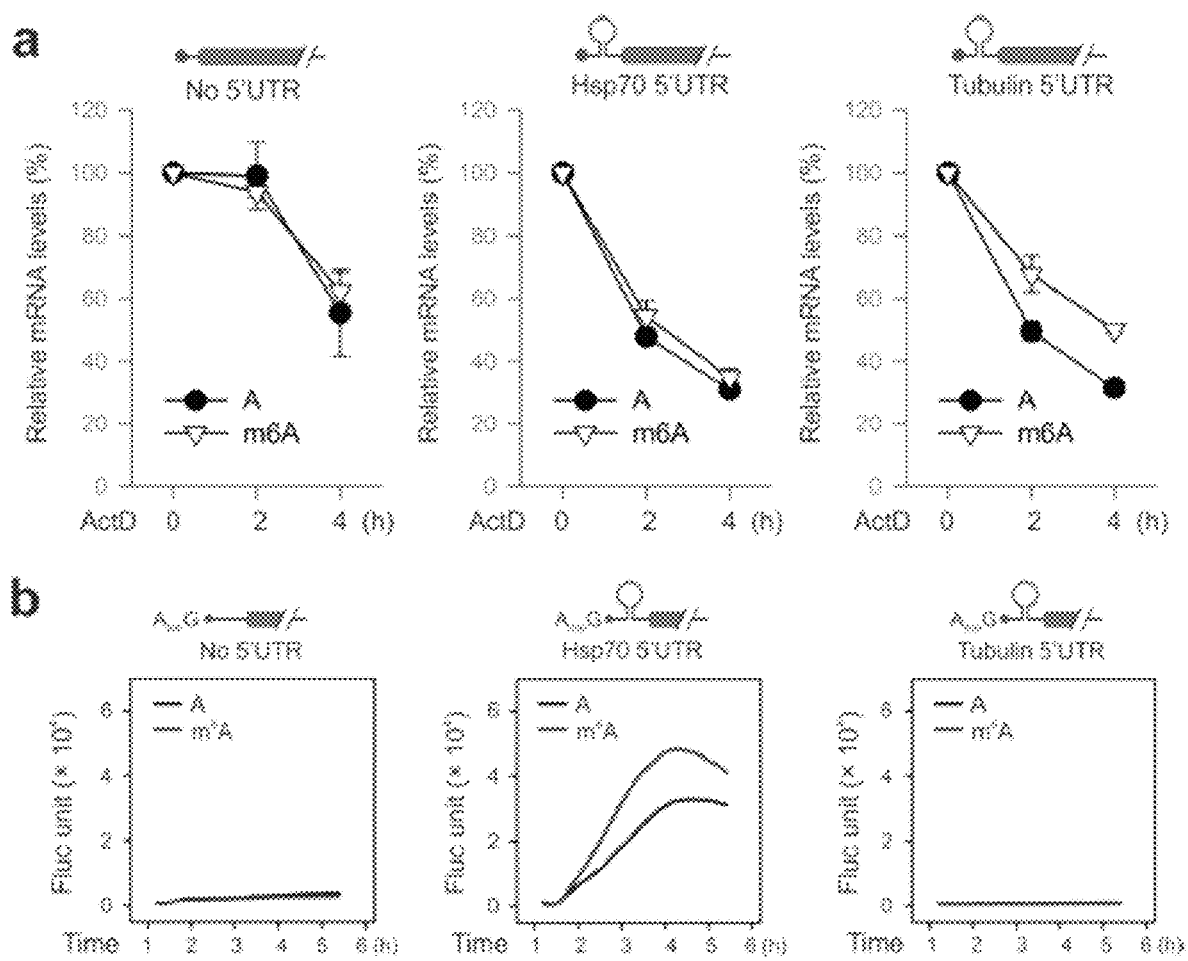
FIGS. 14A-B

FIGS. 15A-B

METHODS OF ENHANCING TRANSLATION ABILITY OF RNA MOLECULES, TREATMENTS, AND KITS

This application is a division of U.S. patent application Ser. No. 15/744,246, filed Jan. 12, 2018, which is a national stage application under 35 U.S.C. § 371 from PCT Application No. PCT/US2016/042550, filed Jul. 15, 2016, which claims the priority benefit of U.S. Provisional Patent Application Ser. No. 62/193,464, filed Jul. 16, 2015, which are hereby incorporated by reference in their entirety.

This invention was made with government support under Grant Nos. MH104712 and CA186702-02 awarded by the National Institutes of Health. The government has certain rights in the invention.

FIELD OF THE INVENTION

This invention relates to methods of enhancing the translation ability of RNA molecules, treatments, and a kit.

BACKGROUND OF THE INVENTION

Protein translation typically begins with the recruitment of the 43S ribosomal complex to the 5' cap of mRNAs by a cap-binding complex. However, some transcripts are translated in a cap-independent manner through poorly understood mechanisms. For most cellular mRNAs, the first step of mRNA translation involves recognition of the 5' 7-methylguanosine ($m^7G$) cap by eukaryotic initiation factor 4E (eIF4E), which is a subunit of the heterotrimeric eIF4F complex. 5' cap-bound eIF4F then recruits the small (40S) ribosomal subunit associated with various translation initiation factors, enabling efficient translation of eukaryotic mRNAs.

However, some mRNAs are translated in a cap-independent manner. These capped mRNAs do not require eIF4E and are translated under basal cellular conditions as well as conditions where eIF4E activity is compromised, such as cellular stress states, viral infection, and in diseases such as cancer (Stoneley et al., "Cellular Internal Ribosome Entry Segments: Structures, Trans-Acting Factors and Regulation Of Gene Expression," *Oncogene* 23:3200-3207 (2004)). Although viral mRNAs can exhibit cap-independent translation due to the presence of highly structured internal ribosome entry site ("IRES") motifs in the 5' UTR, correspondingly complex structures are rarely found in eukaryotic mRNAs undergoing cap-independent translation (Stoneley et al., "Cellular Internal Ribosome Entry Segments: Structures, Trans-Acting Factors and Regulation Of Gene Expression," *Oncogene* 23:3200-3207 (2004)). Thus, the mechanism of cap-independent translation in cellular mRNAs remains poorly understood.

A feature of many eukaryotic mRNAs is $N^6$-methyladenosine ("$m^6A$"), a reversible base modification seen in the 3' UTR coding sequence, and 5' UTR (Dominissini et al., "Topology of the Human and Mouse m6A RNA Methylomes Revealed by m6A-Seq.," *Nature* 485:201-206 (2012); Meyer et al., "Comprehensive Analysis of mRNA Methylation Reveals Enrichment in 3' UTRs and Near Stop Codons," *Cell* 149:1635-1646 (2012). Although the function of $m^6A$ in the coding sequence and 3' UTRs has been explored (Wang et al., "N6-Methyladenosine-Dependent Regulation of Messenger RNA Stability," *Nature* 505:117-120 (2014a); Wang et al., "N(6)-Methyladenosine Modulates Messenger RNA Translation Efficiency," *Cell* 161: 1388-1399 (2015); Wang et al., "N(6)-Methyladenosine Modification Destabilizes Developmental Regulators in Embryonic Stem Cells," *Nat. Cell Biol.* 16:191-198 (2014b)), the function of $m^6A$ in 5' UTRs remains unknown.

The present invention is directed to overcoming these and other deficiencies in the art.

SUMMARY OF THE INVENTION

One aspect of the present invention relates to a method of enhancing the translation ability of an RNA molecule. This method involves providing a cell-free composition comprising an RNA molecule to be translated, where the RNA molecule lacks a methylated adenosine residues in a 5' untranslated region (UTR) and introducing a methylated adenosine residue in a 5' untranslated region (UTR) of the RNA molecule, where said introducing enhances translation ability of the RNA molecule relative to the RNA molecule lacking a methylated adenosine residue in the 5' untranslated region (UTR).

Another aspect of the present invention relates to a method for eIF4E-independent translation of an RNA molecule. This method involves providing an RNA molecule to be translated, where the RNA molecule comprises a methylated adenosine residue in a 5' untranslated region (UTR) and a heterologous 5' cap and translating the RNA molecule.

A further aspect of the present invention relates to a treatment method. This method involves contacting a cell with an RNA molecule comprising a methylated adenosine residue in a 5' untranslated region (UTR) under conditions effective to effect translation of the RNA molecule to treat the cell.

Another aspect of the present invention relates to a treatment method. This method involves contacting a cell with a DNA molecule encoding an RNA molecule comprising an adenosine methylation motif in a 5' untranslated region (UTR) under conditions effective for the DNA molecule to be transcribed to produce an RNA molecule comprising an adenosine methylation motif in a 5' untranslated region (UTR) such that the RNA molecule is methylated at the adenosine methylation motif and is translated to treat the cell.

A further aspect of the present invention relates to a treatment method. This method involves contacting a cell with an agent capable of recruiting methylation machinery to an RNA molecule comprising an adenosine residue in a 5' untranslated region (UTR) under conditions effective to methylate the adenosine residue such that the RNA molecule is translated to treat the cell.

Another aspect of the present invention relates to a method of enhancing translation ability of an RNA molecule in a cell. This method involves identifying a cell comprising an RNA molecule that could benefit from eIF4E-independent translation and contacting the cell with an agent capable of forming a methylated adenosine residue in a 5' untranslated region (UTR) of the RNA molecule to enhance translation ability of the RNA molecule in the cell.

A further aspect of the present invention relates to a kit. The kit includes a DNA molecule encoding an RNA molecule comprising an adenosine methylation motif in a 5' untranslated region (UTR); reagents for transcribing the RNA molecule; and reagents for methylating the RNA molecule.

Another aspect of the present invention relates to an mRNA molecule comprising a methylated adenosine residue in a 5' untranslated region (UTR) and a 5' cap.

The present application shows that $m^6A$ in the 5' UTR functions as an alternative to the 5' cap to stimulate mRNA translation. Using both in vitro reconstitution approaches and translation assays in cellular lysates deficient in eIF4E activity, a unique translation initiation mechanism that does not require the 5' cap is defined. Applicants show the m$^6$A in the 5' UTR can recruit eukaryotic initiation factor 3 ("eIF3"). Transcriptome-wide ribosome profiling analysis indicates that the translation of 5' UTR m$^6$A-containing mRNAs is reduced upon depletion of the m$^6$A methyltransferase, METTL3, while mRNAs containing m$^6$A elsewhere within the transcript fail to show this effect. The importance of 5' UTR m$^6$A residues for cellular mRNA translation is demonstrated by both ribosome profiling analysis and detection of changes to global m$^6$A distribution in 5' UTRs in response to cellular stress. Thus, 5' UTR m$^6$A residues are linked to cellular stress states and provide a mechanism to bypass the m$^7$G cap requirement for mRNA translation, enabling a cap-independent mode of translation initiation.

BRIEF DESCRIPTION OF THE DRAWINGS

FIG. 1B shows that eIFs1, 1A, and 3 are required for efficient m$^6$A-induced cap-independent 48S complex formation. Toe-printing assays were performed (as in FIG. 1A) using A- or m$^6$A-containing mRNAs and in the presence of various translation initiation components as indicated. m$^6$A-containing mRNA exhibits robust 48S complex assembly in the absence of eIF4F, whereas A-containing mRNA does not (compare lanes 1 and 7). Efficient m$^6$A-mediated 48S complex assembly is also dependent on the presence of eIFs1 and 1A, which is consistent with the known roles of these proteins in promoting scanning and AUG recognition (compare lanes 1 with lanes 2, 4, and 5). Removal of eIF3 also abolishes 48S complex assembly on m$^6$A-containing mRNA (compare lanes 1 and 2), indicating that eIF3 is required for m$^6$A-mediated 48S complex formation. Addition of 60S subunits, eIF5, eIF5B, eEF1H, eEF2 and aa-tRNAs resulted in the appearance of toe-prints corresponding to pre-termination complexes at the stop codon, indicating that m$^6$A-recruited 48S complexes are fully functional (lane 6). FIG. 1C shows that omission of eIF2 from toe-printing assays results in the absence of 48S complexes (compare lanes 2 and 3), indicating that eIF2 is required for 48S complex assembly on m$^6$A-containing mRNA.

FIG. 2A is a western blot of HeLa cell extracts. The HeLa extract system is known to be deficient in eIF4E activity, and exogenous eIF4E is needed to enhance translation of capped mRNAs. Here, applicants asked whether the requirement for exogenous eIF4E reflects the presence of inactive eIF4E or the absence of eIF4E in this preparation. Western blotting for eIF4E on the HeLa cell lysates used for in vitro translation assays as well as rabbit reticulocyte lysates (RRL) reveals that levels of eIF4E are present, albeit reduced, in HeLa cell lysates compared to RRL. An antibody against ribosomal protein RPS6 was used as a loading control. Thus, the requirement for exogenous eIF4E is consistent with the presence of inactive eIF4E in this lysate. FIG. 2B shows the quantification of western blot results in FIG. 2A, and demonstrates that eIF4E is present in HeLa extracts, but is reduced compared to RRL. Shown is the level of eIF4E protein relative to RPS6 (n=4; Mean+SEM; *p<0.05). FIG. 2C confirms that reporter mRNAs were not degraded during the course of the in vitro translation reactions. To test this, various reporter RNAs were subjected to ethidium bromide staining after separation by denaturing agarose gel electrophoresis. The sequence and modified nucleotide of each mRNA is indicated. For modified mRNAs, all base modifications were added to the in vitro transcription reaction at 50% relative to the respective unmodified base, with the exception of mRNAs containing the HIST2H2BE 5' UTR, in which m$^6$A was incorporated only at the first transcribed nucleotide. These results show that RNA levels were the same for both the A, m$^6$A, and other modified base reporters. In FIG. 2D, mRNA levels were measured by RT-qPCR after completion of in vitro translation assays to ensure that selective degradation did not occur for A- or m$^6$A-containing mRNAs. RNA from in vitro translation assays was isolated after completion of the assay, and RT-qPCR was performed to measure the amount of luciferase mRNA in each sample. Levels of reporter mRNA were normalized to 18S rRNA in each sample and then averaged across all samples separately for A- and m$^6$A-containing mRNAs. Shown are the mean mRNA levels for all mRNAs used in in vitro translation assays. The results indicate that A- and m$^6$A-containing mRNAs exhibit similar stabilities during the course of the in vitro translation assays (n=26, mean+SEM; p=0.499). FIG. 2E further tests the stability of A- and m$^6$A-containing mRNAs in in vitro translation assays. mRNAs containing A or 50% m$^6$A and labeled with [$^{32}$P]-C were first synthesized and then incubated with HeLa lysates for 30 minutes as for in vitro translation assays. RNA was then isolated, separated by PAGE, and transferred to a nylon membrane. Radiolabeled mRNAs were then detected by autoradiography. Both A- and m$^6$A-containing mRNAs are highly stable following incubation with HeLa cell extracts (shown are three replicate experiments for A- and m$^6$A-containing mRNAs). In FIG. 2F, sequences of the various 5' UTRs (β-globin (SEQ ID NO:1), β-globin 1 A mid (SEQ ID NO:2), β-globin 3 As (SEQ ID NO:3), β-globin 0 As (SEQ ID NO:4), β-globin 1 A 5' end (SEQ ID NO:5), β-globin 1 A 3' end (SEQ ID NO:6), HIST2H2BE (SEQ ID NO:7), pGL4.34 vector (SEQ ID NO:8), and β-globin Hairpin (SEQ ID NO:9)) used in the figure panels in FIGS. 3A-3E and 4A-4D are shown. The A residues in each sequence which are potentially methylated in the m$^6$A-containing version of the mRNA are underlined. For all mRNAs except those containing the HIST2H2BE 5' UTR sequence, methylated versions of the mRNA contained m$^6$A at a level of 50% relative to A. For the HIST2H2BE 5' UTR-containing mRNA, only the first A residue of the mRNA was modified to contain m$^6$A, as indicated by underlining. The figure panels within FIGS. 3A-3E and 4A-4D which used each mRNA are also indicated. FIG. 2G shows that cap-independent translation is induced by m⁶A and not by other mRNA modifications. In vitro translation was performed in HeLa cell extracts using mRNAs synthesized to contain 50% 1V⁶-methyladenosine, $N^1$-methyladenosine, $N^6$-progargyladenosine, 5-methyl cytosine, pseudouridine, or 2'-O-methyladenosine as indicated. Only the m⁶A-containing mRNA is translated, demonstrating that m⁶A specifically induces the observed cap-independent translation (n=3; mean±SD; *p<0.01, **p<0.001). In FIG. 2H, reporter mRNAs were synthesized which encoded a truncated GFP protein comprising the C-terminal end of GFP which is initiated by the internal AUG site in FIG. 4. To confirm that this protein can be detected by the anti-GFP antibody used in FIG. 4, uncapped A- and m⁶A-containing mRNAs encoding this protein which lacked the canonical AUG initiation site encoding full-length GFP was synthesized. These mRNAs were then used in in vitro translation assays using HeLa cell extracts. Protein products were separated by SDS-PAGE and subjected to western blotting using the anti-GFP C-terminal epitope antibody. The predicted ~17 kDa protein product was readily detected by the antibody. Furthermore, only the m⁶A-containing mRNA produced the truncated GFP product, consistent with the ability of m⁶A to promote cap-independent translation. RPS6 immunostaining is shown as a loading control.

FIGS. 3A-3E demonstrate that m⁶A within the 5' UTR enables cap-independent translation of mRNA. FIG. 3A shows that 5' UTR m⁶A permits mRNA translation without the need for the cap-binding protein eIF4E. In vitro translation was performed using a HeLa cell extract mixed with luciferase-encoding, capped mRNA containing either A or m⁶A. Protein production was measured by quantifying luciferase activity. Cap-dependent translation is observed from both methylated and unmethylated mRNAs in the presence of eIF4E. However, when eIF4E is absent, only the m⁶A-containing mRNA is translated (n=4; Mean+SD; ***p<0.0001). FIG. 3B illustrates that the presence of a 5' cap analog is unable to abolish m⁶A-induced mRNA translation. Luciferase mRNAs were translated as in FIG. 3A. 1 mM free cap analog (m7GpppG) was added to sequester cap-binding proteins. Addition of m7GpppG abolishes cap-dependent translation of unmethylated mRNA (left), but is unable to abolish the cap-independent translation induced by m⁶A (right). Levels of luciferase activity are shown relative to capped mRNA +10 pmole eIF4E (n=3; Mean+SD; *p<0.01, ** p<0.001). FIG. 3C shows in vitro translation performed using luciferase-encoding mRNA containing A or 50% m⁶A and with or without a 5' cap as indicated. While unmethylated, capped mRNA +10 pmole eIF4E is robustly translated, the unmethylated, uncapped mRNA fails to be translated. However, m⁶A-containing mRNA is efficiently translated even when no 5' cap is present (n=3; Mean+SD; *p<0.01). FIG. 3D shows that m⁶A residues in the coding sequence do not induce cap-independent translation. Uncapped, luciferase-encoding mRNAs containing either the natural β-globin 5' UTR or a modified β-globin 5' UTR containing either zero, one, or three A residues as indicated were used for in vitro translation assays. Translation of m⁶A-containing mRNA with zero A residues in the 5' UTR was markedly diminished, indicating that coding sequence m⁶A residues are unable to induce cap-independent translation. However, when a single m⁶A was added to the 5' UTR, the transcripts were robustly translated. Methylated 5' UTRs with a single A near the 5' end, the middle (mid), or near the 3' end all showed similar levels of translation (n=3; mean+SD; p<0.001, * p<0.0001, ** p<0.00001). The schematic shows the distribution of A residues within each β-globin 5' UTR variant (the unmodified β-globin 5' UTR contains 17 A residues). FIG. 3E shows that mRNA with a single m⁶A within the 5' UTR and no m⁶As in the remainder of the transcript induces cap-independent translation. Uncapped, luciferase-encoding mRNAs which contained either a single adenosine 5'-monophosphate (AMP) or $N^6$-methyladenosine 5'-monophosphate (m⁶AMP) at the 5' end were used for in vitro translation. Only the m⁶A-containing mRNA was translated, demonstrating that a single 5' end m⁶A residue is capable of inducing cap-independent translation (n=3; Mean+SD; p<0.001). The reduced translation efficiency of this mRNA compared to mRNAs with internally methylated 5' UTRs is likely due to inefficient incorporation of m⁶A residues at the 5' end by T7 RNA polymerase. See also FIGS. 2A-2H.

FIGS. 4A-4D show that m⁶A-mediated translation occurs through a 5' end-dependent mechanism. FIG. 4A shows the results of toe-printing assays performed using a capped, m⁶A-containing mRNA containing the β-globin 5' UTR sequence which was modified to include two AUG initiation codons ("AUG1" and "AUG2" in the schematic). The majority of 48S complexes were assembled at AUG1, with negligible levels of 48S complexes detected at AUG2. In FIG. 4B, uncapped A- or m⁶A-containing mRNAs containing encoding GFP were used for in vitro translation. The mRNA contains two near-kozak start codons: AUG 1 encodes the full-length GFP protein, and internally-localized AUG2 encodes an in-frame truncated (~17 kDa) protein comprising the C-terminal portion of GFP. Full-length and truncated GFP protein levels (sizes indicated by arrows) were measured by western blot. m⁶A primarily promotes translation of the full-length protein and fails to induce internal entry-mediated translation from AUG2. Levels of the ribosomal protein RPS6 are shown as a loading control. FIG. 4C shows the quantification of full-length GFP protein levels in FIG. 4B and demonstrates increased protein expression of methylated mRNA versus unmethylated mRNA (n=3; mean+SD; **p<0.001). FIG. 4D illustrates that the presence of a stable hairpin at the beginning of the 5' UTR to block 5' end entry severely attenuates m⁶A-mediated translation (n=3; mean+SD; *p<0.01). See also FIGS. 2A-2H.

In FIG. 5A, the indicated proteins/protein complexes were incubated with radiolabeled A- or m⁶A-containing RNA probes and crosslinked. Unbound RNAs then removed with RNase I, proteins were separated by SDS-PAGE, and radioactively-labeled RNAs were detected. eIF1, eIF1A, eIF2, and the 40S ribosomal subunit show no preferential crosslinking to methylated RNA. However, eIF3 preparations exhibit strong crosslinking to methylated RNA at bands around 60 kD, 80 kD, and 110-160 kD, which correspond to multiple subunits of the eIF3 complex as indicated. In FIG. 5B, crosslinking assays were performed as in FIG. 5A using the HeLa cell extracts utilized in in vitro translation assays. The eIF3 complex was immunoprecipitated using antibodies against eIF3a or eIF3b, and proteins containing crosslinked RNA were detected. Both eIF3 antibodies precipitated proteins that preferentially crosslinked to m⁶A RNA. Immunoprecipitation using rabbit and mouse IgG control antibodies are shown as negative controls. Western blotting for the indicated proteins indicates their enrichment following immunoprecipitation (bottom). The input lanes throughout have 25% of the material loaded for the IP lanes. See also FIGS. 6A-6F and 7A-7D.

FIGS. 6A-6F show the characterization of eIF3 binding to m⁶A-containing RNA (related to FIGS. 5A-5B). In FIG. 6A, initiation factor preparations used for crosslinking experiments in FIG. 5A were separated by SDS-PAGE and subjected to silver staining to visualize all initiation factor subunit bands and co-purified protein bands (bottom; [$^{32}$P] blots from FIG. 5A are shown above as a reference). Bands corresponding to individual eIF3 subunits are indicated, according to previous characterization of the same initiation factor preparations (Pisarev et al., "Assembly and Analysis of Eukaryotic Translation Initiation Complexes," *Methods Enzymol.* 430:147-177 (2007), which is hereby incorporated by reference in its entirety). FIG. 6B shows the visualization of purified eIF3 and reveals individual protein subunits within the eIF3 multiprotein complex. Purified eIF3 was separated by SDS-PAGE and subjected to SimplyBlue staining to reveal individual bands. Bands corresponding to individual eIF3 subunits are indicated (4 symbol refers to truncation products of indicated subunits as validated by mass spectrometry). In FIG. 6C, the goal was to determine if eIF4E crosslinks to m$^6$A-containing mRNA. Although m$^6$A-dependent translation is eIF4E independent, applicants asked if it could still bind eIF4E. To test this, crosslinking was used, similar to what is shown in FIG. 5A. Crosslinking assays with purified eIF3 or eIF4E were performed with A- or m$^6$A-containing [$^{32}$P]-labeled RNA probes. Proteins were then separated by PAGE and silver stained. Crosslinked RNAs were visualized by [$^{32}$P] detection after membrane transfer. eIF3 protein showed preferential crosslinking to m$^6$A-containing RNA compared to A-containing RNA. However, the cap-binding protein eIF4E failed to bind to A- or m$^6$A-containing RNA probes, indicating very low levels of non-specific binding in the crosslinking assay. FIG. 6D shows that eIF3 binds to methylated RNAs whether m$^6$A is near the 5' end or in the middle of the transcript. UV-crosslinking assays were performed using purified eIF3 and radiolabeled RNA probes containing A or m$^6$A as in FIG. 5A. The sequence surrounding the central GGAC (underlined adenosine is A or m$^6$A) was varied as indicated. Multiple eIF3 subunits exhibit increased binding to m$^6$A-containing RNA over A-containing RNA whether the m$^6$A is located near the 5' end of the RNA or in the middle. Initiation factor preparations used for crosslinking experiments were separated by SDS-PAGE and subjected to silver staining to visualize all initiation factor subunit bands and co-purified protein bands (bottom). Bands corresponding to individual eIF3 subunits are indicated. In FIG. 6E, eIF3 preferentially binds to m$^6$A in its naturally-occurring GAC sequence context. UV-crosslinking assays were performed using RNAs containing either A or m$^6$A within the sequence contexts indicated (GAC, UAC, or CAG). eIF3 exhibits preferential crosslinking to m$^6$A-containing RNA in a GAC context, which matches the consensus sequence for m$^6$A. However, this preferential binding is lost when m$^6$A is present in a non-consensus context (UAC or CAG). Initiation factor preparations used for crosslinking experiments were separated by SDS-PAGE and subjected to silver staining to visualize all initiation factor subunit bands and co-purified protein bands (bottom). Bands corresponding to individual eIF3 subunits are indicated. FIG. 6F demonstrates that 5' UTR m$^6$A residues efficiently promote cap-independent translation when they are in a GAC consensus. Uncapped, luciferase-encoding mRNAs containing a modified β-globin 5' UTR with a single m$^6$A residue were used for in vitro translation assays using HeLa extracts. When the m$^6$A residue was in a GAC consensus, robust cap-independent translation was induced. However, when the m$^6$A residue was in a non-canonical sequence (UAC or CAG, as indicated), markedly lower levels of cap-independent translation were observed, suggesting that eIF3 preferentially recognizes m$^6$A residues in the canonical GAC consensus sequence to mediate cap-independent translation (n=3; mean±SD; ***p<0.0005).

FIGS. 7A-7D show that eIF3 from HeLa cell lysates selectively crosslinks to m$^6$A-containing RNA and does not co-purify with YTH proteins, related to FIGS. 5A-5B. FIG. 7A shows the protein loading controls for the data shown in FIG. 5B. As described for FIG. 5B, HeLa cell lysates used for in vitro translation assays were crosslinked to [$^{32}$P]-labeled, A- or m$^6$A-containing RNA probes, and protein/RNA complexes were immunoprecipitated with antibodies to eIF3a, eIF3b, or IgG control. Immunoprecipitated protein/RNA complexes were then separated by PAGE, transferred to nitrocellulose membranes, and radioactive RNA was detected. [$^{32}$P] blots demonstrate preferential crosslinking of immunoprecipitated eIF3 to m$^6$A-containing RNA versus A-containing RNA (top). Immunoprecipitation with IgG control antibody showed no crosslinking to either A- or m$^6$A-containing RNA. Western blots (middle) confirm immunoprecipitation of eIF3. Amido black staining of nitrocellulose membranes shows the antibody heavy chain (H-chain) and light chain (L-chain). These experiments include RNAse to lower background. The RNAse is also visible in the protein stained blot. The input lanes throughout have 25% of the material loaded for the IP lanes. In FIG. 7B, crosslinking of HeLa cell lysates to RNA probes was performed as in FIG. 7A, and immunoprecipitation was performed with an antibody against ABCF1 or IgG as control. [$^{32}$P] blots demonstrate no crosslinking of immunoprecipitated ABCF1 to either A- or m$^6$A-containing RNA (top). IgG control antibody immunoprecipitation also showed no crosslinking to either A- or m$^6$A-containing RNA. Western blots (middle) confirm immunoprecipitation of ABCF1. Amido black staining of protein gels prior to membrane transfer is shown in the bottom panel. The input lanes throughout have 25% of the material loaded for the IP lanes. FIG. 7C shows mass spectrometry analysis of purified eIF3. eIF3 was immunopurified from rabbit reticulocyte lysates (RRL) as was done for in vitro toe-printing and crosslinking assays. Following separation by SDS-PAGE, bands from the 60-80 kDa range were cut out and subjected to mass spectrometry analysis. The table in FIG. 7C lists the proteins identified, the molecular weight, and the number of peptides identified for each protein. Peptides from eIF3 subunits constitute the majority of the peptides identified. None of the YTH domain-containing proteins were identified. In FIG. 7D, eIF3 was immunopurified from RRL as in FIG. 7A. 10 μg of purified eIF3 was then subjected to western blotting to detect co-purifying proteins. 10 μg of HeLa cell extract and RRL extract were also run as controls. The eIF3c subunit shows marked enrichment in the purified eIF3 preparation. However, the m$^6$A binding proteins YTHDF1, 2, and 3 did not co-purify with eIF3 and are not detectable in the eIF3 preparation. Additionally, the YTH domain-containing proteins YTHDC1 and 2 also failed to co-purify with eIF3. These data, along with silver staining of the eIF3 preparation and the MS analysis of purified eIF3, confirm that no YTH-protein contaminant is present in the purified eIF3 preparation.

FIGS. 8A-8E show that eIF3 PAR-iCLIP clusters overlap with m$^6$A sites within 5' UTRs (related to FIGS. 9A-9B). FIG. 8A demonstrates that eIF3 binds predominantly to 5' UTRs of cellular mRNAs. PAR-iCLIP was performed using an antibody against endogenous eIF3a to detect cellular eIF3-binding regions in the transcriptome. Shown is a metagene analysis which depicts the density of eIF3 binding site clusters along the length of an mRNA. Similar to previous reports of cellular eIF3 binding using PAR-CLIP (Lee et al., "eIF3 Targets Cell-Proliferation Messenger RNAs for Translational Activation or Repression," Nature 522:111-114 (2015), which is hereby incorporated by reference in its entirety) analysis reveals that eIF3 predominantly binds to mRNAs within their 5' UTRs. FIG. 8B shows the analysis of the correlation between eIF3a PAR-iCLIP replicate datasets (left) between eIF3a PAR-iCLIP data and eIF3 PAR-CLIP data (Lee et al.,"eIF3 Targets Cell-Proliferation Messenger RNAs for Translational Activation or Repression," Nature 522:111-114 (2015), which is hereby incorporated by reference in its entirety) (middle), and between eIF3 PAR-CLIP replicate datasets from Lee et al.,"eIF3 Targets Cell-Proliferation Messenger RNAs for Translational Activation or Repression," Nature 522:111-114 (2015) (which is hereby incorporated by reference in its entirety) (right) in 100 nucleotide window bins. The PAR-iCLIP replicates showed high correlation (left, r=0.90). Applicants also asked if the PAR-iCLIP datasets generated here show correlation with the previously published PAR-CLIP eIF3 dataset (Lee et al., "eIF3 Targets Cell-Proliferation Messenger RNAs for Translational Activation or Repression," Nature 522:111-114 (2015), which is hereby incorporated by reference in its entirety). These datasets showed high correlation (r=0.67). To establish a control for this comparison, the correlation between replicates within the Lee et al., "eIF3 Targets Cell-Proliferation Messenger RNAs for Translational Activation or Repression," Nature 522:111-114 (2015) (which is hereby incorporated by reference in its entirety) dataset (right), which showed a similar correlation (r=0.73) was calculated. Association was tested using Pearson's correlation test. RPM=reads per million mapped reads. In FIG. 8C, overlap between eIF3 binding sites detected by eIF3a PAR-iCLIP and m$^6$A sites in 5' UTRs of mRNAs in HEK293 cells is shown. eIF3a binding sites overlap with 35% of m$^6$A sites located in 5' UTRs. m$^6$A sites were detected by the CIMS miCLIP single-nucleotide resolution mapping approach (Linder et al., "Single-Nucleotide-Resolution Mapping of m$^6$A and m$^6$Am Throughout the Transcriptome," Nat. Methods 12(8):767-72 (2015), which is hereby incorporated by reference in its entirety) and compared to eIF3a PAR-iCLIP read clusters. The statistical significance of the overlap (p<0.01, using non-parametric shuffling test) was computed using 100 random shufflings of eIF3a peaks within the same 5' UTR regions where they occur. FIG. 8D shows that eIF3-binding sites are enriched near 5' UTR m$^6$A residues. Mean read counts from eIF3a PAR-iCLIP clusters were plotted in 10 nucleotide bins surrounding m$^6$A sites in 5' UTRs. An equal number of random genomic coordinates corresponding to A residues was generated from the same set of 5' UTRs used for the m$^6$A analysis. Enrichment of mean eIF3a PAR-iCLIP read counts within 10 nucleotides up- and downstream of m$^6$A sites was compared to the randomly chosen A sites (100 iterations) using a one sample t-test. This analysis shows significant enrichment of eIF3 read clusters centered around 5' UTR m$^6$A residues compared to randomly selected A residues. FIG. 8E is a table showing multiple analyses of overlap between eIF3a PAR-iCLIP sites and m$^6$A sites in cellular 5' UTRs. There was a statistically significantly higher level of overlap between eIF3a and m$^6$A sites than is expected by chance, regardless of window size used for analysis.

FIG. 9A shows read clusters from both eIF3 PAR-iCLIP and single nucleotide-resolution m$^6$A mapping (Linder et al., "Single-Nucleotide-Resolution Mapping of m$^6$A and m$^6$Am Throughout the Transcriptome," Nat. Methods 12(8):767-72 (2015), which is hereby incorporated by reference in its entirety) (miCLIP; red) for four representative mRNAs (EIF4A3, H3F3C, SQLE, and IER5). eIF3a PAR-iCLIP read clusters exhibit highly specific overlap with m$^6$A mapping clusters at internal positions within 5' UTRs. This co-localization is specific to 5' UTRs, as mRNAs which contain multiple m$^6$A residues in the CDS or 3' UTR fail to show eIF3a binding at these sites (exemplified by IER5). Asterisks indicate the location of individual m$^6$A sites identified at single-nucleotide resolution. FIG. 9B shows that eIF3 binds to the 5' UTR of cellular mRNAs in an m$^6$A-dependent manner. HEK293 cells were transfected with GFP- or Fto-overexpression plasmids, and eIF3 immuno-precipitation was performed to isolate eIF3-bound mRNAs. Bound mRNAs were quantified by RT-qPCR using 5' UTR-specific primers. 5' UTRs of mRNAs that contain high levels of m$^6$A exhibited reduced binding to eIF3 after overexpression of Fto. 5' UTRs which do not contain m$^6$A exhibited no change in eIF3 binding following Fto overexpression (n=3; error bars represent SEM). See also FIGS. 8A-8E and FIGS. 11A-11B.

FIGS. 10A-10F show that m$^6$A mediates stress-induced translation of Hsp70. FIG. 10A shows that depletion of the m$^6$A methyltransferase, METTL3, decreases the translational efficiency ("TE") of mRNAs with 5' UTR m$^6$A. Ribosome profiling data from HeLa cells expressing METTL3 or control siRNAs (Wang et al., "N(6)-Methyladenosine Modulates Messenger RNA Translation Efficiency," Cell 161:1388-1399 (2015), which is hereby incorporated by reference in its entirety) was used to determine changes in TE for various classes of mRNAs defined by single nucleotide-resolution m$^6$A mapping. Compared to nonmethylated mRNAs, transcripts with m$^6$A residues in the coding sequence (CDS) or 3' UTR exhibit only a marginal decrease in TE. However, mRNAs containing m$^6$A within the 5' UTR show a large reduction in TE. P-values were calculated using the Mann-Whitney test. In FIG. 10B, TE of various classes of m$^6$A-containing mRNAs were analyzed using ribosome profiling datasets from HeLa cells as described in FIG. 6A. Shown are the mean fold changes in TE (siMETTL3/siControl) for mRNAs with m$^6$A residues only in the 5' UTR, within the 3' UTR, within 50 nt of the stop codon, within the CDS and/or 3' UTR, or in all mRNAs, as defined by single-nucleotide resolution m$^6$A mapping. mRNAs with 5' UTR m$^6$A residues exhibit a dramatic reduction in TE after METTL3 depletion, whereas transcripts with m$^6$As in other regions fail to show this effect. All mean fold change TE values were computed after background subtraction of the mean fold change computed from all nonmethylated control mRNAs, as indicated by the arrow (*P<0.05). FIG. 10C shows that Fto knockdown increases heat shock-induced translation of Hsp70. MEF cells stably expressing either Fto shRNA or scramble shRNA were subjected to heat shock stress. Cell lysates were collected at various times post-heat shock ("Post HS") and then used for western blot analysis with the indicated antibodies. Fto knockdown increased the levels of stress-induced Hsp70 protein compared to control shRNA ("S exp"=short exposure; "L exp"=long exposure). Levels of Hsp25, another heat shock-induced protein, were unaffected by Fto knockdown. The right panel shows quantification of Hsp70 levels normalized by β-actin (n=3; mean +SEM; **p<0.1). In FIG. 10D, MEFs stably expressing control or Fto shRNA were subjected to heat shock stress as in FIG. 10C. Polysome fractions were separated using sucrose gradient fractionation (left panels)

followed by RT-qPCR for Hsp70 (top right panel) and Gapdh (bottom right panel) in each fraction. Hsp70 levels are increased in polysome fractions following Fto knockdown, whereas the distribution of Gapdh is unchanged (n=3; mean+SEM; Hsp70: p=0.0007, 2-way ANOVA; Gapdh: p=0.3722, 2-way ANOVA considering the entire range of time points). In FIG. 10E, MEF cells were infected with either GFP or Fto lentivirus and subjected to heat shock stress. Cell lysates were collected at various times post-heat shock and then used for western blot analysis with the indicated antibodies. Fto overexpression decreased the levels of heat shock-induced Hsp70 protein compared to GFP overexpression. Levels of Hsp25 were unaffected by Fto overexpression. The right panel shows quantification of Hsp70 levels normalized to (3-actin (n=3; mean+SEM; *p<0.5). FIG. 1OF shows that MEFs with or without Fto overexpression were subjected to heat shock stress as in FIG. 10E). Polysome fractions were separated using sucrose gradient fractionation (left panels) followed by RT-qPCR of Hsp70 (top right panel) and Gapdh (bottom right panel) in each fraction. Hsp70 levels are decreased in polysome fractions following Fto overexpression, whereas the distribution of Gapdh is unchanged (n=3; mean+SEM; Hsp70: p<0.0001, 2-way ANOVA; Gapdh: p=0.1910, 2-way ANOVA considering the entire range of time points). See also FIGS. 11A-11B and FIGS. 12A-12D.

FIG. 11A shows that eIF3a PAR-iCLIP detects eIF3 binding sites which exhibit a high degree of overlap with previously reported (Lee et al., "eIF3 Targets Cell-Proliferation Messenger RNAs for Translational Activation or Repression," Nature 522:111-114 (2015), which is hereby incorporated by reference in its entirety) eIF3 binding sites as well as $m^6A$ sites (Linder et al., "Single-Nucleotide-Resolution Mapping of $m^6A$ and $m^6Am$ Throughout the Transcriptome," Nat. Methods 12(8):767-72 (2015), which is hereby incorporated by reference in its entirety) in 5' UTRs. This figure shows mRNAs presented in FIG. 9A, as well as additional examples and additional alignments. Two eIF3 CLIP studies are shown: eIF3a PAR-iCLIP read clusters and eIF3 PAR-CLIP clusters. The $m^6A$ miCLIP mapping read clusters are also shown. To show that the $m^6A$ or eIF3 peaks are not an artifact of uneven RNA recovery, the RNA-Seq reads are also displayed. To determine if eIF3 binding is occurring at the related nucleotide $m^6Am$, the CAGE tags (Lykke-Andersen et al., "Human Nonsense-Mediated RNA Decay Initiates Widely by Endonucleolysis and Targets snoRNA Host Genes," Genes Dev. 28:2498-517 (2014), which is hereby incorporated by reference in its entirety) are shown. CAGE tags occur at transcription start sites, which are the only location of the $m^6Am$ nucleotide. Applicant's eIF3a PAR-iCLIP and the previously published eIF3 PAR-CLIP clusters show a high degree of overlap. The eIF3 PAR-CLIP is filtered while the eIF3a shows raw unfiltered reads. The clusters from both datasets are also highly specific, as they show a distinct distribution from that of RNA-Seq reads. Additionally, $m^6Am$ sites are likely to exist when the CAGE tags and miCLIP peaks are aligned (e.g., EIF4A3 and EIF5). In both cases, no eIF3 reads are seen at these sites, but are found downstream, aligned with internal $m^6A$ residues within the 5' UTR. Thus, eIF3 shows preferential binding to 5' UTRs at sites of $m^6A$ versus $m^6Am$ for these mRNAs. Asterisks indicate sites of $m^6A$ residues identified by single-nucleotide resolution mapping. FIG. 11B shows that YTHDF 1 depletion does not affect the translation efficiency of mRNAs containing 5' UTR $m^6A$. Applicants analyzed ribosome profiling data from control and YTHDF1-knockdown HeLa cells (Wang et al., "N(6)-Methyladenosine Modulates Messenger RNA Translation Efficiency," Cell 161:1388-1399 (2015), which is hereby incorporated by reference in its entirety). As a control, ribosome profiling datasets from control and METTL3-knockdown HeLa cells (Wang et al., "N(6)-Methyladenosine Modulates Messenger RNA Translation Efficiency," Cell 161:1388-1399 (2015), which is hereby incorporated by reference in its entirety) were used. Shown are the mean log(2) fold changes in TE (left panel: siYTHDF1/siControl; right panel: siMETTL3/siControl) for mRNAs with $m^6A$ residues exclusively in the 5' UTR, mRNAs with $m^6A$ in the 3' UTR, and all mRNAs. The mRNAs were classified into these groups based on single-nucleotide resolution mapping of $m^6A$ residues in the human transcriptome (Linder et al., "Single-Nucleotide-Resolution Mapping of $m^6A$ and $m^6Am$ Throughout the Transcriptome," Nat. Methods 12(8):767-72 (2015), which is hereby incorporated by reference in its entirety). YTHDF1 knockdown caused global suppression of translation in all mRNAs, with no significant difference in TE decreases between the indicated classes of methylated mRNAs. P-values for mean TE changes relative to all mRNAs are 0.316 (5' UTR $m^6A$ mRNAs) and 0.335 (3' UTR $m^6A$ mRNAs). In contrast, depletion of METTL3 caused a significant decrease in TE of mRNAs that contain $m^6A$ residues exclusively within their 5' UTR (P=0.001). However, the TE of mRNAs with $m^6A$ residues in the 3' UTR was not significantly altered after METTL3 depletion (P=0.412). Background subtraction for all mRNAs was done using the mean TE fold change of unmethylated mRNAs.

FIGS. 12A-12D show that $m^6A$ patterns are reshaped by cellular stress (related to FIGS. 10A-10F). FIG. 12A shows that Fto demethylates $m^6A$ in Hsp70 mRNA. Left: MEF cells were infected with Fto or GFP lentivirus and subjected to heat shock, and Hsp70 mRNA was then isolated by hybridization to a biotinylated capture probe. 2 µg of captured Hsp70 mRNA was then run out on a gel, transferred to a nylon membrane, and subjected to $m^6A$ immunoblotting. Fto overexpression causes a substantial reduction of heat shock-induced $m^6A$ within Hsp70 compared to GFP overexpression, confirming that Fto targets Hsp70 for demethylation. An in vitro transcribed RNA containing 100% A or 50% $m^6A$ was blotted in parallel to confirm specificity of the $m^6A$ signal. Right: MEF cells stably expressing scramble or Fto shRNA were subjected to heat shock, and Hsp70 mRNA was then isolated and subjected to $m^6A$ immunoblotting. Compared to Hsp70 isolated from scramble shRNA-expressing cells, Hsp70 isolated from Fto knockdown cells exhibits an increase in $m^6A$ content. An in vitro transcribed RNA containing 100% A or 50% $m^6A$ was blotted in parallel to confirm specificity of the $m^6A$ signal. FIG. 12B shows that knockdown or overexpression of Fto in MEF cells does not alter Hsp70 total mRNA levels. Top: MEF cells were infected with Fto or scramble shRNA lentivirus and subjected to heat shock for 1 hour at 42° C., then allowed to recover at 37° C. RNA was isolated at indicated time points and used for RT-qPCR to detect Hsp70 mRNA levels relative to Gapdh mRNA. Fto knockdown did not affect the levels of Hsp70 mRNA (n=3, Mean±SEM; p=0.999, 2-way ANOVA). Bottom: Fto- or GFP-overexpressing MEF cells were subjected to heat shock and RT-qPCR was performed as described for the left panel. Fto overexpression did not affect the levels of Hsp70 mRNA (n=3, mean+SEM; p=0.588, 2-way ANOVA). In FIG. 12C, single-nucleotide resolution $m^6A$ profiling (miCLIP) was performed on cells subjected to heat shock to determine the global effects of heat shock on the cellular m6A landscape. miCLIP distinguishes m⁶Am from m⁶A and identifies the precise position of m⁶A residues in mRNAs (Linder et al., "Single-Nucleotide-Resolution Mapping of m⁶A and m⁶Am Throughout the Transcriptome," Nat. Methods 12(8):767-72 (2015), which is hereby incorporated by reference in its entirety). Shown are metagene profiles of m⁶A residues for untreated cells and heat-shocked cells. Heat shock was performed at 42° C. for 1 hour, followed by a 6 hour recovery. RNA was harvested for miCLIP analysis at the 6 hour time point. miCLIP analysis was performed on a minimum of three separate biological replicates, and representative metagene profiles are shown. These results demonstrate that heat shock induces a substantial increase in 5' UTR m⁶A levels in cellular mRNAs. In FIG. 12D, existing MeRIP-Seq datasets which profiled m⁶A in cellular mRNAs exposed to various treatments were mined (Dominissini et al., "Topology of the Human and Mouse m6A RNA Methylomes Revealed by m6A-Seq.," Nature 485:201-206 (2012), which is hereby incorporated by reference in its entirety) to further demonstrate that heat shock induces increased m⁶A levels specifically in 5' UTRs. A metagene analysis was used to determine if the cellular stress resulted in a redistribution of m⁶A. These experiments were performed in HepG2 cells, with the vehicle-treated cells as the control condition (Dominissini et al., "Topology of the Human and Mouse m6A RNA Methylomes Revealed by m6A-Seq.," Nature 485:201-206 (2012), which is hereby incorporated by reference in its entirety). Compared to untreated HepG2 cells, both heat shock and UV treatment cause a marked increase in 5' UTR m⁶A levels. However, interferon-γ (IFN-γ) treatment fails to elicit this effect, suggesting that specific cellular stress-response pathways are involved in 5' UTR m⁶A induction.

FIGS. 13A-13D show that selective 5' UTR m⁶A modification mediates cap-independent translation. In FIG. 13A, MEF cells transfected with Fluc mRNA reporters were subject to heat shock treatment and the Fluc activity was measured by real-time luminometry. Fluc activities were quantified and normalized to the sample containing normal adenosine nucleotides. Red, m⁶A; green, 2'-O-MeA. In FIG. 13B, constructs expressing Fluc reporter with Hsp70 5' UTR or the one with A103C mutation are depicted on the top. Fluc activities in transfected MEF cells were quantified and normalized to the control containing normal A without stress. In FIG. 13C, Fluc mRNAs bearing Hsp70 5' UTR with a single m⁶A site were constructed using sequential splint ligation. After in vitro translation in rabbit reticulate lysates, Fluc activities were quantified and normalized to the control lacking m⁶A. Error bars, mean±s.e.m.; *P<0.05, unpaired two-tailed t-test; n=3 biological replicates (a, b and c). FIG. 13D illustrates a proposed model for dynamic m⁶A 5' UTR methylation in response to stress and its role in cap-independent translation. Under the normal growth condition, nuclear FTO demethylates the 5' UTR m⁶A from nascent transcripts and the matured transcripts are translated via a cap-dependent mechanism. Under stress conditions, nuclear localization of YTHDF2 protects the 5' UTR of stress-induced transcripts from demethylation. With enhanced 5' UTR methylation, these transcripts are selectively translated via a cap-independent mechanism.

FIGS. 14A-14B show that m⁶A modification promotes cap-independent translation. In FIG. 14A, Fluc reporter mRNAs with or without 5' UTR was synthesized in the absence or presence of m⁶A. The transfected MEFs were incubated in the presence of 5 μg ml⁻¹ ActD. At the indicated times, mRNA levels were determined by qPCR. Error bars, mean±s.e.m.; n=3 biological replicates. In FIG. 14B, Fluc reporter mRNAs with or without Hsp70 5' UTR was synthesized in the absence or presence of m⁶A, followed by addition of a non-functional cap analogue AppG. Fluc activity in transfected MEF cells was recorded using real-time luminometry.

FIG. 15A shows sequences of HSPA1A template (SEQ ID NO:10) and the DNA primer (SEQ ID NO:11) used for site-specific detection. Synthesized mRNAs containing a single m⁶A site or A are used as positive (SEQ ID NO:12) and negative (SEQ ID NO:13) controls, respectively. The shading in the HSPA1A sequence indicates predicted m⁶A sites. Autoradiogram shows primer extension of controls (left panel) and endogenous HSPA1A (right panel). In FIG. 15B, mRNAs with or without m⁶A incorporation were incubated in the rabbit reticulocyte lysate system (RRL) at 30° C. for up to 60 minutes. Messenger RNA levels were determined by qPCR. Error bars, mean±s.e.m.; n=3 biological replicates.

DETAILED DESCRIPTION OF THE INVENTION

Figure 1A:
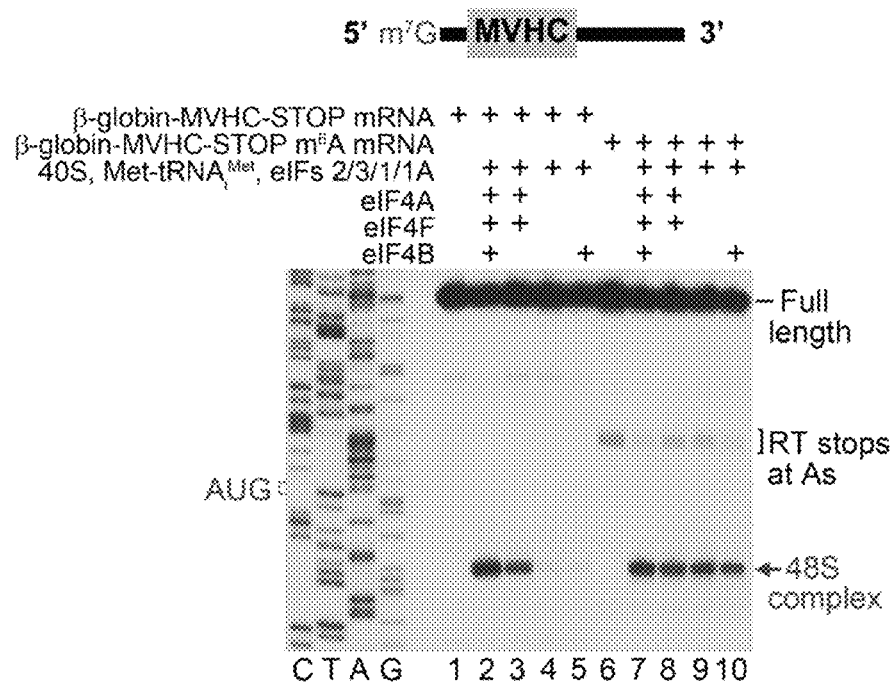
FIGS. 1A-1C demonstrate that 5' UTR m$^6$A enables ribosome binding to mRNA in the absence of cap-binding proteins. In particular, FIG. 1A demonstrates that 5' UTR methylation permits 48S initiation complex formation in the absence of the group 4 eIFs. In vitro transcribed, capped mRNAs encoding a MVHC tetrapeptide and containing either A or m$^6$A were incubated with purified mammalian translation initiation components. Subsequent toe-printing analysis using a radiolabeled primer then revealed whether 48S initiation complexes were formed. Positions of the initiation codon, full-length cDNA, and the 48S complex are shown on the sides of the panels. Lanes C/T/A/G depict the corresponding DNA sequence. When unmethylated mRNA is used (lanes 1-5), 48S complexes are only formed when the cap-binding complex eIF4F is present (lanes 2 and 3). When eIF4F is absent, 48S complex formation on unmethylated mRNA is impaired (lanes 4 and 5). However, when mRNA with m$^6$A in the 5' UTR is used, 48S complex formation is observed even in the absence of eIF4F (lanes 9 and 10; compare to lanes 7 and 8 where eIF4F is present).

The present invention relates to RNA molecules that can effect eIF4E-independent translation to enhance the translation of an encoded protein or polypeptide, and to methods and kits for enhancing translation of RNA molecules and providing treatment.

One aspect of the present invention relates to a method of enhancing the translation ability of an RNA molecule. This method involves providing a cell-free composition comprising an RNA molecule to be translated, where the RNA molecule lacks a methylated adenosine residues in a 5' untranslated region (UTR) and introducing a methylated adenosine residue in a 5' untranslated region (UTR) of the RNA molecule, where said introducing enhances translation ability of the RNA molecule relative to the RNA molecule lacking a methylated adenosine residue in the 5' untranslated region (UTR).

As used herein, the term "cell-free composition" refers to a composition substantially free of intact cells. An exemplary cell-free composition comprises a cell lysate or extract. The term "cell lysate" refers to a fluid containing the contents of lysed cells. Cell lysates may be crude (i.e., unpurified) or partially purified (e.g., to remove cellular debris/particulate such as damaged outer cell membranes). Methods of forming cell lysates are well-known in the art and include, without limitation, sonication, homogenization, enzymatic lysis using lysozyme, freezing, grinding, and high pressure lysis. Cell-free compositions may comprise, for example, ribosomes, amino acids, tRNAs, aminoacyl synthetases, elongation factors and initiation factors. The cell-free composition may be derived from eukaryotic cells or prokaryotic cells and include, for example, E. coli cell lysates or extracts. A "cell-free composition" may also include an in vitro reaction medium for carrying out the well-known steps and reactions of protein synthesis.

A person of ordinary skill in the art will appreciate that there are many types of RNA molecules, including coding RNA (i.e., RNA that is translated into a protein, e.g., mRNA) and non-coding RNA. According to one embodiment, in the present invention, the RNA molecule referred to is a mRNA molecule.

The RNA molecule may be a synthetic RNA molecule or a naturally-occurring RNA molecule. As used herein, the term "synthetic RNA molecule" means an engineered or non-naturally-occurring RNA molecule (e.g., an RNA molecule comprising a heterologous sequence, synthetic nucleotides, a mixture of nucleotides and other chemical moieties, or nucleotide modifications). Synthetic RNA molecules include RNA molecules synthesized using any in vitro method known in the art. For example, synthetic RNA molecules may be produced using in vitro transcription reactions or by using an RNA synthesizer. Synthetic RNA molecules may contain one or more modified ribonucleotides or other nucleotides, for example and without limitation, 2'-O-methylated nucleotides, deoxy nucleotides, or 2'-fluoro nucleotides. A "naturally-occurring RNA molecule" means an RNA molecule consisting of a sequence that occurs in nature.

According to one embodiment of the present invention, the RNA molecule has a 5' untranslated region. As used herein, the terms "5' untranslated region" or "5' UTR" refer to an untranslated nucleotide segment in an RNA molecule immediately preceding an AUG start codon. The 5' untranslated region may be located at the 5' end of an RNA molecule or at an internal position of an mRNA sequence.

In carrying out this aspect of the present invention, an RNA molecule is provided, preferably in a medium in which it does not naturally occur. The RNA molecule may have a 5' untranslated region, but lacks a methylated adenosine residue in the 5' untranslated region. According to the method of the present invention, a methylated adenosine residue is introduced into the 5' untranslated region to enhance the translation ability of the RNA molecule, e.g., relative to the RNA molecule before the methylated adenosine residue was introduced into the 5' untranslated region.

By "enhancing the translation ability" of the RNA molecule, it is meant that the RNA molecule is more likely to be translated, is more efficiently translated, is translated at a higher rate, is translated under more challenging conditions than what normally exist in nature, or is translated under conditions that require fewer reagents than the same RNA molecule that lacks the methylated adenosine residue in the 5' untranslated region.

Various methylated adenosine residues are known in the art and are exemplified in Table 1 below.

TABLE 1

List of Adenosine Base Modifications

| Abbreviation | Chemical name |
| --- | --- |
| $m^1A$ | 1-methyladenosine |
| $m^1Am$ | 1,2'-0-dimethyladenosine |
| $m^2A$ | 2-methyladenosine |
| $ms^2io^6A$ | 2-methylthio-$N^6$-(cis-hydroxyisopentenyl) adenosine |
| $ms^2hn^6A$ | 2-methylthio-$N^6$-hydroxynorvalyl carbamoyladenosine |
| $ms^2i^6A$ | 2-methylthio-$N^6$-isopentenyladenosine |
| $ms^2m^6A$ | 2-methylthio-$N^6$-methyladenosine |
| $ms^2t^6A$ | 2-methylthio-$N^6$-threonyl carbamoyladenosine |
| Am | 2'-O-methyladenosine |
| $m^6t^6A$ | $N^6$-methyl-$N^6$-threonylcarbamoyladenosine |
| $m^6A$ | $N^6$-methyladenosine |
| $m^6Am$ | $N^6$,2'-O-dimethyladenosine |
| $m^6_2A$ | $N^6$,$N^6$-dimethyladenosine |
| $m^6_2Am$ | $N^6$,$N^6$,2'-O-trimethyladenosine |

In one embodiment, the methylated adenosine residue introduced into the 5' untranslated region (UTR) is $N^6$-methyladenosine ($m^6A$). As described above, $m^6A$ is a reversible base modification seen in the 5' UTR of many eukaryotic mRNAs. $m^6A$ residues in the 5' UTR enable eIF4E-independent (i.e., cap-independent) translation of an RNA molecule by preferential binding of eIF3.

Many eukaryotic cellular mRNAs are blocked at their 5'-ends with the 7-methyl-guanosine five-prime cap structure, $m^7GpppX$ (where X is any nucleotide). This structure is involved in several cellular processes including enhanced translational efficiency, splicing, mRNA stability, and RNA nuclear export. The eukaryotic 5' cap is recognized by the cap-binding protein eIF4E.

In carrying out this method of the present invention, the RNA molecule may have an $m^7G$ 5' cap, an $m^7G$ cap analog, or various non-canonical structures, which are well known in the art. Exemplary RNA cap analogs include, but are not limited to, 3'-O-Me-$m^7G$(5')ppp(5')G, $m^7G$(5')ppp(5')G, G(5')ppp(5')G, $m^7G$(5')ppp(5')A, and G(5')ppp(5')A. The following provide a discussion of non-natural cap analogs: Rydzik et at., "Synthetic Dinucleotide mRNA Cap Analogs with Tetraphosphate 5',5' Bridge Containing Methylenebis (Phosphonate) Modification," Org. Biomol. Chem. 7(22): 4763-76 (2009); Kowalska et al., "Synthesis and Characterization of mRNA Cap Analogs Containing Phosphorothioate Substitutions that Bind Tightly to eIF4E and are Resistant to the Decapping Pyrophosphatase DcpS," RNA 14(6):1119-31 (2008); and Ziemniak et al., "Potential Therapeutic Applications of RNA Cap Analogs," Future Med. Chem. 5(10): 1141-72 (2013), which are hereby incorporated by reference in their entirety.

eIF4E is a eukaryotic translation initiation factor involved in directing ribosomes to the cap structure of mRNAs. It is a 24-kD polypeptide that exists as both a free form and as part of the eIF4F pre-initiation complex. Almost all cellular mRNA require eIF4E in order to be translated into protein. The eIF4E polypeptide is the rate-limiting component of the eukaryotic translation apparatus and is involved in the mRNA-ribosome binding step of eukaryotic protein synthesis.

eIF3 is a large multiprotein complex comprising 13 subunits that controls the assembly of the 40s ribosomal subunit on mRNA to promote assembly of the preinitiation complex. eIF3 recognizes $m^6A$ residues in the 5' UTR as well as internal ribosome entry sites (IRES) that may be present in an mRNA molecule.

As used herein, an "internal ribosome entry site" or "IRES" refers to a non-$m^6a$ internal site of mRNA sequence which recruits the ribosome or other translation initiation machinery to enable translation initiation. IRES elements may be present in the 5' UTR of viral and eukaryotic mRNA. Various viral IRES elements are known in the art and include, for example, Picornavirus IRES, Aphthovirus IRES, Hepatitis A IRES, Hepatitis C IRES, and Pestivirus IRES. Exemplary IRES elements present in eukaryotic mRNA include, but are not limited to, fibroblast growth factor (FGF-1 IRES and FGF-2 IRES), platelet-derived growth factor B (PDGF/c-sis IRES), vascular endothelial growth factor (VEGF IRES), insulin-like growth factor 2 (IGF-II IRES), c-myc (c-myc IRES), L-myc (L-myc IRES), immunoglobulin heavy chain binding protein (BiP IRES), and heat shock protein 70 (HSP70 IRES).

In carrying out this and other methods of the present invention, the RNA molecule may lack (i) a 5' cap, (ii) an internal ribosome entry site (IRES), or both (i) and (ii). Alternatively, the RNA molecule may possess (i) a 5' cap, (ii) an internal ribosome entry site (IRES), or both (i) and (ii).

The RNA molecule may further comprise a polyA tail. As used herein, the term "polyA tail" refers to a consecutive sequence of adenylic acids that are normally present at the 3' terminal of eukaryotic mRNA. The polyA tail is involved in stabilization, translation, and transport of mRNA from nucleus to cytoplasm.

Introducing a methylated adenosine residue in a 5' untranslated region of an RNA molecule may be carried out by various means. In one embodiment, introducing a methylated adenosine residue in a 5' untranslated region (UTR) of the RNA molecule is carried out by ligating an RNA molecule comprising a methylated adenosine residue in a 5' untranslated region (UTR) to the RNA molecule to be translated. As used herein, the term "ligating" refers to an enzymatic reaction which catalyzes the joining of two nucleic acid molecules by forming a new chemical bond. An exemplary method of introducing a methylated adenosine residue in a 5' untranslated region (UTR) of an RNA molecule involves ligating an RNA molecule having an $m^6A$ residue to the 5' untranslated region (UTR) of the RNA molecule lacking a methylated adenosine residue in a 5' untranslated region (UTR). This method may involve using a T4 DNA ligase and a bridging DNA oligonucleotide complementary to the RNAs, where the T4 DNA ligase is effective to join the RNA molecules to each other when they are in an RNA:DNA hybrid.

Alternatively, introducing a methylated adenosine residue into a 5' untranslated region (UTR) of an RNA molecule may be carried out by enzymatic methylation. Enzymatic methylation includes the use of a methyltransferase. As used herein, the term "methyltransferase" refers to transferase class enzymes that are able to transfer a methyl group from a donor molecule to an acceptor molecule, e.g., an adenine base of an RNA molecule. This includes, for example and without limitation, methylation enzymes that are engineered or which are fusions of naturally occurring methylation enzymes and their binding partners. Methyltransferases typically use a reactive methyl group bound to sulfur in S-adenosyl methionine (SAM) as the methyl donor. In some embodiments, a methyltransferase described herein is an $m^6A$ methyltransferase. An exemplary $m^6A$ methyltransferase is METTL3 (i.e., MT-A70), which preferentially methylates RNA oligonucleotides containing GGACU and related ribonucleotide sequences. Another example is METTL14, which similarly facilitates methylation at GGACU and related sequences.

Another aspect of the present invention relates to a method for eIF4E-independent translation of an RNA molecule. This method involves providing an RNA molecule to be translated, where the RNA molecule comprises a methylated adenosine residue in a 5' untranslated region (UTR) and a heterologous 5' cap and translating the RNA molecule.

Cellular translation of eukaryotic mRNA involves both cap-dependent and cap-independent mechanisms. Cap-dependent translation requires the binding of an initiation factor, eIF4E, to the cap structure. As described above, eIF4E-independent translation may be mediated by the direct recognition of an $m^6A$ residue in the 5' untranslated region (UTR) of an RNA molecule by the eukaryotic translation initiation factor eIF3. eIF4E-independent translation can also be mediated by IRES structures which may be present in the 5' untranslated region (UTR) of viral or eukaryotic RNA and/or in an internal region of an RNA molecule.

According to one embodiment of this aspect of the invention, the RNA molecule further comprises an internal ribosomal entry site (IRES). In some embodiments, the RNA molecule of the present invention comprises an IRES and is effective to enable the translation of multiple proteins or peptide sequences from a single RNA molecule.

According to an alternative embodiment, the RNA molecule lacks an internal ribosomal entry site (IRES).

In another embodiment, the methylated adenosine residue is $m^6A$. $m^6A$ residues may be present throughout an RNA molecule. For example, an RNA molecule according to the present invention may further comprise $m^6A$ residues (i) in the coding region of the RNA molecule, (ii) in the 3' untranslated region (UTR) of the RNA molecule, or in both (i) and (ii).

Methods of translating RNA molecules include the use of cell-based (i.e., in vivo) and cell-free (i.e., in vitro) expression systems. Translation or expression of a protein can be carried out by introducing a nucleic acid molecule encoding a protein or protein fragment into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted protein coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express a protein encoding sequence in a cell. Primarily, the vector system must be compatible with the host cell used. Host-vector systems include, but are not limited to, the following: microorganisms such as yeast containing yeast expression vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used.

Depending on the vector system and host utilized, any number of suitable transcription and/or translation elements, including constitutive, inducible, and repressible promoters, as well as minimal 5' promoter elements may be used.

The protein-encoding nucleic acid, a promoter molecule of choice, a suitable 3' regulatory region, and if desired, polyadenylation signals and/or a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a protein is inserted into a vector in the sense (i.e., 5→3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct.

Once the isolated nucleic acid molecule encoding the protein has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, New York (1989), which is hereby incorporated by reference in its entirety. Suitable hosts include, but are not limited to, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In some embodiments, translating the RNA molecule is carried out in a cell-free system. Cell-free expression allows for fast synthesis of recombinant proteins and enables protein labeling with modified amino acids, as well as expression of proteins that undergo rapid proteolytic degradation by intracellular proteases. As described above, exemplary cell-free systems comprise cell-free compositions, including cell lysates and extracts. Whole cell extracts may comprise all the macromolecule components needed for translation and post-translational modifications of eukaryotic proteins. As described above, these components include, but are not limited to, regulatory protein factors, ribosomes, and tRNA.

The RNA molecules according to this aspect of the invention may further comprise a sequence motif or aptamer sequence that binds and recruits proteins capable of methylating RNA such that an $m^6A$ is formed in the 5' UTR.

As used herein, the term "sequence motif" refers to a certain nucleotide sequence of at least 2 nucleotides in a larger oligonucleotide sequence. A sequence motif may occur once in an oligonucleotide sequence, or it may occur any number of times. An exemplary sequence motif is an adenosine methylation motif that falls under the general motif DRACH, where D=A, U; R=G; A; H=A, C, U. A broader list is provided in Linder et al., "Single-Nucleotide-Resolution Mapping of $m^6A$ and $m^6Am$ Throughout the Transcriptome," *Nat. Methods.* 12(8):767-72 (2015), which is hereby incorporated by reference in its entirety. Additional motifs such as U-rich motifs may also facilitate the methylation of DRACH motifs in RNA that are expressed in living cells. In one embodiment, the RNA molecule comprises multiple sequence motifs. Each sequence motif may be effective to target an adenosine residue in the 5' UTR of an RNA molecule for methylation by a methyltransferase.

As used herein, the term "aptamer" refers to a nucleic acid molecule that binds specifically to a target. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

The nucleic acid aptamer according to this aspect of the invention may be located in 5' UTR of the RNA molecule and includes a domain for binding to a component of cellular methylation machinery. The aptamer may comprise a plurality of aptamer domains separated by linker regions of suitable length that are effective to prevent steric or folding interference between each domain, allowing each to properly fold and bind to their respective targets. Upon binding between the aptamer and domain to a component of the cellular methylation machinery, the target RNA molecule is effectively methylated at the targeted adenosine residue in the 5' UTR of the RNA molecule.

A further aspect of the present invention relates to a treatment method. This method involves contacting a cell with an RNA molecule comprising a methylated adenosine residue in a 5' untranslated region (UTR) under conditions effective to effect translation of the RNA molecule to treat the cell.

According to one embodiment, this and other treatment methods described herein are effective to treat a cell under a stress or disease condition. Exemplary cell stress conditions may include, without limitation, exposure to a toxin; exposure to chemotherapeutic agents, irradiation, or environmental genotoxic agents such as polycyclic hydrocarbons or ultraviolet (UV) light; exposure of cells to conditions such as glucose starvation, inhibition of protein glycosylation, disturbance of $Ca^{2+}$ homeostasis and oxygen; exposure to elevated temperatures, oxidative stress, or heavy metals; and exposures to a pathological disease state (e.g., diabetes, Parkinson's disease, cardiovascular disease (e.g., myocardial infarction, end-stage heart failure, arrhythmogenic right ventricular dysplasia, and Adriamycin-induced cardiomyopathy), and various cancers (Fulda et al., "Cellular Stress Responses: Cell Survival and Cell Death," *Int. J. Cell Biol.* (2010), which is hereby incorporated by reference in its entirety).

Additional exemplary stress or disease conditions include those of a cell undergoing a viral infection. By impairing cap-dependent ribosome recruitment to host mRNAs, many viruses globally interfere with host mRNA translation, crippling host antiviral responses, and favoring viral protein synthesis. Some viruses directly target degradation of cellular translation factors to prevent ribosome recruitment by host mRNAs. For example, poliovirus (an enterovirus), feline calicivirus, and retroviruses each encode proteases that cleave eIF4G, separating its (amino-terminal) eIF4E-interacting domain from its eIF4A- and eIF3-binding segment, thereby inhibiting cap-dependent protein synthesis in a eukaryotic cell. Vesicular stomatitis virus (VSV), influenza virus, and adenovirus (Ad) decrease eIF4E phosphorylation, resulting in the accumulation of unphosphorylated eIF4E. Other viruses, including encephalomyocarditis virus (EMCV), poliovirus, cricket paralysis virus (CrPV), VSV, Sindbis virus (SINV), Dengue virus (DENV), and reovirus, as well as small DNA viruses such as SV40, impact initiation factors indirectly by, for example, inducing the accumulation of proteins which sequester the cap-binding subunit eIF4E and preventing eIF4F assembly.

In one embodiment of this and other aspects of the present invention, the cell is in a stress or disease condition, where an active amount of eIF4E (i.e., phosphorylated eIF4E) is reduced or absent in the cell compared to the cell in an unstressed or disease-free state.

Various embodiments of the RNA molecules of the present invention are described above and apply in carrying out this and other treatment methods described herein. For example, in one embodiment the methylated adenosine residue is $m^6A$. In another embodiment the RNA molecules lacks (i) a 5' cap, (ii) an internal ribosomal entry site (IRES), or both (i) and (ii). Alternatively, the RNA molecule may further comprise (i) a 5' cap, (ii) an internal ribosomal entry site (IRES), or both (i) and (ii).

In some embodiments, contacting a cell with an RNA molecule involves introducing an RNA molecule into a cell. Suitable methods of introducing RNA molecules into cells are well known in the art and include, but are not limited to, the use of transfection reagents, electroporation, microinjection, or via RNA viruses.

The cell may be a eukaryotic cell. Exemplary eukaryotic cells include a yeast cell, an insect cell, a fungal cell, a plant cell, and an animal cell (e.g., a mammalian cell). Suitable mammalian cells include, for example without limitation, human, non-human primate, cat, dog, sheep, goat, cow, horse, pig, rabbit, and rodent cells.

In certain embodiments of the treatment methods of the present invention, the RNA molecule encodes a therapeutic protein or peptide sequence. The therapeutic protein may be endogenous or heterologous to the cell. The therapeutic protein may be down-regulated in a disease state, a stress state, or during a pathogen infection of a cell.

Treating cells also includes treating the organism in which the cells reside. Thus, by this and the other treatment methods of the present invention, it is contemplated that treatment of a cell includes treatment of a subject in which the cell resides.

Another aspect of the present invention relates to a treatment method. This method involves contacting a cell with a DNA molecule encoding an RNA molecule comprising an adenosine methylation motif in a 5' untranslated region (UTR) under conditions effective for the DNA molecule to be transcribed to produce an RNA molecule comprising an adenosine methylation motif in a 5' untranslated region (UTR) such that the RNA molecule is methylated at the adenosine methylation motif and is translated to treat the cell.

In one embodiment of carrying out this method of the present invention, the DNA molecule encodes an RNA molecule which encodes a therapeutic protein or peptide sequence. The therapeutic protein may be endogenous or heterologous to the cell. The therapeutic protein may be down-regulated in a disease state, a stress state, or during a pathogen infection in a cell. The DNA molecule may be a synthetic DNA molecule or a naturally-occurring DNA molecule.

As used herein, the term "synthetic DNA molecule" refers to an engineered or non-naturally-occurring DNA molecule (e.g., a DNA molecule comprising a heterologous sequence or modification). In one embodiment, the DNA molecule is a plasmid. The plasmid may encode one or more methylation motifs in the 5' untranslated region (UTR) of the transcribed RNA molecule. A "naturally-occurring DNA molecule" refers to a DNA molecule consisting of a sequence that occurs in nature.

In one embodiment, the DNA molecule does not encode (i) a 5' cap, (ii) an internal ribosomal entry site (IRES), or both (i) and (ii). Alternatively, the DNA molecule may encode (i) a 5' cap, (ii) an internal ribosomal entry site (IRES), or both (i) and (ii).

In some embodiments, the methylated adenosine is $m^6A$. As described above, $m^6A$ residues in the 5' untranslated (UTR) region of RNA are effective to mediate eIF4E-independent translation of an RNA molecule.

A further aspect of the present invention relates to a treatment method. This method involves contacting a cell with an agent capable of recruiting methylation machinery to an RNA molecule comprising an adenosine residue in a 5' untranslated region (UTR) under conditions effective to methylate the adenosine residue such that the RNA molecule is translated to treat the cell.

As described above, "cell" may include a eukaryotic cell, including but not limited to human, non-human primate, cat, dog, sheep, goat, cow, horse, pig, rabbit, and rodent cells.

In one embodiment of this aspect of the present invention, the agent is an aptamer. As described above, the term "aptamer" refers to a nucleic acid molecule that binds specifically to a target. The nucleic acid aptamer according to this aspect of the invention may include a domain for binding to a component of cellular methylation machinery and/or a domain for binding to an RNA molecule at or near the 5' UTR. The aptamer may bind specifically to a target RNA molecule by hybridization (e.g., Watson-Crick base-pairing). Thus, the aptamer may comprise a nucleotide sequence that is sufficiently complementary to the target RNA molecule so as to hybridize under appropriate conditions with a target RNA molecule that is physiologically found within a cell or within a biological sample. Upon hybridization between the aptamer and the target RNA and the binding of the first domain to a component of the cellular methylation machinery, the target RNA molecule is effectively methylated at the adenosine residue.

In some embodiments, the agent is a sequence element. For example, the sequence element may be an RNA sequence element that recruits an artificial or naturally-occurring fusion protein that induces methylation. Suitable sequence elements include an adenosine methylation motif. The sequence element can be the "MS2" hairpin sequence or the BoxB hairpin sequence that recruits proteins tagged with the MS2 coat protein (MCP) or the lamdaN peptide, respectively. These proteins are recruited to the sequence element to methylate adenosine residues in a suitable sequence motif.

The RNA molecules according to this aspect of the invention may lack (i) a 5' cap, (ii) an internal ribosome entry site (IRES), or both (i) and (ii). Alternatively, the RNA molecules may include (i) a 5' cap, (ii) an internal ribosome entry site (IRES), or both (i) and (ii).

Another aspect of the present invention relates to a method of enhancing translation ability of an RNA molecule in a cell. This method involves identifying a cell comprising an RNA molecule that could benefit from eIF4E-independent translation and contacting the cell with an agent capable of forming a methylated adenosine residue in a 5' untranslated region (UTR) of the RNA molecule to enhance translation ability of the RNA molecule in the cell.

In carrying out this method of the present invention, the cell may be identified as being under stress or subject to disease. Or, the cell may be identified as a cell where translation mediated by eIF4E is reduced, e.g., below a normal or expected level. Various cellular stress and disease conditions are described in detail above.

The RNA molecule may be endogenous to the cell or heterologous to the cell. Similarly, the RNA molecule may encode an endogenous protein that is not expressed or undergoes decreased expression when the cell is under stress or subject to disease or where translation mediated by eIF4E is reduced. Alternatively, the RNA molecule may encode a chimeric or heterologous protein that may be effective to treat the cell.

As described above, the RNA molecule may be synthetic.

In on embodiment, the methylated adenosine residue is $m^6A$.

The RNA molecules according to this aspect of the invention may lack (i) a 5' cap, (ii) an internal ribosome entry site (IRES), or both (i) and (ii). Alternatively, the RNA molecules of the present invention may further comprise (i) a 5' cap, (ii) an internal ribosome entry site (IRES), or both (i) and (ii).

As described above, the agent may be a sequence element or an aptamer.

In some embodiments, the agent is a guide RNA. As used herein the term "guide RNA" means a specific RNA moiety which recruits and directs the nuclease activity of a Cas9 nuclease. The guide RNA may recruit Cas9, Cas9-fusion proteins, and related proteins to specific sites in a target RNA. In one embodiment, the agent is a guide RNA which is effective to direct the modification of a 5' UTR to include an adenosine methylation recognition sequence.

A further aspect of the present invention relates to a kit. The kit includes a DNA molecule encoding an RNA molecule comprising an adenosine methylation motif in a 5' untranslated region (UTR); reagents for transcribing the RNA molecule; and reagents for methylating the RNA molecule.

Another aspect of the present invention relates to a kit that includes a DNA molecule encoding an RNA molecule, reagents for transcribing the molecule, and $m^6A$ nucleotides in a form suitable for incorporation into synthesized RNA.

According to one embodiment, this kit is used to carry out a method of making an RNA molecule comprising one or more $m^6A$ residues (in the 5' UTR). Specifically, in vitro transcription reactions in a medium containing CTP, GTP, UTP, and a mix of $m^6ATP$ and ATP (or all $m^6ATP$) permit transcription of RNA that has $m^6A$ throughout its sequence, including in the 5' UTR. Such a molecule then becomes very competent to translate in an eIF4E-independent way, or can allow a new mode of translation on top of the translation modes that it already has, e.g., cap-mediated; IRES mediated; or $m^6A$ mediated.

A further aspect of the present invention relates to an mRNA molecule comprising a methylated adenosine residue in a 5' untranslated region (UTR) and a 5' cap.

According to one embodiment, the mRNA molecule further comprises an internal ribosome entry site ("IRES") motif The mRNA molecule according to this aspect of the present invention may encode for a full-length protein or a protein fragment.

In one embodiment of the mRNA molecule, the 5' cap is heterologous to the mRNA molecule. In other words, the 5' cap is not normally associated with the mRNA molecule in nature.

The mRNA molecule according to this aspect of the present invention may have one or more than one methylated adenosine residues in the 5' untranslated region (UTR). For example, the mRNA molecule may have 1, 2, 3, 4, 5, 6, 7, or more methylated adenosine residues in the 5' untranslated region (UTR).

These aspects of the present invention are further illustrated by the examples below.

EXAMPLES

The following examples are provided to illustrate embodiments of the present invention, but they are by no means intended to limit its scope.

Materials and Methods for Examples 1-8

In Vitro Translation

In vitro translation assays were performed using HeLa cell extracts (One-Step Human IVT Kit, Thermo Scientific). Equal amounts of RNA were used for each reaction (100 ng RNA per reaction, approximately 30 nM per reaction), and all reactions within each experiment were performed in equal volumes. Multiple different batches of HeLa extracts and mRNA preparations were used to ensure that the translation-promoting effect of $m^6A$ is not due to a specific lot of extract or batch of synthesized mRNA. However, this also contributes to inter-experiment variability. Reactions were performed at 30° C. for 30 minutes and were stopped by the addition of 200 μM cycloheximide and placed on ice. 1 μl of each reaction was then used for luminescence analysis (see below). The remaining reaction volume was used for RNA isolation with TRIzol (Invitrogen) or Qiagen RNeasy kits according to the manufacturer's instructions. cDNA synthesis was then performed using Superscript III reverse transcriptase (Invitrogen) and random hexamers. Following treatment with RNase H, cDNA was then used for RT-qPCR analysis to ensure that differences in mRNA levels across samples did not account for the observed changes in protein production. Statistical analysis of luciferase activity measurements was performed using Student's t-test and a p-value threshold of 0.01.

Luciferase Activity Measurements

Luciferase expression was measured using the One-Glo luciferase assay kit (Promega) according to the manufacturer's instructions. Luminescence measurements were performed on a Molecular Devices Spectramax L microplate reader using the SoftMax Pro software program.

eIF3a PAR-iCLIP eIF3a PAR-iCLIP was performed using HEK293T cells as described previously (Huppertz et al., "iCLIP: Protein-RNA Interactions at Nucleotide Resolution," Methods 65:274-287 (2014), which is hereby incorporated by reference in its entirety) with some adjustments. 10 million cells were incubated with 100 mM 4SU for 8 hours. Media was then discarded, and cells were placed on ice and irradiated with 365 nm UV light using a Stratalinker UV crosslinker (Stratagene) with 150 mJ/cm$^2$. Cells were scraped in ice-cold 1× PBS and collected by centrifugation at 200×g for 10 min at 4° C. Cell pellets were suspended in 200 μl of 1% SDS, 10 mM DTT and 1× protease inhibitors (cOmplete™ mini EDTA-free, Roche). The lysate was then passed through an 18G needle 10 times to improve cell lysis and shearing of DNA. SDS was neutralized by diluting the lysate to 2 ml using RIPA buffer without SDS. The remainder of the protocol was performed as described (Huppertz et al., "iCLIP: Protein-RNA Interactions at Nucleotide Resolution," Methods 65:274-287 (2014), which is hereby incorporated by reference in its entirety) using rabbit anti-eIF3a (Abcam).

Cell Lines and Antibodies

HeLa cells, HEK293T cells, and MEF cells were maintained in Dulbecco's modified Eagle's medium (DMEM) with 10% fetal bovine serum (FBS). Antibodies used for western blot analysis were as follows: HSP70 (SPA-810) was purchased from Stressgen; anti-FTO (597-Fto) from Phosphosolutions or Abcam; RPS6 from Genetex; goat anti-GFP from Santa Cruz Biotechnology; mouse anti-β-actin from Genscript; rabbit anti-GAPDH, Rabbit anti-YTHDF1 (Ptglabs 17479-1-AP), Rabbit anti-YTHDF2 (Ptglabs 24744-1-AP), Rabbit anti-YTHDF3 (Ptglabs 25537-1-AP), Rabbit anti-YTHDC1 (Ptglabs 14392-1-AP), and Rabbit anti-YTHDC2 (Novus 17479-1-AP) from Abcam. Rabbit anti-m$^6$A was from Synaptic Systems.

Assembly and Analysis of Ribosomal Complexes

Expression vectors for eIF1 and eIF1A (Pestova et al., "Eukaryotic Ribosomes Require Initiation Factors 1 and 1A to Locate Initiation Codons," Nature 394:854-859 (1998), which is hereby incorporated by reference in its entirety), eIF4A and eIF4B (Pestova et al., "Canonical Eukaryotic Initiation Factors Determine Initiation of Translation by Internal Ribosomal Entry," Mol. Cell Biol. 16:6859-6869 (1996), which is hereby incorporated by reference in its entirety), eIF4E (Volpon et al., "Cap-Free Structure of eIF4E Suggests a Basis for Conformational Regulation by its Ligands," EMBO J. 25:5138-5149 (2006), which is hereby incorporated by reference in its entirety), and E. coli methionyl tRNA synthetase (Lomakin et al., "The Fidelity of Translation Initiation; Reciprocal Activities of eIF1, IF3 and YciH," EMBO J. 25:196-210 (2006), which is hereby incorporated by reference in its entirety), as well as transcription vectors for MVHC-STOP mRNA (comprising the 54 nt-long 5' UTR of rabbit β-globin mRNA starting with two extra Gs, the coding sequence for an MVHC tetrapeptide, a UAA stop codon, and an approximately150 nucleotide 3'UTR consisting of the natural β-globin coding sequence) (Skabkin et al., "Reinitiation and Other Unconventional Posttermination Events During Eukaryotic Translation," Mol. Cell 51:249-264 (2013), which is hereby incorporated by reference in its entirety) and tRNA$_i^{Met}$ (Pestova et al., "Preparation and Activity of Synthetic Unmodified Mammalian tRNAi(Met) in Initiation of Translation In Vitro," RNA 7:1496-1505 (2001), which is hereby incorporated by reference in its entirety) have been described. The transcription vector for β-globin-2AUG mRNA was made by inserting an appropriate DNA fragment flanked by a T7 promoter and a HindIII restriction site into pUC57 (GenScript Corp.). Native 40S and 60S ribosomal subunits eIF2, eIF3, eIF4F, eIF5B, eEF1H, eEF2, and total aa-tRNA synthetases, and recombinant eIF1, eIF1A, eIF4A, eIF4B, eIF5, and E. coli methionyl tRNA synthetase were purified as described (Lomakin et al., "The Fidelity of Translation Initiation; Reciprocal Activities of eIF1, IF3 and YciH," EMBO J. 25:196-210 (2006) and Pisarev et al., "Assembly and Analysis of Eukaryotic Translation Initiation Complexes," Methods Enzymol. 430:147-177 (2007), which are hereby incorporated by reference in their entirety). mRNAs and tRNA$_i^{Met}$ were transcribed using T7 RNA polymerase. Transcribed mRNAs were capped using the T7 mScript Standard mRNA Production System (Cellscript, Madison, Wis., USA). In vitro transcribed tRNA$_i^{Met}$ and elongator tRNAs were aminoacylated using E. coli methionyl tRNA synthetase and native total tRNA synthetases, respectively, as described (Pisarev et al., "Assembly and Analysis of Eukaryotic Translation Initiation Complexes," Methods Enzymol. 430:147-177 (2007), which is hereby incorporated by reference in its entirety).

48S initiation complexes were assembled and analyzed by toe-printing essentially as described (Pisarev et al., "Assembly and Analysis of Eukaryotic Translation Initiation Complexes," Methods Enzymol. 430:147-177 (2007), which is hereby incorporated by reference in its entirety). Briefly, 60 nM mRNA was incubated with 40S subunits (90 nM), Met-tRNA$_i^{Met}$ (150 nM), and different combinations of eIF1 (450 nM), eIF1A (450 nM), eIF2 (160 nM), eIF3 (150 nM), eIF4A (350 nM), eIF4B(350 nM), and eIF4F (150 nM) in 20 μl reaction mixtures containing buffer (20 mM Tris-HCl [pH 7.5], 100 mM KAc, 2.5 mM MgCl$_2$, 0.25 mM spermidine and 2 mM DTT) supplemented with 0.8 mM ATP and 0.4 mM GTP for 15 min at 37° C. Assembled 48S complexes were then incubated with 120 nM 60S subunits, 300 nM eIF5 and 150 nM eIF5B for 10 min at 37° C. to allow formation of 80S initiation complexes. To form pre-termination complexes, 80S complexes were supplemented with 150 nM eEF1H, 150 nM eEF2 and appropriately aminoacylated native total tRNA (~200 nM each) and incubated for 10 min at 37° C. After incubation, the assembled complexes were analyzed by primer extension using AMV reverse transcriptase and a [$^{32}$P]-labeled primer complementary to nucleotides 197-214 of wt β-globin mRNA. The resulting cDNAs were resolved by electrophoresis on a 6% acrylamide sequencing gel followed by autoradiography. The toe-print positions were determined by comparison with a DNA sequence obtained with the same primer.

Translation Efficiency (TE) Analysis

Ribosome profiling data from METTL3-depleted cells and Mettl3 knockout cells was previously described (Wang et al., "N(6)-Methyladenosine Modulates Messenger RNA Translation Efficiency," Cell 161:1388-1399 (2015), which is hereby incorporated by reference in its entirety). TE measurements were analyzed for mRNAs containing m$^6$A within various regions of the transcript as identified by single nucleotide-resolution m$^6$A mapping (Linder et al., "Single-Nucleotide-Resolution Mapping of m$^6$A and m$^6$Am Throughout the Transcriptome," Nat. Methods 12(8):767-72 (2015), which is hereby incorporated by reference in its entirety). Cumulative distribution plots were generated for data visualization, and statistical analysis was done using the Mann-Whitney U test with a P-value cutoff of 0.05.

Heat Shock Induction of Hsp70

MEF cells with Fto knockdown or overexpression were incubated overnight and were 90% confluent prior to heat shock treatment. After incubation in a 42° C. water bath for 1 hour, cells recovered in an incubator at 37° C. and collected at the indicated time points.

Polysome Profiling

Sucrose solutions were prepared in polysome buffer (10 mM HEPES, pH 7.4, 100 mM KCl, 5 mM $MgCl_2$, 100 µg/ml of cycloheximide). A 15-45% (w/v) sucrose density gradients were prepared in SW41 ultracentrifuge tubes (Fisher) using a BioComp Gradient Master (BioComp Instruments). Cells with or without heat shock stress were treated with cycloheximide (100 µg/ml) for 3 minutes at 37° C. and lysed in an ice-cold polysome buffer containing 2% Triton™ X-100. 500 µl supernatant of the cell lysate was loaded onto gradients, followed by centrifugation at 38,000 rpm at 4° C. in a SW41 rotor for 2 h 28 min. Gradients were fractionated through Isco fractionation system and absorbance values at 254 nm were continually monitored.

Real-Time Quantitative PCR

Total RNA from whole cell lysate was isolated using TRIzol reagent (Invitrogen). RNA from fractions with spiked-in luciferase mRNA was extracted by TRIzol LS reagent (Invitrogen). Reverse transcription was performed using High Capacity cDNA Reverse Transcription Kit (Invitrogen). For HSP70-related experiments, Real-time PCR analysis was conducted with Power SYBR Green PCR Master Mix (Applied Biosystems). The reaction was performed on a LightCycler 480 Real-Time PCR System (Roche Applied Science). For luciferase in vitro translation and eIF3 pull-down experiments, qPCR was done using iQ SYBR Green Supermix (Bio-Rad) and an Eppendorf Mastercycler ep realplex thermocycler. Quantification for eIF3 target RNA immunoprecipitation was performed by calculating the Ct values of target RNAs in input and IP samples relative to GAPDH Ct values. Then IP/Input was computed for these values for each sample to determine target RNA enrichment in the IP samples. Primers used to amplify each target are as follows:

```
Gapdh:
Fwd
                                       (SEQ ID NO: 14)
5'-CAAGGAGTAAGAAACCCTGGAC-3', Rev
                                       (SEQ ID NO: 15)
5'-GGATGGAAATTGTGAGGGAGAT-3', Hsp70:
Fwd
                                       (SEQ ID NO: 16)
5'-TGGTGCAGTCCGACATGAAG-3', Rev
                                       (SEQ ID NO: 17)
5'-GCTGAGAGTCGTTGAAGTAGGC-3', Fluc:
Fwd
                                       (SEQ ID NO: 18)
5'-ATCCGGAAGCGACCAACGCC-3', Rev
                                       (SEQ ID NO: 19)
5'-GTCGGGAAGACCTGCCACGC-3', pGL4.34 Luc:
Fwd
                                       (SEQ ID NO: 20)
5'-TTCGTGAGCAAGAAAGGGCT-3',
```

```
Rev
                                       (SEQ ID NO: 21)
5'-AGTCGTACTCGTTGAAGCCG-3',

GAPDH:
Fwd
                                       (SEQ ID NO: 22)
5'-AAATCAAGTGGGGCGATGCT-3',

Rev
                                       (SEQ ID NO: 23)
5'-CAAATGAGCCCCAGCCTTCT-3',

SETD1A:
Fwd
                                       (SEQ ID NO: 24)
5'-AGCGGGCTATTCTCTCACTTG-3',

Rev
                                       (SEQ ID NO: 25)
5'-GCTTTGCTTCTCTTCCCCGT-3',

ITPRIPL2:
Fwd
                                       (SEQ ID NO: 26)
5'-AACACTTGAGCTGGGAGAGG-3',

Rev
                                       (SEQ ID NO: 27)
5'-GAAGACGCGTAGATTGAGGGT-3',

PNMA1:
Fwd
                                       (SEQ ID NO: 28)
5'-CTGGCTAGTCTCCCAAACGG-3',

Rev
                                       (SEQ ID NO: 29)
5'-CATCTTGCGTCTGGGTCTGG-3',

BMP6:
Fwd
                                       (SEQ ID NO: 30)
5'-GAGGGCCAGGAAGGGGAA-3',

Rev
                                       (SEQ ID NO: 31)
5'-CGTGGAGCGGCGGAG-3',
```

In Vitro Transcription

In vitro transcription was performed using either the T7 Flash or Durascribe transcription kit (Epicentre) for making uncapped mRNAs or the mMessage mMachine SP6 transcription kit (Ambion) for making capped mRNAs. The luciferase mRNA sequence used for in vitro translation assays was amplified from the pGL4.34 [luc2P/SRF-RE/Hygro] vector (Promega). Unless otherwise specified, mRNAs were synthesized to contain 50% $m^6A$ using $N^6$-methyladenosine 5' triphosphate. Synthesis of mRNAs with other modifications was performed by the addition of 50% of the indicated modified nucleotide: $N^1$-methyladenosine 5' triphosphate (TriLink), 2'-O-methyladenosine 5' triphosphate (TriLink), $N^6$-propargyladenosine 5' triphosphate (Jena Biosciences), 5-methyladenosine 5' triphosphate (TriLink), pseudouridine triphosphate (TriLink). In vitro transcription was stopped by addition of DNaseI and incubation for 20 minutes at 37° C. mRNAs were then purified using a Bio-Spin RNA purification column (BioRad). For mRNAs with a single 5' end A or $m^6A$, in vitro transcription was carried out using 20 mM adenosine 5'-monophosphate or $N^6$-methyladenosine 5'-monophosphate and 0.5 mM ATP, and using the T7 phi 2.5 promoter sequence (5'-TAATACGACTCACTATTA-3' (SEQ ID NO:32)) (Huang et al., "Systemic and Integrative Analysis of Large Gene Lists Using DAVID Bioinformatics Resources," *Nat. Protoc.*

Figure 2A:
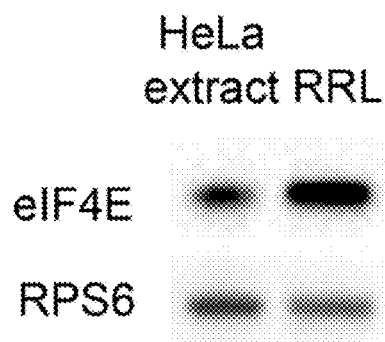
FIGS. 2A-2H show that cap-independent translation is mediated by m$^6$A (related to FIGS. 3 and 4).
Figure 2B:
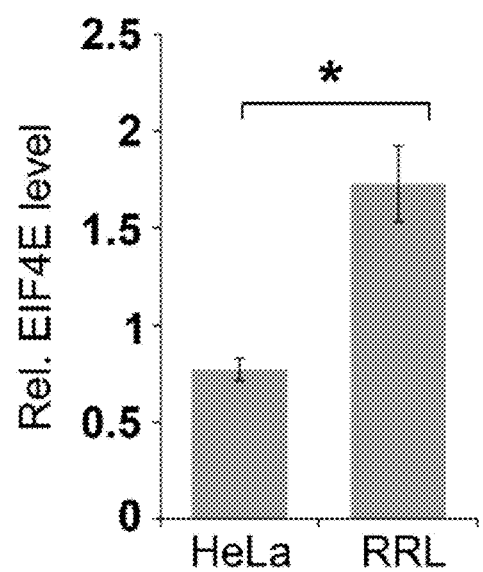
Figure 2C:
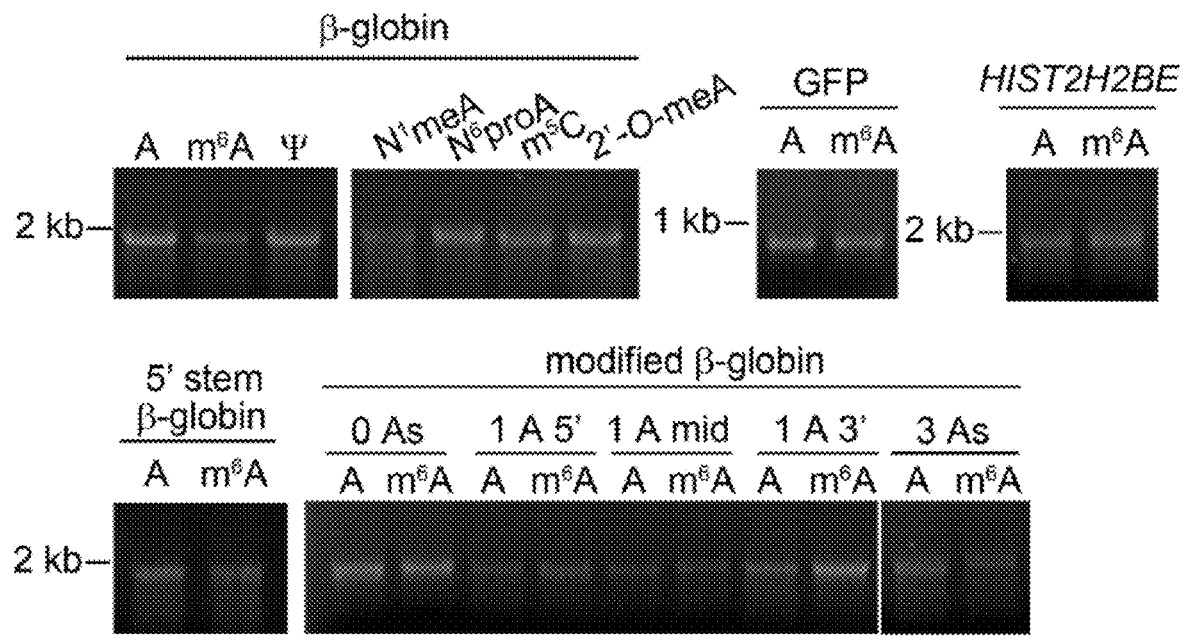
Figure 2D:
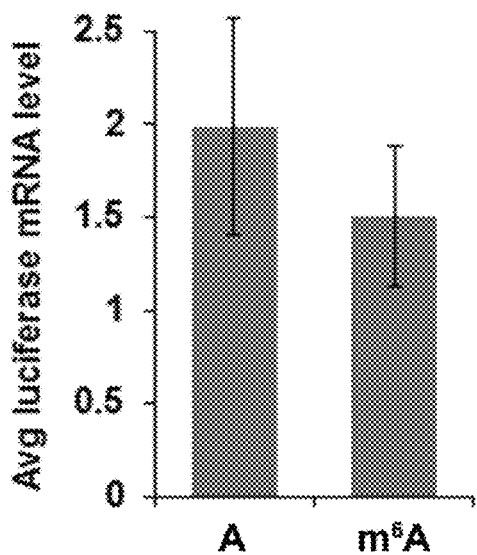
Figure 2E:
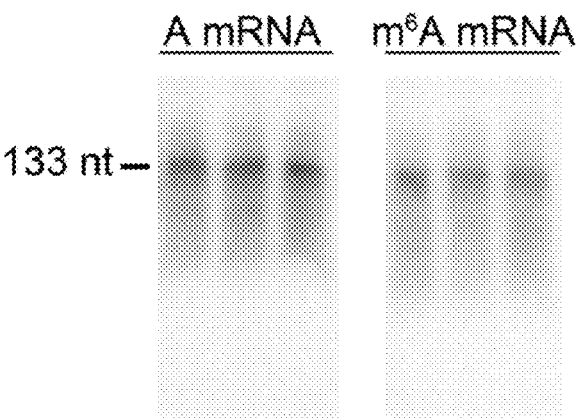

4:44-57 (2009), which is hereby incorporated by reference in its entirety). Of note, the T7 promoter incorporates both methylated (m⁶AMP) and unmethylated (ATP) adenosines at the 5' ends of transcripts when using this promoter sequence; thus, the m⁶A-containing reporter mRNA synthesized with this method (FIG. 2E) does not have m⁶A incorporated in all transcripts. As a result, lower luciferase activity measurements are seen with this reporter than with other m⁶A-containing reporter mRNAs in FIG. 2.

5' UTR Sequences

The various 5'UTR sequences of the mRNAs used for in vitro translation assays are listed below. Although different 5'UTRs showed variability in the degree of cap-dependent translation for both methylated and unmethylated mRNAs, the presence of m⁶A did not have a consistent enhancing or suppressing effect on this mode of translation. Conversely, the effect of m⁶A was consistent and robust on cap-independent translation, regardless of the 5' UTR sequence used.

pGL4.34 5' UTR (FIGS. 2A, 2C):
(SEQ ID NO: 33)
5'-GGAAGCUCGACUUCCAGCUUGGCAAUCCGGUACUGUUGGUAAAG

CCACC-3'

β-globin (FIGS. 2B, 2D, S1, and FIG. 3D):
(SEQ ID NO: 34)
5'-GACACUUGCUUUUGACACAACUGUGUUUACUUGCAAUCCCCAA

AACAGACAGA-3'

β-globin 3 As (FIG. 2D):
(SEQ ID NO: 35)
5'-GACUCUUGCUUUUGCCUCUUCUGUGUUGCUUGACUUCCCCUUG

UUGAC-3'

β-globin 1 A 5' end (FIG. 2D):
(SEQ ID NO: 36)
5'-GACUCUUGCUUUUGCCUCUUCUGUGUUGCUUGCCUUCCCCUUG

UCUGC-3'

β-globin 1 A mid (FIG. 2D, FIG. S2F):
(SEQ ID NO: 37)
5'-GGCUCUUGCUUUUGCCUCUUCUGUGUGACUUGCCUUCCCCUUG

UCUGC-3'

β-globin 1 A 3' end (FIG. 2D):
(SEQ ID NO: 38)
5'-GGCUCUUGCUUUUGCCUCUUCUGUGUUGCUUGCCUUCCCCUUG

UUGAC-3'

β-globin 0 As (FIG. 2D):
(SEQ ID NO: 39)
5'-GGCUCUUGCUUUUGCCUCUUCUGUGUUGCUUGCCUUCCCCUUG

UCUGC-3'

HIST2H2BE (FIG. 2E):
(SEQ ID NO: 40)
5'-ACUUCUUUUCUUGGCUAAGCCGCGUUUGUACUGUGUCUUACC-3'

β-globin hairpin (FIG. 3D):
(SEQ ID NO: 41)
5'-GGGCCCCGCCCGGUGUCGGGCGGGCCCGACACUUGCUUUUGAC

ACAACUGUGUUUACUUGCAAUCCCCCAAAACAGACAGA-3'

β-globin 1 A mid UAC (FIG. S2F):
(SEQ ID NO: 42)
5'-GGCUCUUGCUUUUGCCUCUUCUGUGUUACUUGCCUUCCCCUUG

UCUGC-3'

β-globin 1 A mid CAG FIG. S2F):
(SEQ ID NO: 43)
5'-GGCUCUUGCUUUUGCCUCUUCUGUGUCAGUUGCCUUCCCCUUG

UCUGC-3'

The 5' UTR sequences use for in vitro ribosome complex assembly are as follows:
β-globin 2 AUG (FIG. 3A):
(SEQ ID NO: 44)
5'-GACACUUGCUUUUAGAAUGGACAACUGUGUUUACUUGCAAUCCC

CCAAAACAGACUGCAUCUGUCCAGUGAGGAGAAGUCUGCGGAGAAUG

G-3'

β-globin (FIG. 1A-C):
(SEQ ID NO: 45)
5'-GGACACUUGCUUUUGACACAACUGUGUUUACUUGCAAUCCCCCA

AAACAGACAGA-3'

RNA Decay Analysis in HeLa Lysates

[³²P]-CTP-labeled mRNAs encoding a short FLAG peptide were synthesized by in vitro transcription using the Epicentre T7 Flash kit and either 100% ATP or 50% ATP/50% N⁶-meATP. mRNAs were purified using Bio-spin columns (Bio-Rad), and one microliter of mRNA was added to HeLa cell extracts (One-Step Human IVT Kit, Promega) and incubated at 30° C. for 30 minutes, followed by Trizol extraction. mRNAs were then separated on a 10% TBE-Urea gel and transferred to a nylon membrane. Radioactively labeled mRNA was detected with a phosphor screen and quantified using a PhospholImager.

Hsp70 Pulldown and m⁶A Immunoblotting

To isolate endogenous Hsp70 mRNA, 400 pmol of biotin-labeled probe (5'-TTCATAACATATCTCTGTCTCTT-3' (SEQ ID NO:46)) was incubated with 1 ml of M-280 Streptavidin Dynabeads (Life Technologies) in 1× B & W buffer (5 mM Tris-HCL pH 7.5, 0.5 mM EDTA and 1 M NaCl) at 4° C. for 1 hour. 2 mg total RNA was denatured at 75° C. for 2 minutes and added to the pre-treated Dynabeads for a further 2 hour incubation in 1× B & W buffer at 4° C. Captured RNA was eluted by heating beads 2 minutes at 90° C. in 10 mM EDTA with 95% formamide followed by Trizol LS isolation. Isolated RNA was quantified using NanoDrop ND-1000 UV-Vis Spectrophotometer and equal amounts were mixed with 2× RNA Loading Dye (Thermo Scientific) and denatured for 3 minutes at 70° C. In vitro transcribed mRNA containing 50% N⁶-methyladenosine or 100% adenosine was used as positive and negative controls, respectively. These mRNAs were the corresponding 5'UTR sequence of mouse Hsp70. Samples were then run on a formaldehyde denaturing agarose gel and transferred to a positively charged nylon membrane by siphonage in transfer buffer (10 mM NaOH, 3 M NaCl) overnight at room temperature. After transfer, the membrane was washed 5 min in 2× SSC buffer and RNA was UV crosslinked to the membrane. Membrane was blocked for 1 hour in PBST containing 5% non-fat milk and 0.1% Tween™-20, followed by incubation with anti-m⁶A antibody (1:1000 dilution) overnight at 4° C. After extensive washing with 0.1% PBST 3 times, the membrane was incubated with HRP-conjugated anti-rabbit IgG (1:5000 dilution) for 1 hour. Membrane was visualized using enhanced chemiluminescence (ECL Plus, GE Healthcare).

Lentivirus Knockdown and Establishment of Stable Cell Lines

The Fto knockdown cell line was established using the Lenti-X shRNA Expression System. The Fto target sequence (5'-GCTGAGGCAGTTCTGGTTTCA-3' (SEQ ID NO:47)) and scramble control (5'-CCTAAGGT-TAAGTCGCCCTCG-3' (SEQ ID NO:48)) were inserted into the pRSI9-U6-(sh)-UbiC-TagRFP-2A-Puro empty vector (Cellecta, Calif.). shRNA lentivirus was packaged by Lenti-X 293T cells according to the manufacturer's instructions. MEF cells were infected by the shRNA lentivirus for 48 hours before selection by puromycin at a dose of 1 µg/ml. Because the lentiviral-based overexpression often leads to a slightly stressed cellular state compared to stable cell selection, slight increases in Hsp70 levels were often observed following massive protein overexpression. Thus, there is a mild increase in the basal translation rate of Hsp70 following GFP overexpression compared to stable cells expressing a scramble control shRNA (FIGS. 6D, 6F).

UV Crosslinking of RNA Probes $^{32}$P-CTP labeled RNA probes were synthesized by in vitro transcription using MAXIscript® T7 Kit (Life Technologies). Probe sequences used were as follows: 5'-GGGACU$_{(14)}$-3' (SEQ ID NO:49), 5'-GGUACU$_{(14)}$-3' (SEQ ID NO:50), 5'-GGCAGU$_{(15)}$-3' (SEQ ID NO:51), 5'-GGGACU$_{(13)}$-3' (SEQ ID NO:52), and 5'-GU$_{(5)}$ GGACU$_{(7)}$-3' (SEQ ID NO:53). Probes were purified using RNA Clean & Concentrator™5 columns (Zymo Research), and A- and m$^6$A-containing probes were ensured to have the same specific activity before performing the crosslinking assays. For identification of m$^6$A RNA binding proteins, protein was first preincubated in 1× Binding buffer (10 mM HEPES pH 7.4, 140 mM KCl, 10 mM NaCl, 1 mM MgCl$_2$, 0.01% NP-40, 5% Glycerol and poly-uridylic acid (100 nM, average size 150 nucleotides)) for 15 minutes at 25° C. and then with either m$^6$A- or A-radiolabeled RNA probes (105 cpm, 1 nM) for another 15 minutes at 25° C. Equal amounts of protein were used for m$^6$A- or A-containing RNA reactions. Binding reactions were then irradiated twice with UV at 254 nm (150 kJ/cm$^2$) on a prechilled parafilm sheet on ice. Unbound RNA was digested with 50 Units of RNase If (NEB) at 37° C. for 30 minutes. Samples were then mixed with NuPAGE LDS Sample Buffer (4×), heated at 95° C. for 5 minutes, and electrophoresed on 4-12% NuPAGE Novex Bis-Tris Protein Gels in 1× MES-SDS buffer. To visualize proteins, gel was stained with silver using Silver stain kit (Pierce) and documented on a Biorad gel imager. Radioactive signal from protein-linked, RNase-protected RNA was captured on a phosphor screen and documented using a phosphor imager.

eIF3 Protein/RNA Immunoprecipitation

HEK293T cells were transfected with plasmids expressing GFP or FLAG-tagged Fto using FuGene HD (Promega). 24 hours later, cells were washed once with ice cold 1×PBS and UV crosslinked in a Stratalinker at 254 nm (150 kJ/cm$^2$). Cells were then collected and spun down 500×g, 2.5 minutes, 4° C. Pellets were collected and cells were lysed by addition of lysis buffer (50 mM Tris HCl, pH 7.4, 100 mM NaCl, 1% NP-40, 0.1% SDS, 0.5% sodium deoxycholate, Roche Protease Inhibitor added fresh) and then passed through a 21G needle ten times while maintaining the lysates on ice. 2 µl of Turbo DNase and 10 µl of RNase I (1:500 dilution in PBS) were then added, and lysates were incubated 3 minutes at 37° C. while shaking. Lysates were then placed back on ice and passed ten more times through a 21G needle and incubated 10 min on ice. Finally, lysates were clarified by centrifugation at 21,000×g for 10 minutes. 10% of each supernatant was saved for RNA isolation from the input sample and the remainder was used for eIF3 immunoprecipitation.

For immunoprecipitation, 5 µg of rabbit anti-eIF3A antibody (Abcam) was incubated with 25 µl of Protein A/G magnetic beads (Pierce Biotechnology) for 45 minutes at room temperature, rotating. Beads were then washed 3 times in lysis buffer and lysates were added. Immunoprecipitation was performed for 1 hour at room temperature and 1 hour at 4° C. or overnight at 4° C. Beads were then washed 5 times in high salt buffer (50 mM Tris HCl, pH 7.4, 1 M NaCl, 1 mM EDTA, 1% NP-40, 0.1% SDS, 0.5% sodium deoxycholate) and RNA was eluted following 20 min incubation with Proteinase K at 37° C. and subsequent addition of Trizol LS for isolation of RNA. cDNA synthesis from IP and input RNA samples was performed using random hexamers and Superscript III reverse transcriptase according to the manufacturer's instructions (Life Technologies).

RNA Crosslinking and Immunoprecipitation

400 µg of Hela lysate (One-Step Human IVT Kit, Thermo Scientific) was crosslinked in 1× Binding buffer to A or m$^6$A RNA probes (5'-GGGACU$_{(14)}$-3' (SEQ ID NO:54), 3*10$^5$ cpm) in a 40 µl crosslinking reaction as above. Crosslinking reactions were diluted to 500 µl with ice-cold 1× PBS containing EDTA-free protease inhibitor (Roche). 2 µg of IgG control or anti-eIF3a, 3b, and ABCF1 were added and incubated at 4° C. for 12 hours on a shaker. Antigen-antibody complexes were bound to Protein AG beads (Thermo Scientific) and washed 3 times with WB500 buffer (20 mM HEPES pH 7.4, 500 mM NaCl, 0.1% NP-40) and 2 times with WB150 buffer (20 mM HEPES pH 7.4, 150 mM NaCl, 0.1% NP-40) at room temperature. Beads were suspended in 1× Binding buffer and subjected to RNase I digestion. Samples were denatured with NuPAGE® LDS Sample Buffer (4×), heated at 95° C. for 5 minutes, and electrophoresed on 4-12% NuPAGE® Novex® Bis-Tris Protein Gels in 1× MES-SDS buffer. Proteins were transferred to pure nitrocellulose membrane in 1× transfer buffer containing 20% methanol by wet-transfer method. Membrane was washed twice in 1× TB S-T and exposed to a phosphor screen. Radioactive signal from protein-linked, RNase-protected RNA was captured on a phosphor screen and documented using a phosphor imager. Western blot analysis was performed on the same membrane for different components of the eIF3 complex and ABCF1. Antibodies used for IP and/or western blotting were: goat IgG (sc-2028, Santacruz Biotechnology), rabbit IgG (sc-2027, Santacruz Biotechnology), rabbit anti-ABCF1 (ab190798, Abcam), goat anti-eIF3a (sc-22375, Santacruz Biotechnology), goat anti-eIF3b (sc-16377, Santacruz Biotechnology), mouse anti-eIF3k (sc-393234, Santa Cruz Biotechnology). To visualize proteins, the membrane was stained with Amido black.

eIF3a/m$^6$A Overlap Analysis eIF3a PAR-iCLIP site clusters were identified with Pyico-clip (Althammer et al., "A Versatile Toolkit for the Analysis of High-Throughput Sequencing Data," Bioinformatics 27:3333-3340 (2011) and Raj et al., "A Global Regulatory Mechanism for Activating an Exon Network Required for Neurogenesis," *Mol. Cell* 56:90-103 (2014), which are hereby incorporated by reference in their entirety) and pooled for replicate samples. Overlap between eIF3a PAR-iCLIP site clusters within 5'UTRs and m$^6$A sites within 5'UTRs was computed using a non-parametric test based on 100 random shufflings of eIF3a clusters. These random shufflings were performed within the same 5'UTR regions (as annotated using RefSeq genes) where the eIF3a PAR-iCLIP site clusters occur, so as to avoid any bias introduced by shuffling in regions outside of 5'UTRs. Single-nucleotide m⁶A sites were obtained from Linder et al., "Single-Nucleotide-Resolution Mapping of m⁶A and m⁶Am Throughout the Transcriptome," *Nat. Methods* 12(8):767-72 (2015) (which is hereby incorporated by reference in its entirety).

Distance Analysis of eIF3a and m⁶A Sites

For eIF3A binding site and m⁶A site distance plots, genomic coordinates (hg19) of single-nucleotide m⁶A sites in 5'UTRs were expanded upstream and downstream by 200 nucleotides and then divided into 10 nucleotide bins. For each bin, a mean eIF3a read count was obtained which was derived from the eIF3a PAR-iCLIP clusters common to the two iCLIP biological replicates (clusters were called individually first for each replicate using pyicoclip (p<0.0001), and an intersection of the called clusters, representing high-confidence eIF3A RNA binding regions, was then used). The sum of mean read counts for each bin was then plotted. For the control (random As) dataset, a python script was used to generate the same number of random genomic coordinates as m⁶A sites. These random coordinates were obtained from the same 5'UTR sequences that the m⁶A sites were derived from. Bed files were processed using Bedtools, and the plot was plotted in R using R Studio. Enrichment of mean read counts at 0+/−10 nucleotide distance from m⁶A sites was compared to the average of mean read counts generated from the randomly generated A sites (100 iterations) using a one sample t-test. Read coverage around one set of the randomly generated A sites is shown in the graph.

Comparison of eIF3 PAR-CLIP/iCLIP Replicates and Datasets

Correlation of mapped unique reads between the two eIF3A PAR-iCLIP replicates was determined for 25,000 randomly chosen genomic bins in 100 nucleotide windows across the human genome. Mean read counts in RPM (reads per million uniquely mapped reads) for each window were plotted on a scatterplot for each replicate. Association between replicates was tested using Pearson's correlation test in R. Analysis of the correlation between replicates 2 and 3 (SRR1761289 and SRR1761290, respectively) of the eIF3 PAR-CLIP dataset published by Lee et al.,"eIF3 Targets Cell-Proliferation Messenger RNAs for Translational Activation or Repression," *Nature* 522:111-114 (2015) (which is hereby incorporated by reference in its entirety) was performed similarly, with 100 nt windowed bins including only those with RPM>1 in order to analyze RNAs present in both replicates. Comparison of eIF3a PAR-iCLIP data to eIF3 PAR-CLIP data (Lee et al., "eIF3 Targets Cell-Proliferation Messenger RNAs for Translational Activation or Repression," *Nature* 522:111-114 (2015), which is hereby incorporated by reference in its entirety) was performed in the same manner as the comparison between the eIF3 PAR-CLIP replicates.

m⁶A Profiling and Analysis m⁶A profiling was performed as described to detect m⁶A sites at single nucleotide-resolution (Linder et al., "Single-Nucleotide-Resolution Mapping of m⁶A and m⁶Am Throughout the Transcriptome," *Nat. Methods* 12(8):767-72 (2015), which is hereby incorporated by reference in its entirety). Analysis of m⁶A profiling datasets from Dominissini et al., "Topology of the Human and Mouse m⁶A RNA Methylomes Revealed by m⁶A-Seq.," *Nature* 485:201-206 (2012), which is hereby incorporated by reference in its entirety, was done using the MACS peak calling software. Annotation of bed files and metagene profiling was performed as described in Linder et al., "Single-Nucleotide-Resolution Mapping of m⁶A and m⁶Am Throughout the Transcriptome," *Nat. Methods* 12(8):767-72 (2015) (which is hereby incorporated by reference in its entirety).

Gene Ontology ("GO") Analysis

GO functional annotation was performed using DAVID Bioinformatics Resources (Huang et al., "Systemic and Integrative Analysis of Large Gene Lists Using DAVID Bioinformatics Resources," *Nat. Protoc.* 4:44-57 (2009), which is hereby incorporated by reference in its entirety) with a p-value threshold of 0.01. All m⁶A-containing mRNAs were used as the background gene list.

Example 1

Ribosomal Initiation Complexes Assemble on m⁶A-Containing mRNAs Independently of the Cap-Binding Protein eIF4E Although m⁶A is predominantly localized near stop codons and in 3'UTRs in several thousand mRNAs, hundreds of cellular mRNAs contain m⁶A within their 5'UTR (Linder et al., "Single-Nucleotide-Resolution Mapping of m⁶A and m⁶Am Throughout the Transcriptome," *Nat. Methods* 12(8):767-72 (2015) and Meyer et al., "Comprehensive Analysis of mRNA Methylation Reveals Enrichment in 3' UTRs and Near Stop Codons," *Cell* 149:1635-1646 (2012), which are hereby incorporated by reference in their entirety), and the function of these m⁶A residues is unknown. Since the 5' UTR is important in regulating translation initiation, the possibility that 5' UTR-localized m⁶As might influence this process was considered. On most eukaryotic mRNAs, translation begins with assembly of a 43S preinitiation complex, comprising a 40S ribosomal subunit, a eukaryotic initiation factor 2 (eIF2)-GTP/Met-tRNA$_i^{Met}$ ternary complex, and eIFs 3, 1 and 1A (Jackson et al., "The Mechanism of Eukaryotic Translation Initiation and Principles of its Regulation," *Nat. Rev. Mol. Cell Biol.* 11:113-127 (2010), which is hereby incorporated by reference in its entirety). 43S complexes are typically recruited to mRNA by a cap-binding complex, eIF4F. eIF4F has three subunits: eIF4E, which binds the m⁷G 5' cap; eIF4A, an RNA helicase; and eIF4G a scaffold that also binds eIF3, thereby recruiting the 43S complex. After attachment, 43S complexes scan to the initiation codon where they form 48S initiation complexes (Jackson et al., "The Mechanism of Eukaryotic Translation Initiation and Principles of its Regulation," *Nat. Rev. Mol. Cell Biol.* 11:113-127 (2010), which is hereby incorporated by reference in its entirety).

To investigate the effect of m⁶A on translation initiation, a 48S in vitro reconstitution approach was used, in which ribosomal complexes are assembled on mRNA 5"UTRs using purified translational components (40S subunits, initiation factors and Met-tRNA$_i^{Met}$) (Pestova et al., "The Roles of Individual Eukaryotic Translation Initiation Factors in Ribosomal Scanning and Initiation Codon Selection," *Genes Dev.* 16:2906-2922 (2002), which is hereby incorporated by reference in its entirety). Formation of the 48S complex at the start codon is then monitored by reverse transcriptase-mediated extension of a [$^{32}$P]-labeled primer annealed to ribosome-bound mRNA. cDNA synthesis is arrested by the 40S ribosome subunit, yielding characteristic toe-prints at its leading edge, +15-17 nucleotides downstream of the initiation codon. This assay can identify the initiation factors and sequence features of 5'UTRs which are required for initiation and has been used in mechanistic studies of viral internal ribosome entry sites (IRESs) (Pestova et al., "Translation Elongation after Assembly of Ribosomes on the Cricket Paralysis Virus Internal Ribosomal Entry Site Without Initiation Factors or Initiator tRNA," *Genes Dev.* 17:181-186 (2003), which is hereby incorporated by reference in its entirety).

To test the role of $m^6A$ in 48S complex formation, toe-printing with 5'-capped mRNAs comprising the 54 nucleotide-long β-globin 5' UTR followed by a short coding sequence, stop codon, and 3'UTR was performed. Consistent with previous studies (Pestova et al., "The Roles of Individual Eukaryotic Translation Initiation Factors in Ribosomal Scanning and Initiation Codon Selection," *Genes Dev.* 16:2906-2922 (2002), which is hereby incorporated by reference in its entirety), 48S initiation complexes were detected at the start codon of A-containing mRNA in the presence of the complete set of eIFs (1, 1A, 2, 3, 4A, 4B, 4F), and omission of group 4 eIFs nearly abrogated 48S complex formation (FIG. 1A, compare lanes 2 and 4). This is consistent with the known role for the eIF4 cap-binding complex in recruiting the 43S complex to mRNA (Gingras et al., "eIF4 Initiation Factors: Effectors of mRNA Recruitment to Ribosomes and Regulators of Translation," *Annu. Rev. Biochem.* 68:913-963 (1999), which is hereby incorporated by reference in its entirety).

When mRNAs in vitro transcribed to contain 50% $m^6A$ were used, it was found that 48S complexes readily assembled after addition of the complete set of eIFs, as was seen with unmethylated mRNA. However, unlike the unmethylated mRNA, 48S complexes formed on $m^6A$-containing mRNA even in the absence of group 4 eIFs (FIG. 1A). Thus, initiation on $m^6A$-containing mRNA is distinct from initiation on mRNA lacking $m^6A$ and does not require the eIF4 cap-binding complex.

Figure 1B:
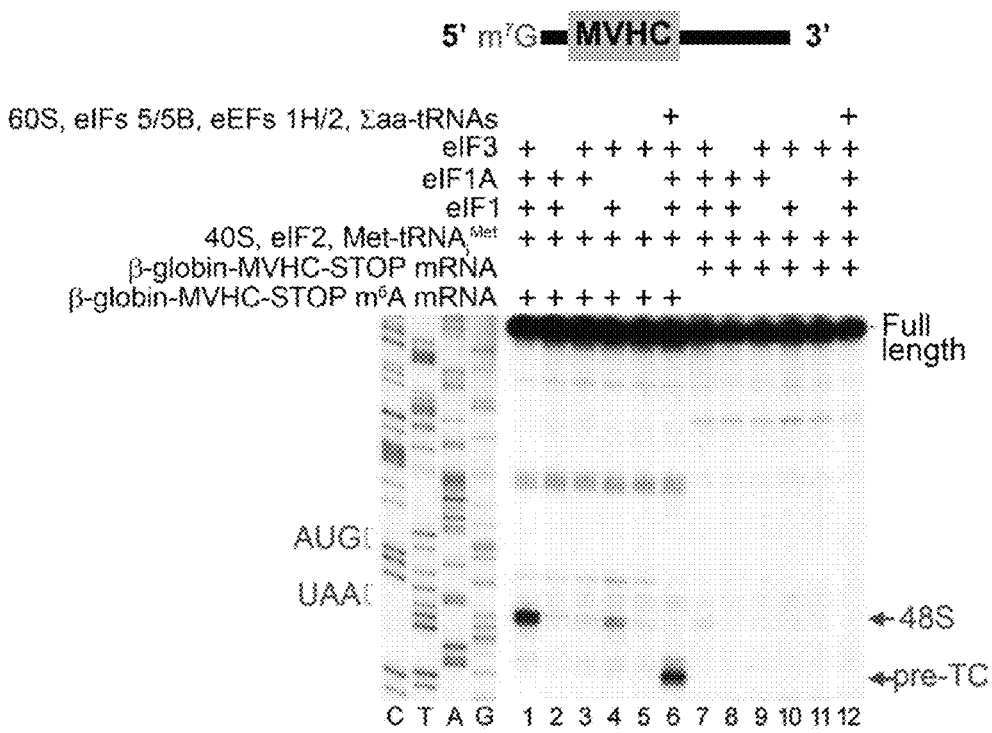
Figure 1C:
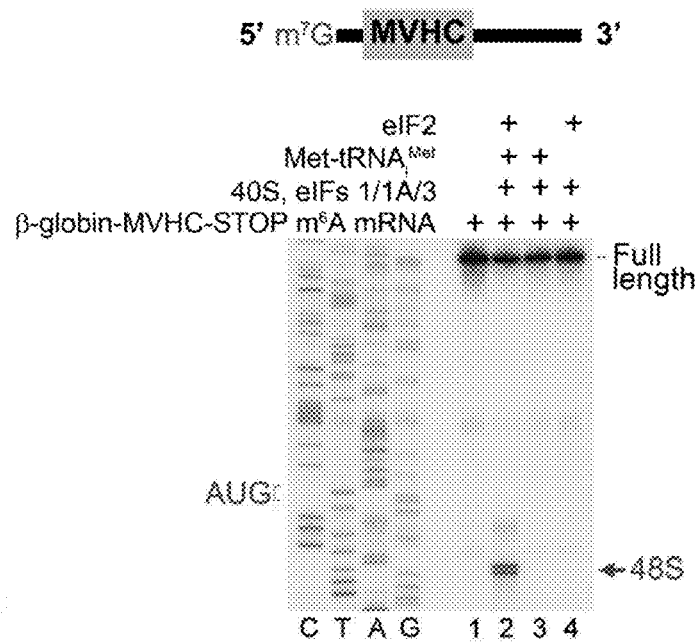

To further establish the factor requirements for initiation on $m^6A$-containing mRNA, each initiation factor was selectively omitted prior to performing toe-printing. These experiments show that efficient initiation on $m^6A$-containing mRNA only requires the presence of eIFs1, 1A, 2, 3, and the 40S subunit (FIGS. 1B, 1C). 48S complexes that formed on $m^6A$-containing mRNA in the absence of group 4 eIFs were functional, as addition of the 60S ribosomal subunit, Σaa-tRNAs, and factors required for subunit joining and elongation (eIF5, eIF5B, eEF2, and eEF1H) resulted in formation of 80S ribosomes that underwent efficient elongation and yielded pre-termination complexes at the stop codon (FIG. 1B). Thus, translation-competent 48S complexes can form on $m^6A$-containing mRNA in the absence of eIF4E.

Example 2

$m^6A$ Enables Translation in a 5' Cap-Independent Manner in Cell-Free Extracts

Figure 3A:
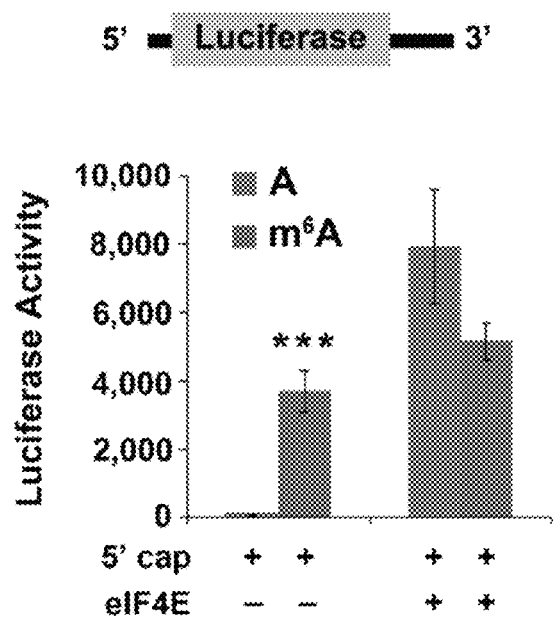

It was next asked if $m^6A$ induces eIF4E-independent translation in cell-free extracts. To investigate this, HeLa extract which has low eIF4E activity (Mikami et al., "An Efficient Mammalian Cell-Free Translation System Supplemented with Translation Factors," *Protein Expr. Purif.* 46:348-357 (2006), which is hereby incorporated by reference in its entirety) (FIGS. 2A, 2B) and thus provides an ideal system for studying eIF4E-independent translation, was used. Indeed, addition of a capped, nonmethylated luciferase-encoding mRNA containing the β-globin 5'UTR to the HeLa extract did not produce measureable luciferase activity unless eIF4E was added (FIG. 3A). Thus, cap-dependent translation in this extract is dependent on exogenous eIF4E.

Figures 2F, 2G:
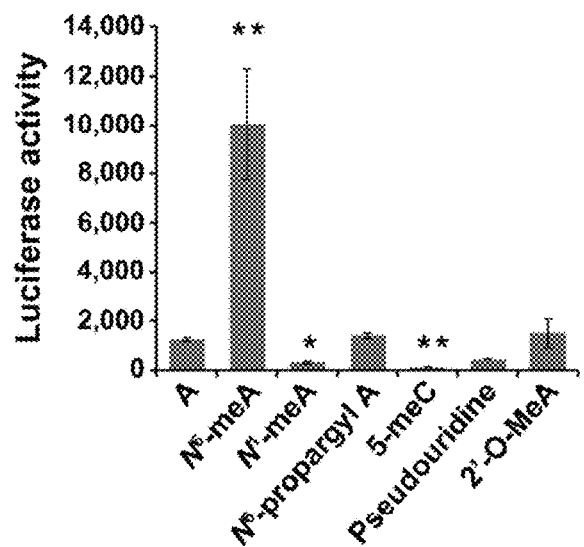
Figure 3B:
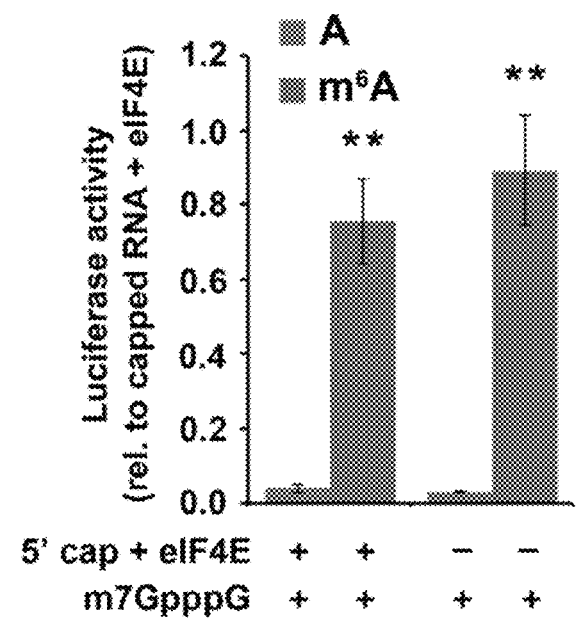

HeLa extracts were next used to determine if transcripts containing $m^6A$ require eIF4E. In contrast to the mRNA containing exclusively A, 5'-capped mRNA containing 50% $m^6A$ was readily translated even in the absence of added eIF4E (FIG. 3A). Furthermore, addition of 1 mM $m^7GpppG$ a cap analog that sequesters cap-binding proteins (Ray et al., "Two Internal Ribosome Entry Sites Mediate the Translation of p53 Isoforms," *EMBO Rep.* 7:404-410 (2006), which is hereby incorporated by reference in its entirety), abolished translation of 5'-capped, A-containing mRNA but had no effect on $m^6A$-containing mRNA (FIG. 3B). Lastly, A-containing mRNA synthesized without a cap was not translated, whereas $m^6A$-containing, uncapped mRNA was readily translated (FIG. 3C). The increased translation of $m^6A$-containing mRNA in these experiments was not due to increased stability of $m^6A$-containing mRNA, as RT-qPCR and radiolabeled mRNA stability measurements indicated similar levels of A- and $m^6A$-containing luciferase mRNA after incubation with HeLa extracts (FIGS. 2C-2F). Collectively, these data indicate that translation of $m^6A$-containing mRNA exhibits marked independence of the 5' cap and eIF4E.

Example 3

A Single $m^6A$ is Sufficient to Induce Cap-Independent Translation

Since the mRNAs used in the in vitro translation assays have $m^6A$ throughout the transcript, it is unclear if the translational effects are due to $m^6A$ in the 5'UTR or elsewhere in the mRNA. To determine the contributions of specific $m^6A$ residues to cap-independent translation, mRNAs that only contain $m^6A$ in the coding sequence were examined. Uncapped, luciferase-encoding mRNAs which contained zero $m^6A$ residues within the 5' UTR showed no translation, indicating that $m^6A$ residues in the coding sequence are unable to induce cap-independent translation (FIG. 3C). However, addition of a single $m^6A$ residue at the beginning, middle, or end of the 5' UTR was sufficient to markedly induce cap-independent translation (FIG. 3D).

Figure 3E:
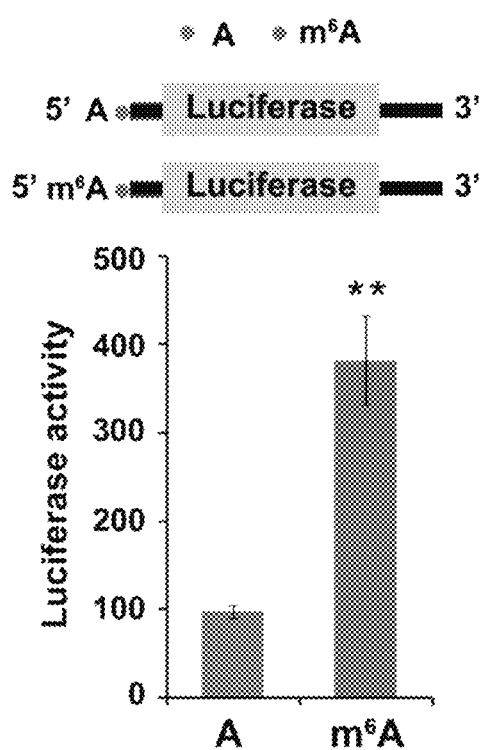

To determine if a single 5' UTR $m^6A$ residue can promote cap-independent translation, uncapped luciferase-encoding mRNAs which contain $m^6A$ as the first transcribed nucleotide was used. This mRNA contains a single $m^6A$ residue in the 5' UTR, and the remainder of the A's within the transcript are unmethylated. For mRNAs lacking $m^6A$, negligible luciferase synthesis were detected (FIG. 3E). However, transcripts containing a single 5' $m^6A$ were readily translated (FIG. 3E). Notably, the level of translation induced by a 5' $m^6A$ is less than the translation induced by a single $m^6A$ residue located internally within the 5' UTR, which likely reflects inefficient incorporation of $m^6A$ at the first position of 5' $m^6A$-containing transcripts. Collectively, these experiments indicate that a single $m^6A$ can induce cap-independent translation.

To determine whether $m^6A$-mediated cap-independent translation is a specific effect caused by the presence of $m^6A$, uncapped luciferase transcripts containing A, $m^6A$, or other modified nucleotides, such as $N^1$-methyladenosine, 2'-O-methyladenosine, pseudouridine, and 5-methylcytosine were synthesized. In each case, there was negligible luciferase synthesis unless $m^6A$ was present (FIG. 2G).

The effect of $m^6A$ reflects impaired base pairing caused by modification of the $N^6$ position (Roost et al., "Structure and Thermodynamics of N(6)-Methyladenosine in RNA: A Spring-Loaded Base Modification," *J. Am. Chem. Soc.* 137: 2107-2115 (2015), which is hereby incorporated by reference in its entirety) was next evaluated. However, mRNA containing N⁶-propargyladenosine, which contains a slightly larger modification compared to a methyl group at the 1V⁶ position, failed to undergo cap-independent translation (FIG. 2G). Thus, m⁶A-induced structural changes are unlikely to account for the cap independence conferred by m⁶A.

Example 4 m⁶A-Induced Translation Initiation Occurs Through a 5' End-Dependent Mechanism

Figure 4A:
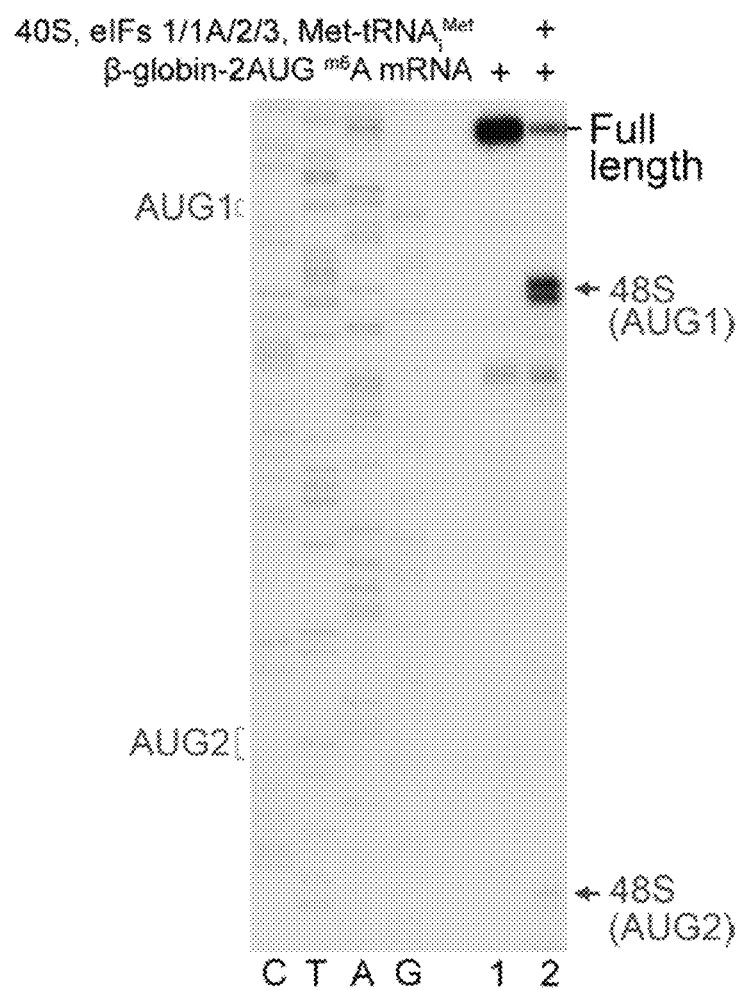

Results described herein indicate that m⁶A residues within the 5' UTR are capable of promoting cap-independent translation. However, the majority of m⁶A residues are found in the coding sequence and 3'UTR (Meyer et al., "Comprehensive Analysis of mRNA Methylation Reveals Enrichment in 3' UTRs and Near Stop Codons," *Cell* 149:1635-1646 (2012), which is hereby incorporated by reference in its entirety). Therefore, it was investigated whether these internal m⁶A residues can induce internal ribosome entry. To test this, an m⁶A-containing β-globin mRNA in which the wild-type AUG initiation codon was removed and two new AUG triplets were introduced upstream and downstream of the native position (FIG. 4A) was used. When this mRNA was incubated with 40S, eIFs1/1A/2/3, and Met-tRNA$_i^{Met}$, 48S complexes occurred almost exclusively at the first AUG; with very low levels of detectable 48S complex formation at the downstream AUG (FIG. 4A). These data suggest that m⁶A preferentially induces translation at the first suitable start codon in the mRNA as opposed to promoting translation through an internal entry-based mechanism.

Figure 2H:
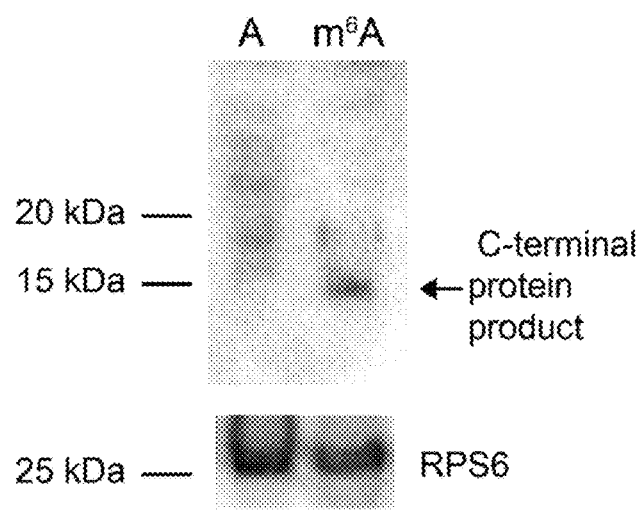

Next, HeLa cell lysates were used to in vitro translate a GFP reporter mRNA containing an internal near-Kozak AUG in addition to the natural AUG encoding full-length GFP. However, m⁶A-mediated translation of the ~17 kDa product produced from the internal AUG was not observed, and instead robust translation of the full-length protein produced from the first AUG was observed (FIG. 4B, FIG. 2H). These results are consistent with the toe-printing experiments and suggest that m⁶A preferentially induces translation at the first acceptable start codon.

Figure 4D:
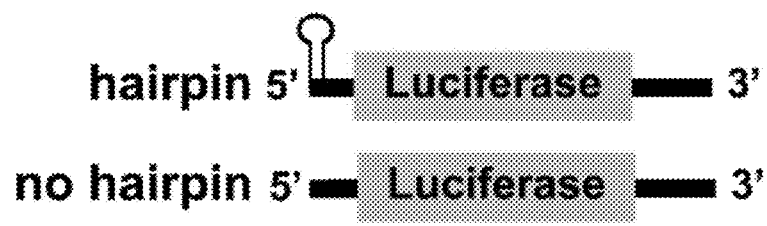

The selective use of the first AUG for translation initiation suggests a model of m⁶A-mediated initiation that involves a 5' end-dependent scanning mechanism as opposed to internal ribosomal entry. A similar mode of initiation, which is also cap-independent but shows 5'-end dependence, was recently described for mRNA containing in its 5' UTR an eIF4G-binding viral IRES-domain (Terenin et al., "A Novel Mechanism of Eukaryotic Translation Initiation that is Neither m7G-cap-, nor IRES-Dependent," *Nucleic Acids Res.* 41:1807-1816 (2013), which is hereby incorporated by reference in its entirety). Additionally, cap-independent 5' end-dependent mechanisms of translation initiation have previously been observed in assays using rabbit reticulocyte lysates (De Gregorio et al., "Translational Activation of Uncapped mRNAs by the Central Part of Human eIF4G is 5' End-Dependent," *RNA* 4(7):828-36 (1998), which is hereby incorporated by reference in its entirety). To test directly whether m⁶A promotes entry through the 5' end, an uncapped, luciferase-encoding mRNA that contains a stable hairpin at the extreme 5' end of the mRNA to block 5' end-dependent ribosome entry was used. The presence of this hairpin markedly reduced the robust translation of m⁶A-containing mRNA which is normally observed (FIG. 4D). Thus, m⁶A-mediated initiation requires an accessible 5'-terminal end on the mRNA. Taken together, these data indicate that 5' UTR m⁶As are distinct from classical viral IRES elements since m⁶A promotes recruitment of ribosomal preinitiation complexes to the 5' end of mRNA, rather than enabling internal ribosome entry.

Example 5 eIF3 Selectively Binds m⁶A-Containing RNA

How m⁶A is recognized to induce translation of mRNAs was next investigated. The in vitro 48S reconstitution assays showed that recruitment of the 43S preinitiation complex to m⁶A-containing mRNA only requires eIFs 1, 1A, 2, and 3, and the 40S subunit. Thus, one of these components binds m⁶A.

Figure 5A:
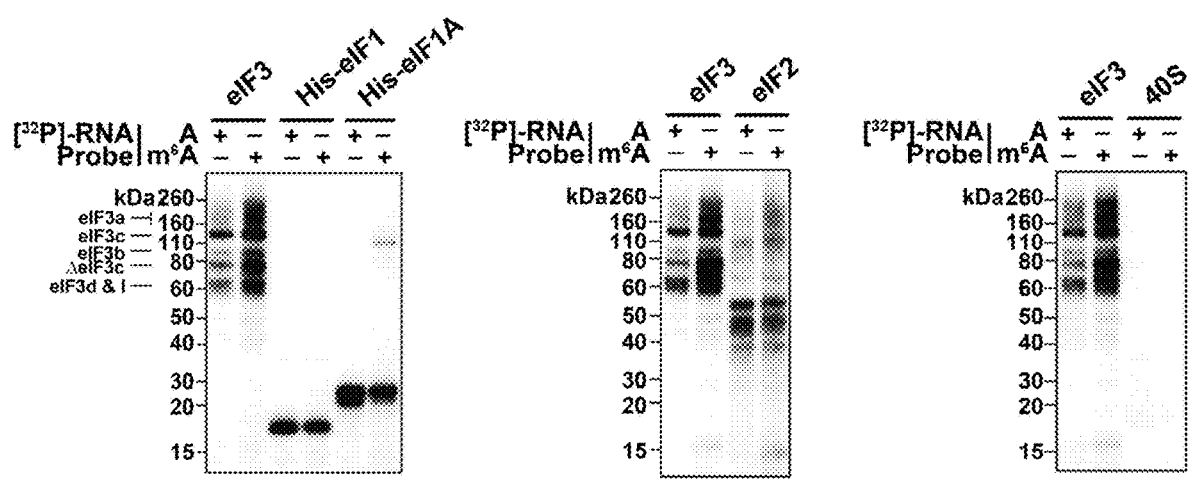
FIGS. 5A-5B demonstrate that the 43S complex component eIF3 binds m⁶A.
Figure 6A:
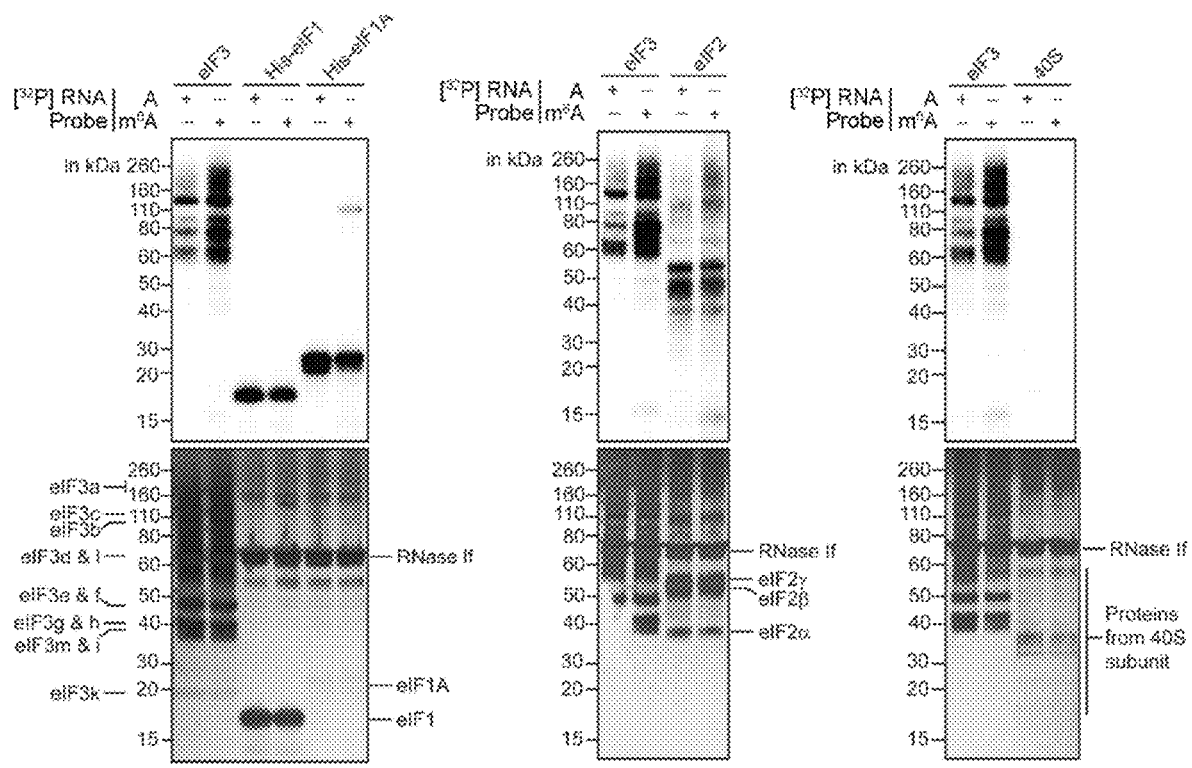
Figures 6B, 6C, 6D:
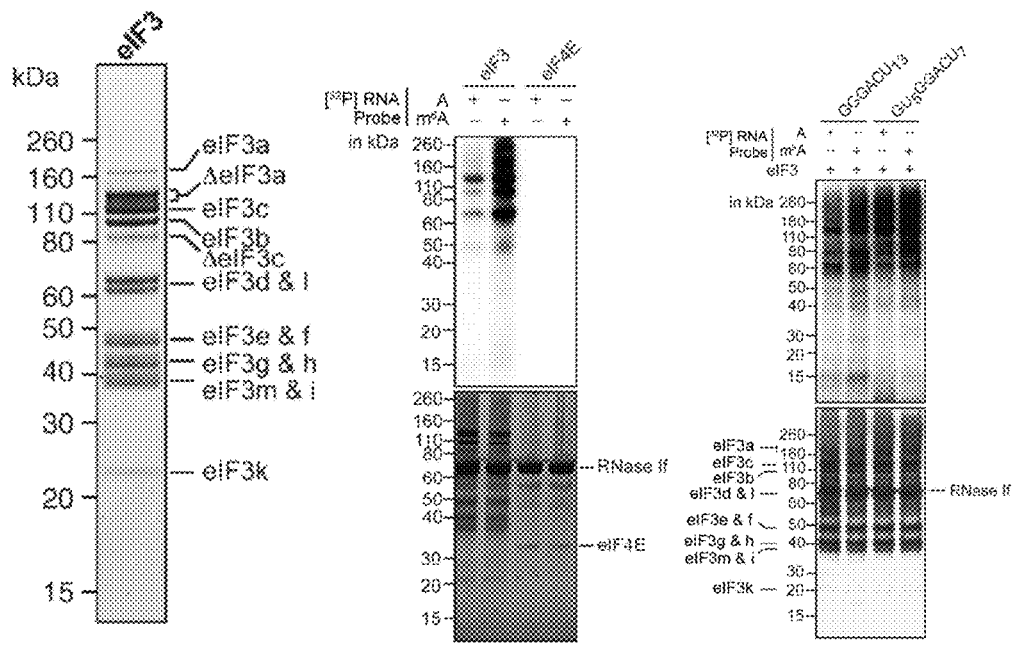

To test which of these factors interacts with m⁶A, applicants used an m⁶A crosslinking assay in which a [³²P]-labeled RNA probe containing a single A or m⁶A in its naturally-occurring GAC context was UV-crosslinked to each translational component. Crosslinked proteins were then detected by SDS-PAGE and autoradiography.

eIFs 1, 1A, 2 and the 40S subunit showed equal levels of crosslinking to the A- and m⁶A-containing probes (FIG. 5A, FIG. 6A). However, crosslinking of eIF3 to the m⁶A-containing probe was substantially increased compared to the A-containing probe, suggesting that this factor constitutes the major m⁶A-binding activity of the 43S complex (FIG. 5A, FIGS. 6B, 6C).

The preferential binding of eIF3 to m⁶A was not affected by changing the position of the m⁶A together with its context nucleotides within the probe (FIG. 6D). However, when the natural nucleotide context of m⁶A was changed from GAC to UAC or CAG,1 the m⁶A-containing probe showed significantly reduced crosslinking to eIF3 (FIG. 6E). Thus, efficient eIF3 crosslinking to m⁶A-containing RNA occurs when the probe contains m⁶A within its natural sequence context. Furthermore, when mRNAs which contained a single m⁶A residue within their 5' UTR were subjected to in vitro translation, it was found that m⁶A residues in a GAC context promoted robust cap-independent translation, whereas m⁶As in a UAC or CAG exhibited markedly reduced translation (FIG. 6F). These data indicate that eIF3 preferentially binds to m⁶A residues in their natural sequence context to promote cap-independent translation.

eIF3 is a large multiprotein complex comprising 13 subunits (a-m) (des Georges et al., "Structure of Mammalian eIF3 in the Context of the 43S Preinitiation Complex," *Nature* 525:491-495 (2015), which is hereby incorporated by reference in its entirety) that interacts with mRNA in 48S complexes (Pisarev et al., "Ribosomal Position and Contacts of mRNA in Eukaryotic Translation Initiation Complexes," *EMBO 1* 27:1609-1621 (2008), which is hereby incorporated by reference in its entirety). UV-crosslinking studies showed that the interaction between eIF3 and RNA occurs at a multi-subunit interface (Lee et al.,"eIF3 Targets Cell-Proliferation Messenger RNAs for Translational Activation or Repression," *Nature* 522:111-114 (2015), which is hereby incorporated by reference in its entirety). Similarly, in crosslinking assays, the m⁶A-containing probe induced strong labeling of several protein bands, ranging in molecular weight from ~60 to ~160 kDa (FIG. 5A, FIGS. 6A-6E). Particularly strong labeling was observed in the area of ΔeIF3a/eIF3c, ΔeIF3c, and eIF3e/eIF3d (FIGS. 6A-6E). These data suggest that m⁶A-containing RNA may interact with a multi-subunit interface within eIF3.

Figure 5B:
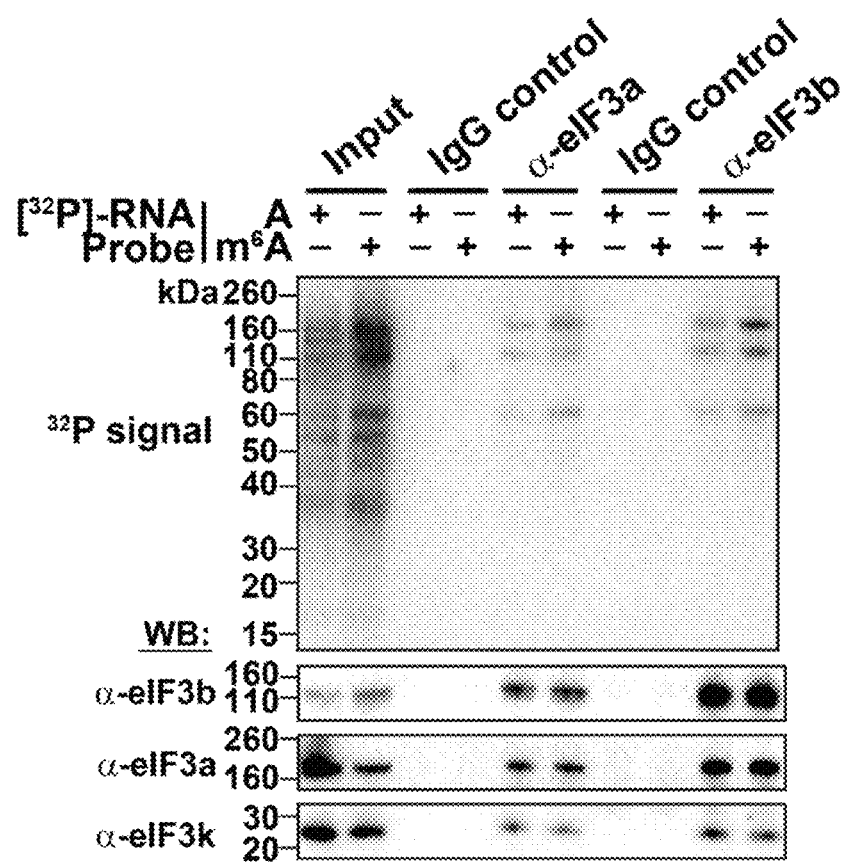
Figure 7A:
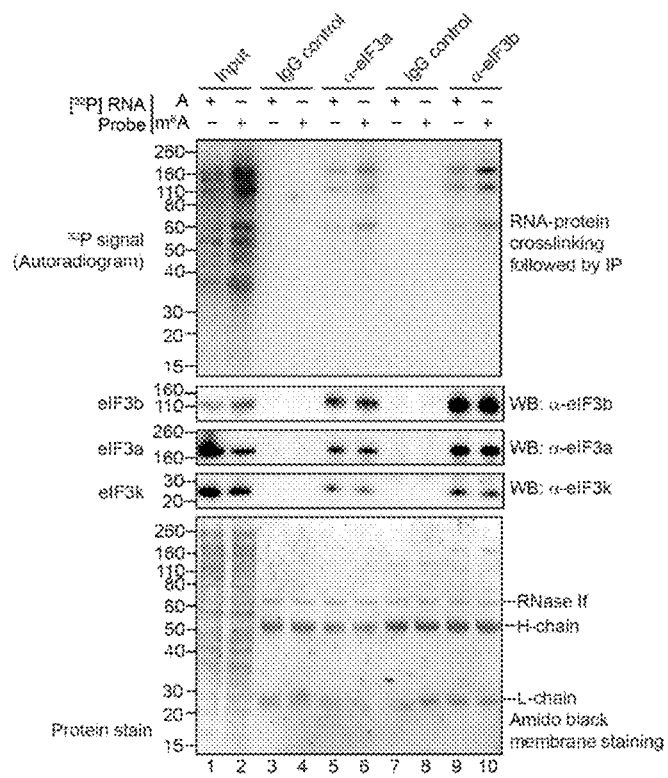
Figure 7B:
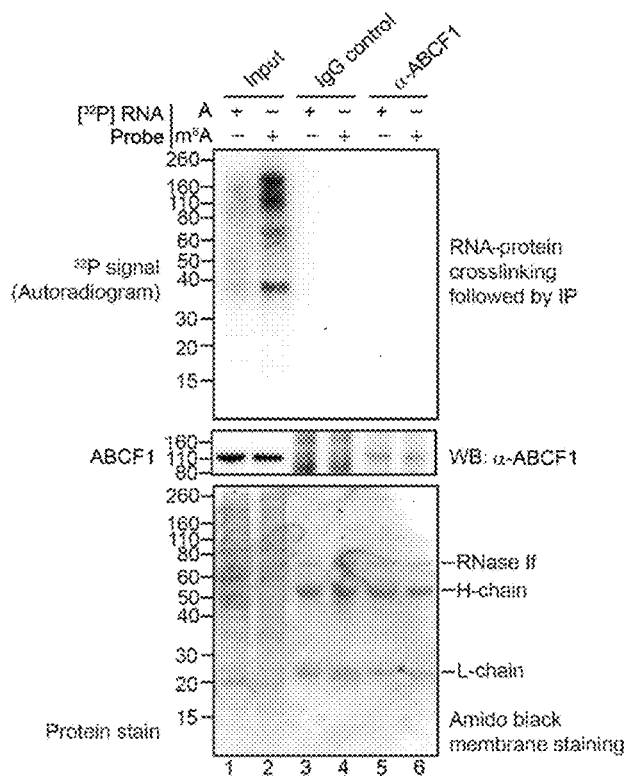

To further explore the binding of m⁶A-containing RNA to eIF3, HeLa cellular lysates were used. Crosslinking using a radioactive m⁶A-containing RNA probe resulted in the labeling of specific protein bands that were increased relative to the A-containing probe (FIG. 5B). Immunoprecipitation of crosslinked extracts using either of two eIF3 subunit-specific antibodies selectively precipitated these bands, confirming that the increased binding to m⁶A-containing RNA was mediated by eIF3. Immunoprecipitation with a control antibody recognizing a different initiation factor-associated protein (ABCF1) did not precipitate these bands (FIG. 5B; FIGS. 7A, 7B). Thus, these data further suggest that m⁶A-containing RNA interacts with eIF3.

The m⁶A binding protein, YTHDF1, interacts with a diverse set of proteins, including eIF3 (Wang et al., "N(6)-Methyladenosine Modulates Messenger RNA Translation Efficiency," *Cell* 161:1388-1399 (2015), which is hereby incorporated by reference in its entirety). Thus, the possibility that recruitment of eIF3 to m⁶A-containing RNA in the in vitro translation and crosslinking assays is mediated by a YTH-family m⁶A-binding protein was considered. However, silver staining of all the initiation factors used in the toe-printing assays failed to show protein bands in the ~60-64 kD range of these proteins (FIG. 6). Additionally, mass spectrometry analysis of the purified eIF3 did not reveal YTH family proteins (FIG. 7C) (des Georges et al., "Structure of Mammalian eIF3 in the Context of the 43S Preinitiation Complex," *Nature* 525:491-495 (2015), which is hereby incorporated by reference in its entirety). Finally, YTHDF1 was not present in the highly purified eIF3 preparations used in the crosslinking assays, nor were any of the related YTH-domain containing family of m⁶A binding proteins (FIG. 7D) (des Georges et al., "Structure of Mammalian eIF3 in the Context of the 43S Preinitiation Complex," *Nature* 525:491-495 (2015), which is hereby incorporated by reference in its entirety). Thus, these data support the idea that eIF3 is able to directly bind m⁶A.

Figure 8B:
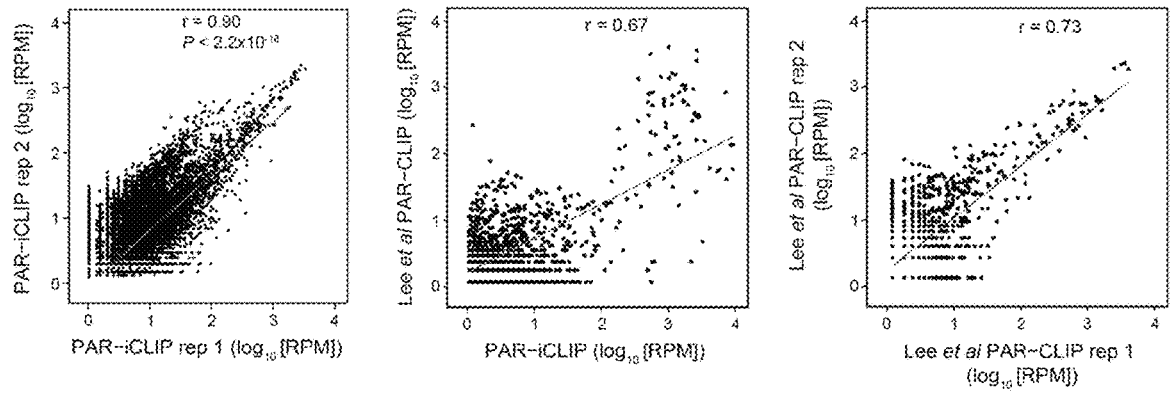

To determine whether eIF3 binds m⁶A in cells, PAR-iCLIP was performed to identify zero-distance binding sites of eIF3 in cellular mRNAs. eIF3a binding sites were primarily localized to 5' UTRs of mRNAs and showed a high degree of overlap with eIF3 binding sites reported previously (Lee et al.,"eIF3 Targets Cell-Proliferation Messenger RNAs for Translational Activation or Repression," *Nature* 522:111-114 (2015), which is hereby incorporated by reference in its entirety) (FIGS. 8A, 8B).

Figure 8E:
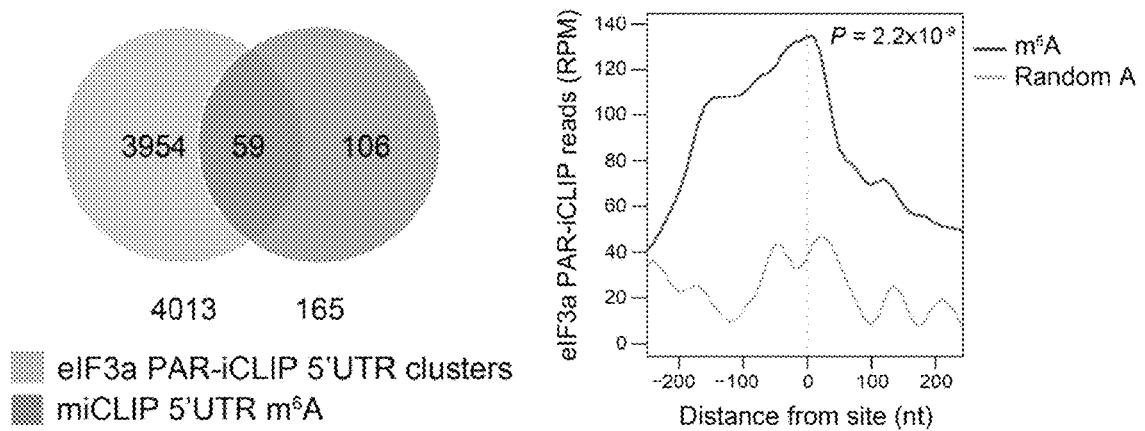
Figure 9A:
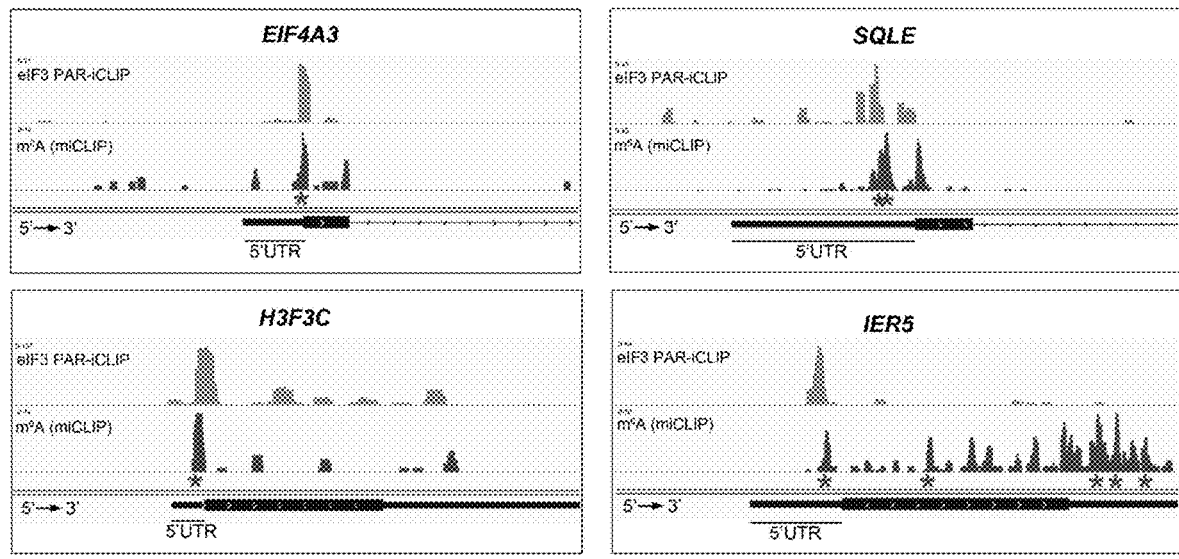
FIGS. 9A-9B demonstrate that eIF3 binding sites within cellular mRNAs localize to cites of m$^6$A residues within the 5' UTR.

To determine whether eIF3a binds to sites of m⁶A in 5' UTRs, the overlap of eIF3a binding sites with m⁶A residues mapped at single nucleotide-resolution in 5' UTRs was evaluated (Linder et al., "Single-Nucleotide-Resolution Mapping of m⁶A and m⁶Am Throughout the Transcriptome," *Nat. Methods* 12(8):767-72 (2015), which is hereby incorporated by reference in its entirety). To test this, a permutation-based approach in which eIF3a binding sites were randomized while preserving the distribution and positional bias of eIF3a PAR-iCLIP tags in 5' UTRs was used. Multiple permutations (n>100) were used, and the statistical significance of overlap between eIF3 PAR-iCLIP sites and m⁶A residues was evaluated. A statistically significant overlap between m⁶A residues and eIF3 binding sites in 5' UTRs was found, with 35% of 5' UTR m⁶A residues overlapping with eIF3 sites (FIGS. 8C-8E). Since single nucleotide-resolution m⁶A mapping distinguishes between m⁶A residues and the m⁶Am residues which exist as part of the 5' cap in some mRNAs (Kruse et al., "A Novel Synthesis and Detection Method for Cap-Associated Adenosine Modifications in Mouse mRNA," *Sci. Rep.* 1:126 (2011) and Linder et al., "Single-Nucleotide-Resolution Mapping of m⁶A and m⁶Am Throughout the Transcriptome," *Nat. Methods* 12(8):767-72 (2015), which are hereby incorporated by reference in their entirety), it was determined that this overlap was specific to m⁶A residues within 5' UTRs (FIGS. 8C and 9A). Taken together, these results support the idea that eIF3 is associated with m⁶A residues in the 5' UTRs of cellular mRNAs.

Figure 9B:
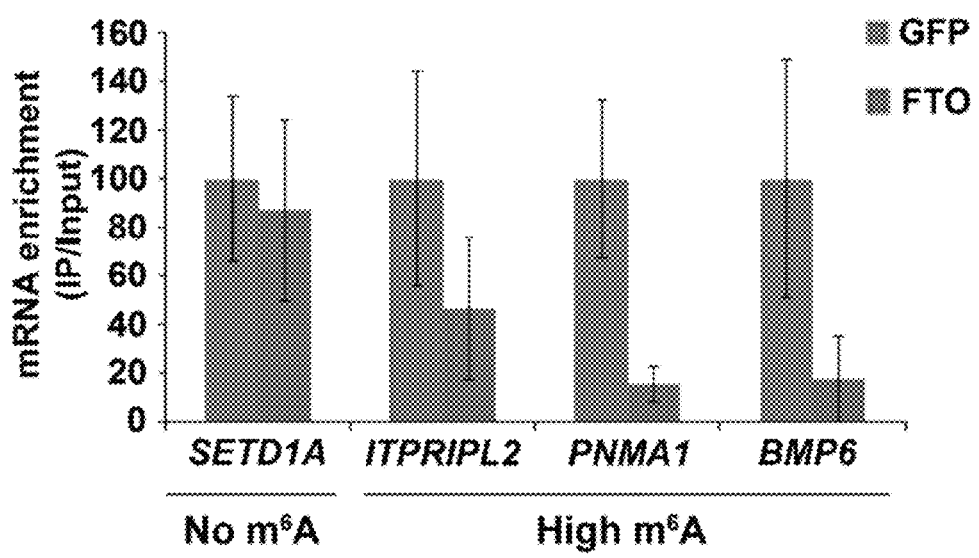

To further test the physiological association of eIF3 and m⁶A predicted by the PAR-iCLIP analysis, eIF3 protein/RNA immunoprecipitation from HEK293 cells expressing the m⁶A-demethylating enzyme was performed (Jia et al., "N6-Methyladenosine in Nuclear RNA is a Major Substrate of the Obesity-Associated FTO," *Nat. Chem. Biol.* 7(12): 885-7 (2011), which is hereby incorporated by reference in its entirety). The abundance of target mRNA 5' UTRs in the eIF3-bound fraction was then measured using RT-qPCR with primers that amplify the 5' UTR regions containing the residue. mRNAs that contain a high stoichiometry m⁶A site within their 5' UTR (Meyer et al., "Comprehensive Analysis of mRNA Methylation Reveals Enrichment in 3' UTRs and Near Stop Codons," *Cell* 149:1635-1646 (2012), which is hereby incorporated by reference in its entirety), were substantially depleted in the eIF3-bound fraction following Fto overexpression (FIG. 9B). In contrast, eIF3 immunoprecipitation of a control mRNA deficient in 5' UTR m⁶A (Meyer et al., "Comprehensive Analysis of mRNA Methylation Reveals Enrichment in 3' UTRs and Near Stop Codons," *Cell* 149:1635-1646 (2012), which is hereby incorporated by reference in its entirety) was unaffected by Fto overexpression (FIG. 9B). Taken together, these data support the idea that eIF3 interacts with mRNAs in an m⁶A-dependent manner in cells.

Example 6 m⁶A Within the 5' UTR Promotes Translation of Cellular mRNAs

To address whether mRNAs that contain 5' UTR m⁶A residues possess enhanced translation in cells, ribosome profiling-based measurements of mRNA TE in HeLa cells depleted of the m⁶A methyltransferase enzyme, METTL3, which results in depletion of all m⁶A residues in cells (Wang et al., "N(6)-Methyladenosine Modulates Messenger RNA Translation Efficiency," *Cell* 161:1388-1399 (2015), which is hereby incorporated by reference in its entirety) were examined. The TE of mRNAs based on the location of their m⁶A residues identified by single nucleotide-resolution m⁶A mapping was examined (Linder et al., "Single-Nucleotide-Resolution Mapping of m⁶A and m⁶Am Throughout the Transcriptome," *Nat. Methods* 12(8):767-72 (2015), which is hereby incorporated by reference in its entirety). Compared to mRNAs that lack m⁶A, transcripts which contain m⁶A residues within the coding sequence or 3' UTR were found to show no significant change in TE in METTL3-depleted cells (FIGS. 10A-10B). Similarly, mRNAs that contain m⁶A residues near the stop codon do not show reduced translation in METTL3-depleted cells. However, mRNAs containing 5' UTR m⁶A residues showed a large reduction in TE following METTL3 depletion, suggesting a preferential role for 5' UTR m⁶A in promoting mRNA translation (FIGS. 10A-10B, FIG. 11B). Residual translation may reflect ongoing cap-dependent translation in METTL3-deficient cells. The translation of mRNAs containing 5' UTR m⁶A residues was not suppressed in cells depleted of YTHDF1 (FIG. 11B), consistent with the idea that 5' UTR m$^6$A promotes translation through eIF3. Taken together, these data suggest that m$^6$A residues in the 5' UTR enhance the translation of mRNAs in cells.

Example 7

Heat Shock-Induced Translation of Hsp70 is Mediated by 5' UTR m$^{6A}$

The role of m$^6$A in promoting cap-independent translation in cells was next investigated. Since cellular translation involves both cap-dependent and cap-independent mechanisms, heat shock, was taken advantage of which induces a stress response that suppresses most cap-dependent translation (Holcik et al., "Translational Control in Stress and Apoptosis," *Nat. Rev. Mol. Cell. Biol.* 6:318-327 (2005), which is hereby incorporated by reference in its entirety). Heat-shock protein 70 (HSP70) is a stress response mRNA known to undergo increased transcription and cap-independent translation following heat shock (Lindquist et al., "The Heat-Shock Proteins," *Annu. Rev. Genet.* 22:631-677 (1988), which is hereby incorporated by reference in its entirety). Previous studies demonstrated that HSP70 contains an m$^6$A site within its 5' UTR (Schwartz et al., "Perturbation of m6A Writers Reveals Two Distinct Classes of mRNA Methylation at Internal and 5' Sites," *Cell Rep.* 8:284-296 (2014), which is hereby incorporated by reference in its entirety), and that methylation of the HSP70 5' UTR is increased following heat shock (Dominissini et al., "Topology of the Human and Mouse m6A RNA Methylomes Revealed by m6A-Seq.," *Nature* 485:201-206 (2012), which is hereby incorporated by reference in its entirety). However, the role of m$^6$A in cap-independent translation of HSP70 is not understood.

Figure 12A:
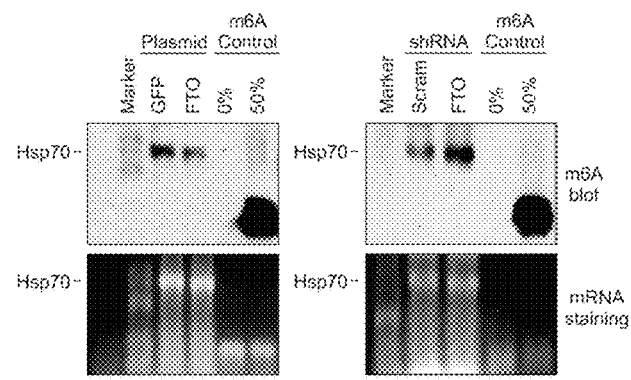
Figure 12B:
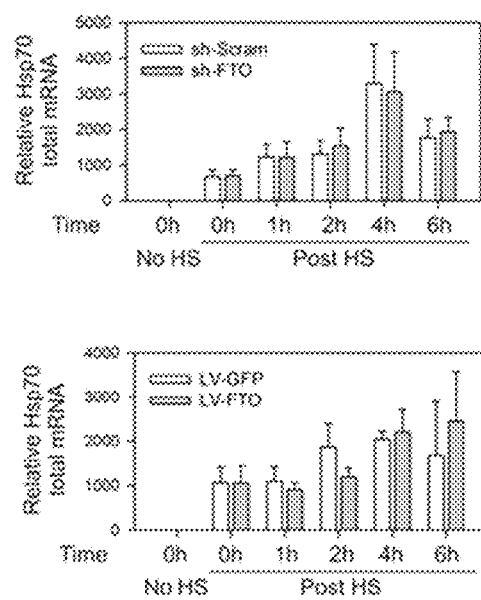

To test the effect of m$^6$A in HSP70 translation, altered expression of Fto was used to influence m$^6$A levels within the Hsp70 5' UTR. Knockdown of Fto resulted in a 60% increase in m$^6$A levels in Hsp70 mRNA in heat-shocked cells (FIG. 12A). Conversely, overexpressing Fto in heat-shocked cells reduced the level of m$^6$A in Hsp70 mRNA by 29% relative to heat-shocked cells overexpressing GFP (FIG. 12A). To determine whether altered m$^6$A levels in the Hsp70 5' UTR influence heat shock-induced Hsp70 translation, mouse embryonic fibroblasts (MEFs), which exhibit low Hsp70 levels prior to heat shock (Sun et al., "PI3K-mTORC1 Attenuates Stress Response By Inhibiting Cap-Independent Hsp70 Translation," *J. Biol. Chem.* 286:6791-6800 (2011), which is hereby incorporated by reference in its entirety) were used. In MEF cells stably expressing control shRNA, Hsp70 protein was readily detected 4 and 6 h after heat shock. However, in MEF cells stably expressing Fto-specific shRNA to increase m$^6$A levels, Hsp70 protein expression was significantly higher at both 4 and 6 h after heat shock (FIG. 10C). This effect was not due to increased levels of Hsp70 mRNA (FIG. 12B). Furthermore, knockdown of Fto caused a significant increase in the fraction of polysome-bound Hsp70 mRNA (FIG. 10D), suggesting that the increased levels of Hsp70 protein seen after heat shock reflect increased translation of Hsp70 mRNA in Fto knockdown cells.

Figure 10E:
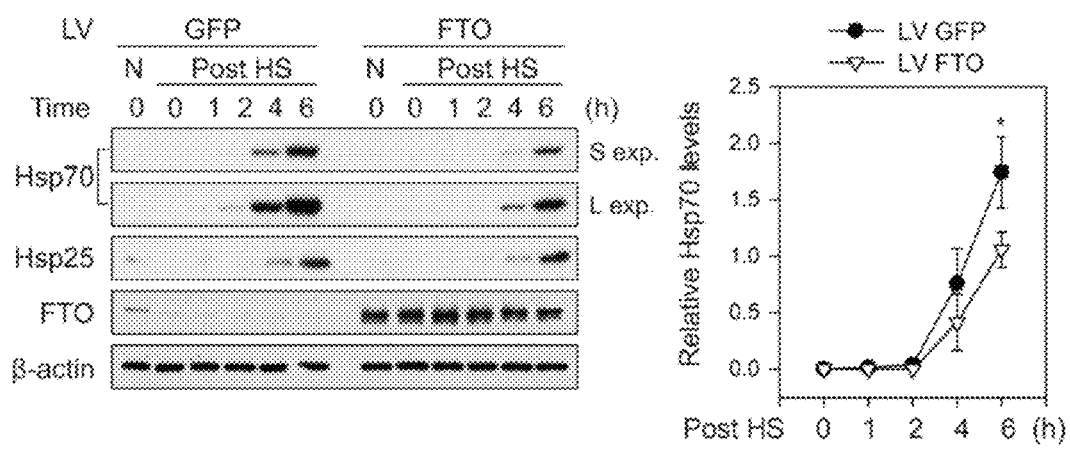
Figure 10F:
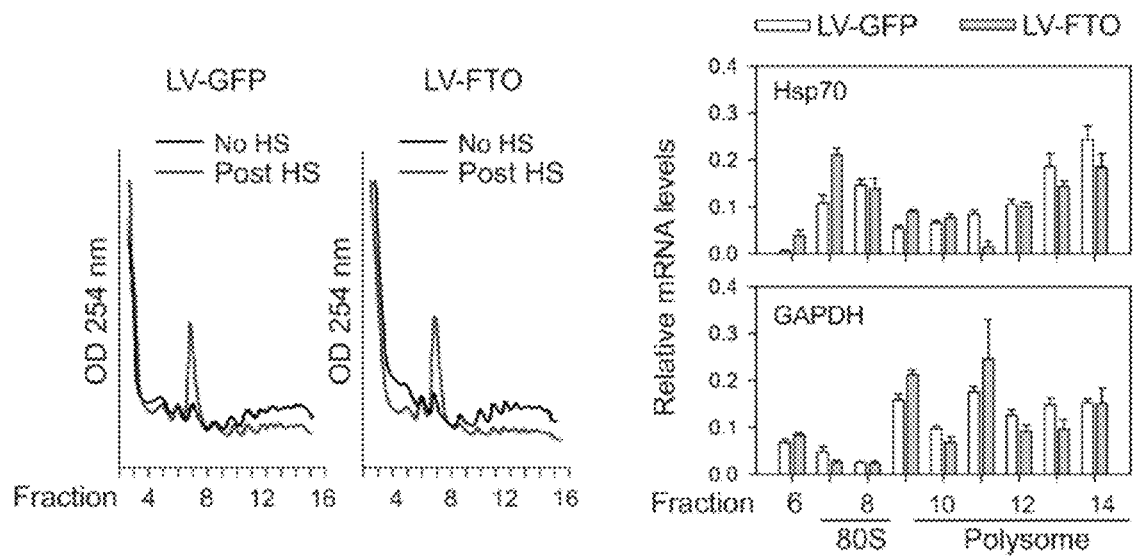
Figure 11A:
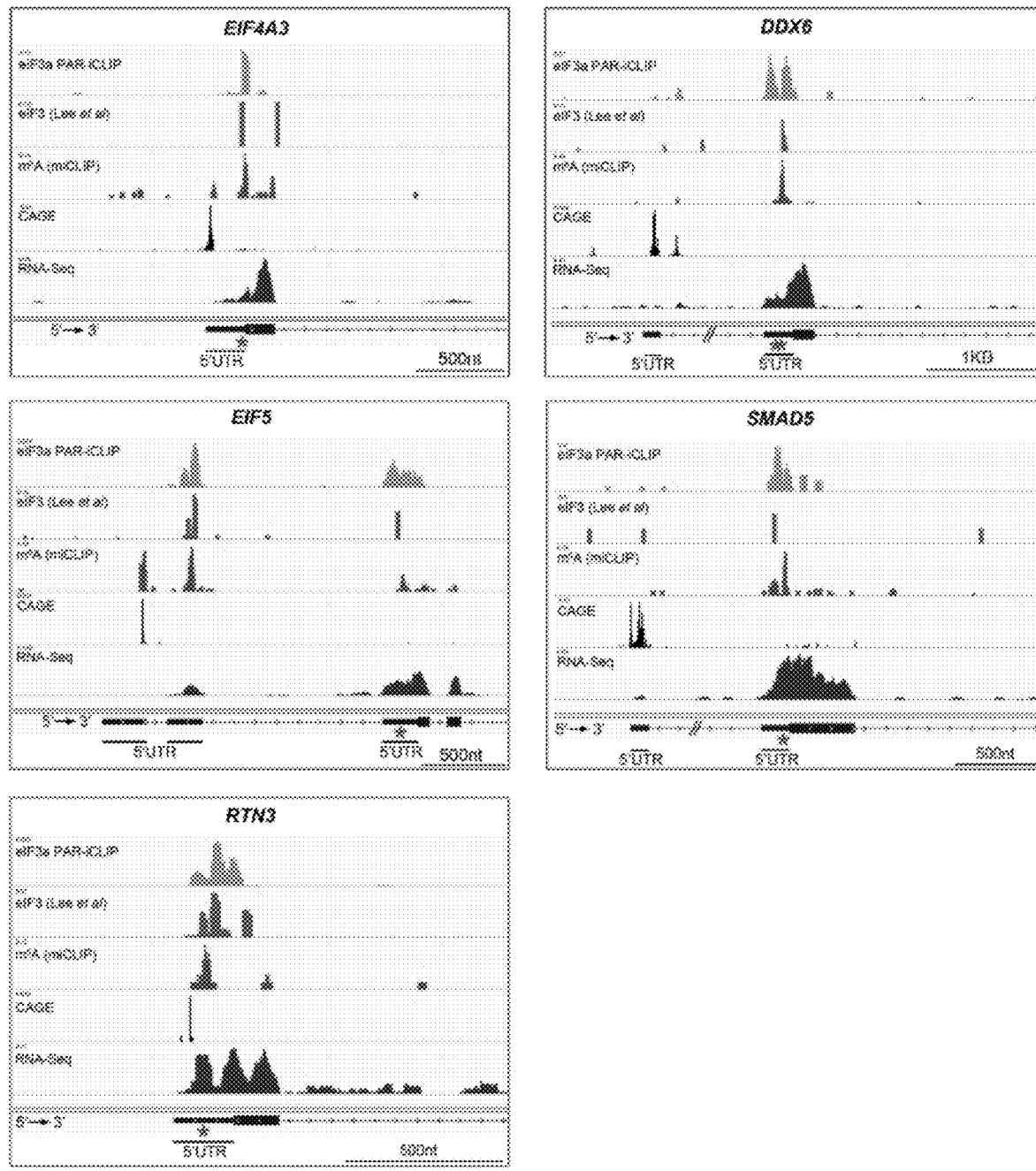
FIGS. 11A-11B demonstrate that $m^6A$ residues in cellular 5' UTRs are recognized by eIF3 and promote translation efficiency, related to FIGS. 9A-9B and FIGS. 10A-10F.
Figure 11B:
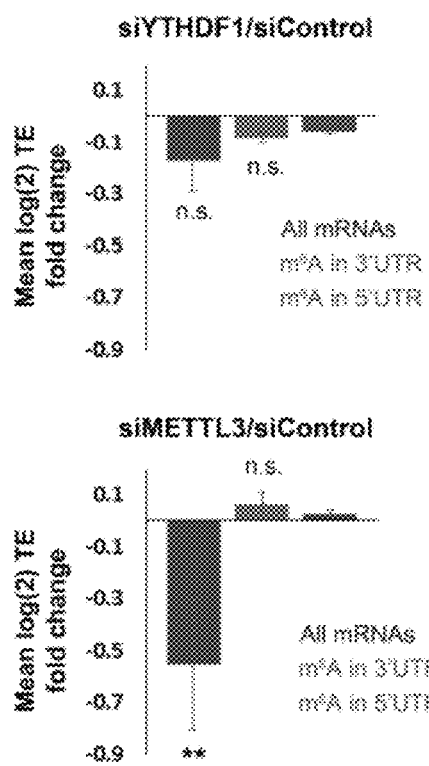

Consistent with the effects of Fto knockdown on Hsp70 levels, Fto overexpression caused significantly reduced Hsp70 protein production 4 and 6 hours after heat shock (FIG. 10E). This effect was not due to reduced Hsp70 transcript levels (FIG. 12B). In addition, Hsp70 mRNA was significantly reduced in the polysome fractions of Fto-overexpressing cells compared to GFP-expressing cells, confirming that the Fto-mediated reduction in Hsp70 protein levels was due to reduced Hsp70 translation (FIG. 10F). These data suggest that the loss of m$^6$A in Hsp70 mRNA results in reduced translation efficiency following heat shock.

Example 8

Transcriptome-Wide Redistribution of m$^6$A Following Cellular Stress

Figure 12C:
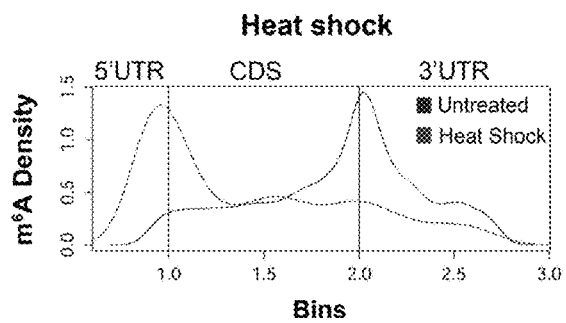

It was next sought to further understand the importance of 5' UTR m$^6$A residues in response to cellular stress. Based on findings with Hsp70 mRNA, the possibility that heat shock may alter the transcriptome-wide distribution of m$^6$A was considered. Under basal conditions, most m$^6$A residues are located in mRNAs near the stop codon, with markedly fewer m$^6$A residues in 5' UTRs. To determine if cellular stress alters the characteristic distribution of m$^6$A, cells were subjected to heat shock and mapped m$^6$A residues using miCLIP, a method for single-nucleotide resolution detection of m$^6$A sites (Linder et al., "Single-Nucleotide-Resolution Mapping of m$^6$A and m$^6$Am Throughout the Transcriptome," *Nat. Methods* 12(8):767-72 (2015), which is hereby incorporated by reference in its entirety). Remarkably, the metagene analysis showed a marked enrichment of m$^6$A in the 5' UTR in heat-shocked cells compared to control cells (FIG. 12C).

To further examine this phenomenon, existing transcriptome-wide m$^6$A mapping datasets that were performed in stressed cells and control cells were examined. These include HepG2 cells treated with UV, interferon-y, and heat shock (Dominissini et al., "Topology of the Human and Mouse m6A RNA Methylomes Revealed by m6A-Seq.," *Nature* 485:201-206 (2012), which is hereby incorporated by reference in its entirety). Metagene analyses showed prominent increases in the level of 5' UTR m$^6$A in both the UV-treated and heat shocked cells (FIG. 12D). Notably, the number of m$^6$A sites in the 3' UTR was relatively unaffected following heat shock or UV compared to control (n=4538, 4533, 3171, respectively), whereas the number of m$^6$A sites in the 5' UTR was markedly increased in heat shock and UV relative to control (n=1501, 1212, 326, respectively). Notably, interferon-y treatment did not alter the m$^6$A metagene profile (FIG. 12D), indicating that the induction of 5' UTR m$^6$A is not a nonspecific stress response, but instead is linked to specific forms of cellular stress.

Intriguingly, both heat shock and UV caused increased 5' UTR methylation in mRNAs that belong to common functional pathways, including phosphorylation and cell cycle regulation. Collectively, these results indicate that activation of some stress-response pathways causes a global reshaping of the cellular mRNA methylome and suggest that increased 5' UTR methylation may be a general component of the response to select cellular stresses.

Discussion of Examples 1-8

Eukaryotic mRNAs can be translated in both cap-dependent and cap-independent modes, although the mechanisms of translation initiation that do not require the 5' cap and eIF4E have been poorly understood. Examples 1-8 show that m$^6$A residues within the 5' UTR can act as an m$^6$A-induced ribosome engagement site, or MIRES, which promotes cap-independent translation of mRNA. A single m$^6$A in the 5' UTR of mRNAs is sufficient to promote MIRES activity in cell-free extracts, whereas m$^6$A residues outside the 5' UTR fail to show this effect. The significance of 5' UTR m⁶A residues is further seen in both ribosome profiling data sets and in individual cellular mRNAs in conditions where cap-dependent translation is suppressed. These results point to 5' UTR m⁶A as a mechanism for mRNAs to bypass the cap requirement for translation and suggest a potential role for this class of m⁶A residues in mediating translational responses induced in diverse cellular stress states.

A role for m⁶A in promoting translation initiation is supported by the finding that METTL3 depletion leads to a large reduction in translation efficiency of mRNAs containing 5' UTR m⁶A residues compared to mRNAs which contain m⁶As elsewhere. Although cap-independent translation of cellular mRNAs may also be mediated by m⁶A-independent pathways, including direct recruitment of ribosomes to internal 5' sequence or structural elements (Xue et al., "RNA Regulons in Hox 5' UTRs Confer Ribosome Specificity to Gene Regulation," *Nature* 517:33-38 (2015), which is hereby incorporated by reference in its entirety), these studies suggest that an eIF4E-independent mode of translation initiation can be switched on or off by reversible methylation of adenosine residues in the 5' UTR of mRNAs.

These studies show that cap-independent translation mediated by m⁶A requires a novel m⁶A reader, eIF3, and that many eIF3-binding sites in the transcriptome occur at m⁶A sites in 5' UTRs. The identification of eIF3 was originally suggested by the finding that the 48S complex can be assembled on m⁶A-containing RNA using only eIF1, eIF1A, eIF2, eIF3 and the 40S subunit. Of these components, eIF3 shows selective interaction with m⁶A both in vitro and in cells. By binding eIF3, 5' UTR m⁶A residues can stimulate translation initiation by directly recruiting the 43S preinitiation complex to the 5' UTR of mRNAs.

m⁶A has diverse effects on mRNAs, including mRNA destabilization and translational enhancement, although these effects are mediated by m⁶A near stop codons or in 3'UTRs (Wang et al., "N6-Methyladenosine-Dependent Regulation of Messenger RNA Stability," *Nature* 505:117-120 (2014a) and Wang et al., "N(6)-Methyladenosine Modulates Messenger RNA Translation Efficiency," *Cell* 161: 1388-1399 (2015), which are hereby incorporated by reference in their entirety). In the case of m⁶A near stop codons or in 3' UTRs, translational enhancement is mediated by YTHDF1, which binds to select transcripts at m⁶A sites in their 3' UTRs (Wang et al., "N(6)-Methyladenosine Modulates Messenger RNA Translation Efficiency," *Cell* 161:1388-1399 (2015), which is hereby incorporated by reference in its entirety). YTHDF1 binds numerous proteins, including eIF3 and other ribosome-associated proteins, which are proposed to be recruited to 3' UTRs to influence cap-dependent translation initiation (Wang et al., "N(6)-Methyladenosine Modulates Messenger RNA Translation Efficiency," *Cell* 161:1388-1399 (2015), which is hereby incorporated by reference in its entirety). This is in contrast to the mechanism of 5' UTR m⁶A, which directly recruits eIF3 and assembles translation initiation complexes in the 5' UTR without cap-binding proteins. Analysis of ribosome profiling data from YTHDF1-depleted cells further indicates that 5' UTR m⁶A residues promote translation through a YTHDF1-independent mechanism. Thus, m⁶A exhibits markedly distinct effects on mRNA based on its location in transcripts.

A long-standing question is the mechanism by which select cellular mRNAs undergo cap-independent translation during conditions where cap-dependent translation is suppressed (Holcik et al., "Translational Control in Stress and Apoptosis," *Nat. Rev. Mol. Cell. Biol.* 6:318-327 (2005), which is hereby incorporated by reference in its entirety). A prevailing hypothesis has been that these mRNAs contain cellular IRESs that promote cap-independent translation (Komar et al., "Cellular IRES-Mediated Translation: The War of ITAFs in Pathophysiological States," *Cell Cycle* 10:229-240 (2011), which is hereby incorporated by reference in its entirety). However, putative cellular IRESs often lack the complex structural elements seen in viral IRESs (Hellen et al., "Internal Ribosome Entry Sites in Eukaryotic mRNA Molecules," *Genes Dev.* 15:1593-1612 (2001), which is hereby incorporated by reference in its entirety). As a result of this discrepancy, and because of flaws inherent to many assays which test cellular IRES function, the evidence for and against cellular IRESs is a frequent topic of debate (Gilbert et al., "Alternative Ways to Think About Cellular Internal Ribosome Entry," *J. Biol. Chem.* 285:29033-29038 (2010), which is hereby incorporated by reference in its entirety). Given the prevalence of m⁶A within 5' UTRs, their translation-promoting activity represents an additional or perhaps alternative mechanism for mediating cap-independent translation.

The importance of 5' UTR m⁶A residues is supported by their selective upregulation in response to specific forms of stress. This m⁶A stress response points to the importance of this subset of m⁶A residues, which Examples 1-8 show are linked to cap-independent translation. Notably, other forms of stress regulate translation through the integrated stress response (Ron, "Translational Control in the Endoplasmic Reticulum Stress Response," *J. Clin. Invest.* 110:1383-1388 (2002), which is hereby incorporated by reference in its entirety). It will be important to determine if 5' UTR m⁶A-mediated translation is an alternative mechanism to orchestrate translational responses to stress.

Materials and Methods for Example 9

Cell Lines and Reagents

MEF cells tested negative for mycoplasma contamination. Cells were maintained in Dulbecco's Modified Eagle's Medium (DMEM) with 10% fetal bovine serum (FBS).

Construction of 5' UTR

The Fluc reporter with Hsp70 5' UTR has been reported previously (Sun et al., "P13K-mTORC1 Attenuates Stress Response by Inhibiting Cap-Independent Hsp70 Translation," *J. Biol. Chem.* 286:6791-6800 (2011), which is hereby incorporated by reference in its entirety). For Fluc reproters bearing other 5' UTRs, the following primers were used for 5' UTR cloning (Zhou et al., "Dynamic m6A mRNA Methylation Directs Translational Control of Heat Shock Response," *Nature* 526:591-594 (2015), which is hereby incorporated by reference in its entirety).

```
Hsc70 (HSPA8):
Forward:
                                    (SEQ ID NO: 55)
5'-CCCAAGCTTGGTCTCATTGAACGCGG-3'

Reverse:
                                    (SEQ ID NO: 56)
5'-CGGGATCCCCTTAGACATGGTTGCTT-3'

Tubulin (TUBG2):
Forward:
                                    (SEQ ID NO: 57)
5'-GGCAAGCTTTGCGCCTGTGCTGAATTCCAGCTGC-3'
```

-continued

Reverse:
(SEQ ID NO: 58)
5'-GGCGGATCCGCATCGCCGATCAGACCTAG-3'.

In Vitro Transcription

Plasmids containing the corresponding 5' UTR sequences of mouse HSPA1A and full-length firefly luciferase were used as templates. Transcripts with normal m$^7$G cap were generated using the mMessage mMachine T7 Ultra kit (Ambion) and transcripts with non-functional cap analogue GpppA were synthesized using MEGAscript T7 Transcription Kit (Ambion). To obtain mRNAs with the adenosine replaced with m$^6$A, in vitro transcription was conducted in a reaction in which 5% of the adenosine was replaced with N$^6$-Methyladenosine. All mRNA products were purified using the MEGAclear kit (Ambion) according to the manufacturer's instructions.

In Vitro Translation

In vitro translation was performed using the Rabbit Reticulocyte Lysate System (Promega) according to the manufacturer's instructions. Luciferase activity was measured using a luciferase reporter assay system (Promega) on a Synergy HT Multi-detection Microplate Reader (BioTek Instruments).

Real-Time Luciferase Assay

Cells grown in 35-mm dishes were transfected with in vitro-synthesized mRNA containing the luciferase gene. Luciferase substrate D-luciferin (1 mM, Regis Tech) was added into the culture medium immediately after transfection. Luciferase activity was monitored and recorded using Kronos Dio Luminometer (Atto).

RNA Splint Ligation

The ligation method was optimized from previous reports (Kershaw et al., "Splint Ligation of RNA with T4 DNA Ligase," *Methods Mol. Biol.* 941:257-269 (2012); Stark et al., "An RNA Ligase-Mediated Method for the Efficient Creation of Large, Synthetic RNAs," *RNA* 12:2014-2019 (2006); and Maroney et al., "Direct Detection of Small RNAs Using Splinted Ligation," *Nature Protocols* 3:279-287 (2008), which are hereby incorporated by reference in their entirety). The RNA oligonucleotide covering the 82-117 nucleotide region of HSPA1A was synthesized by Thermo Scientific, whereas RNA fragments corresponding to other regions were generated by in vitro transcription. For sequential splint ligation, two DNA bridging oligonucleotides were designed (Zhou et al., "Dynamic m$^6$A mRNA Methylation Directs Translational Control of Heat Shock Response," *Nature* 526:591-594 (2015), which is hereby incorporated by reference in its entirety):

18733639

DNA Bridge 1: 5'-GGTCCTGGCCGAGGATCGG-GAACGCGCCGCTCGCTC-3' (SEQ ID NO:59);

DNA Bridge 2: 5'-CTCCGCGGCAGG-GATGCTCTGGGGAAGGCTGGTCCT-3' (SEQ ID NO:60). For 3' RNA oligonucleotide (donor) phosphorylation, 1 µl of 10× PNK buffer, 6 µl of ATP (10 mM), 0.5 µl of RNasin (20 units) and 1 µl of T4 PNK (5 units). The reaction mixture was incubated at 37° C. for 30 minutes followed by inactivation of T4 PNK at 65° C. for 20 minutes. Next, the DNA bridge oligonucleotide was hybridized with the 3' RNA oligonucleotide and the 5' RNA oligonucleotide (acceptor) at a 1:1.5:2 ratio (5' RNA bridge:3' RNA). Oligonucleotides were annealed (95° C. for 1 minute followed by 65° C. for 2 minutes and 37° C. for 10 minutes) in the presence of 1× T4 DNA dilution buffer. To ligate the 5' and 3' RNA together, T4 DNA ligase and the T4 DNA ligation buffer were added and the reaction mixture was incubated at 37° C. for 1 hour. The ligation was stopped by adding 1 µl of 0.5 M EDTA followed by phenol-chloroform extraction and ethanol precipitation. Ligation products were analyzed by 10% TBE-Urea gels or formaldehyde gels. The expected RNA ligation products in TBE-Urea gels were eluted in RNA gel elution buffer (300 mM NaOAc pH 5.5, 1 mM EDTA, and 0.1 U µµl$^{-1}$ SUPERase In) followed by ethanol precipitation. The final products in formaldehyde gels were isolated by Zymoclean Gel RNA Recovery Kit (Zymo Research).

Example 9

Selective 5' UTR m6A Modification Mediates Cap-independent Translation

It is commonly believed that the 5' UTR of Hsp70 mRNA recruits the translational machinery via an internal ribosome entry site (IRES) (McGarry et al., "The Preferential Translation of Drosophila Hsp70 mRNA Requires Sequence in the Untranslated Leader," *Cell* 42:903-911 (1985); Klemenz et al., "Selective Translation of Heat Shock mRNA in *Drosophila melanogaster* Depends on Sequence Information in the Leader," *EMBO J.* 4:2053-2060 (1985); Rubsova et al., "Distinctive Properties of the 5'-Untranslated Region of human Hsp70 mRNA," *J. Biol. Chem.* 278:22350-22356 (2003); and Sun et al., "P13K-mTORC1 Attenuates Stress Response by Inhibiting Cap-Independent Hsp70 Translation," *J. Biol. Chem.* 286:6791-6800 (2011), which are hereby incorporated by reference in their entirety). However, conflicting results exist and the exact cap-independent translation-promoting determinants remain elusive (Sun et al., "P13K-mTORC1 Attenuates Stress Response by Inhibiting Cap-Independent Hsp70 Translation," *J. Biol. Chem.* 286:6791-6800 (2011) and Zhang et al., "Translational Control of the Cytosolic Stress Response by Mitochondrial Ribosomal Protein L18," *Nature Struct. Mol. Biol.* 22:404-410 (2015), which are hereby incorporated by reference in their entirety). Given the fact that the normal 5' end cap structure is a methylated purine (N$^7$-methylguanosine, m$^7$G), it was hypothesized that the stress-induced m$^6$A in the 5' UTR enables selective translation by acting as a functional cap substitute. To test this hypothesis, a firefly luciferase (Fluc) reporter assay was performed in MEF cells by transfecting mRNAs synthesized in the absence or presence of m$^6$A (FIG. 13A). For the messenger without 5' UTR, random incorporation of m$^6$A slightly reduced the Fluc activity after mRNA transfection. In the presence of 5' UTR from Hsp70, but not tubulin, the incorporation of m$^6$A markedly increased the Fluc activity in transfected MEF cells. Notably, m$^6$A incorporation does not affect the stability of the synthesized mRNAs in transfected cells (FIG. 14A). Next, the 5' end m$^7$G cap was replaced with a non-functional cap analogue ApppG. As expected, the resultant mRNA did not support translation in the absence of 5' UTR or in the presence of tubulin 5' UTR (FIGS. 13A and 14B). Only when the Hsp70 5' UTR was present, was the translating-promoting feature clearly manifested after m$^6$A incorporation, in particular under stress conditions (FIG. 13A). This effect is specific to m$^6$A modification but not m$^6$Am because ribose methylation in the form of 2'-O-MeA suppressed translation of the Fluc reporter bearing Hsp70 5' UTR (FIG. 13A). Therefore, methylation of Hsp70 5' UTR in the form of m$^6$A promotes cap-independent translation.

Figure 15A:
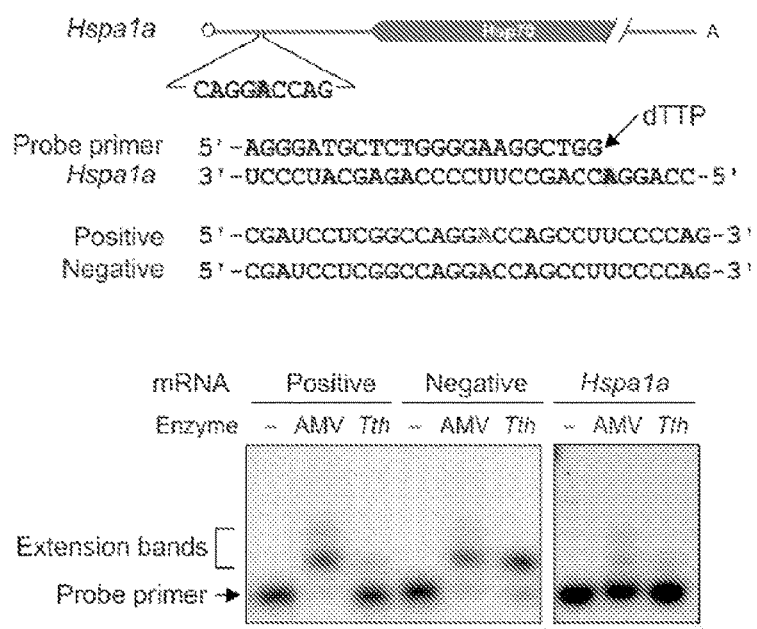
FIGS. 15A-15B show the site-specific detection of m⁶A modification on HSPA1A.
Figure 15B:
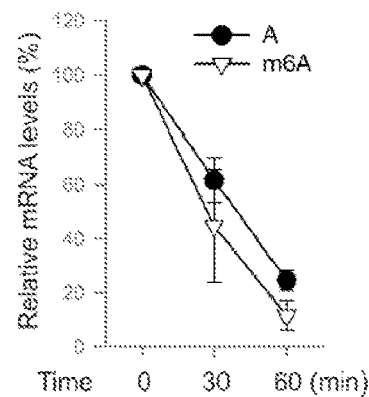

The 5' UTR contains multiple A's, although not all of them are methylated. On the basis of the predicted m$^6$A sequence motif, the A residue at the 103 position of Hsp70 mRNA is likely to be methylated. Using a single-nucleotide m⁶A detection method (Harcourt et al., "Identification of a Selective Polymerase Enables Detection of N⁶-Methyladenosine in RNA," *J. Am. Chem. Soc.* 135:19079-19082 (2013), which is hereby incorporated by reference in its entirety), it was confirmed that the methylation event at this position upon heat shock stress (FIG. 15A). To demonstrate the significance of methylation at this single site, an A103C mutation was introduced into the Hsp70 5' UTR. Remarkably, m⁶A incorporation no longer promoted translation of the Fluc reporter in transfected cells (FIG. 13B). To directly demonstrate the importance of this single m⁶A site without changing the nucleotide, a sequential RNA splint ligation strategy was employed to construct a Fluc reporter bearing Hsp70 5' UTR with or without A103 methylation (FIG. 13C) (Kershaw et al., "Splint Ligation of RNA with T4 DNA Ligase," *Methods Mol. Biol.* 941:257-269 (2012) and Stark et al., "An RNA Ligase-Mediated Method for the Efficient Creation of Large, Synthetic RNAs," *RNA* 12:2014-2019 (2006), which are hereby incorporated by reference in their entirety). Using an in vitro translation system, the Fluc reporter containing the single m⁶A at the 103 position showed about 50% increase in translation efficiency in comparison to the one with normal A (FIG. 13C). Notably, both messages showed comparable turnover during the entire course of in vitro translation (FIG. 15B). Collectively, these results firmly established a crucial role of 5' UTR m⁶A modification in non-canonical translation initiation.

Discussion of Example 9

Much of the current understanding of cap-independent translation is limited to the IRES mechanism (Pelletier et al., "Internal Initiation of Translation of Eukaryotic mRNA Directed by a Sequence Derived from Poliovirus RNA," *Nature* 334:320-325 (1988) and Hellen et al., "Internal Ribosome Entry Sites in Eukaryotic mRNA Molecules," *Genes Dev.* 15:1593-1612 (2011), which are hereby incorporated by reference in their entirety). However, beyond a few examples, many cellular genes capable of cap-independent translation do not seem to contain any IRES elements. The results presented here demonstrate a surprising role of m⁶A in mediating mRNA translation initiation independent of the normal m⁷G cap.

In contrast to the wide belief that m⁶A modification is static on mRNAs, it was found that 5' UTR methylation in the form of m⁶A is dynamic. Methylation often serves as a mark to distinguish self and foreign DNAs or parental and daughter DNA strands (Kunkel et al., "DNA Mismatch Repair," *Annu. Rev. Biochem.* 74:681-710 (2005), which is hereby incorporated by reference in its entirety). The stress-inducible mRNA 5' UTR methylation permits ribosomes to distinguish nascent transcripts from pre-existing messages, thereby achieving selective mRNA translation (FIG. 13D). The mechanistic connection between 5' UTR methylation and cap-independent translation solves the central puzzle how selective translation is achieved when global translation is suppressed in responding to stress.

What is claimed:

1. An mRNA molecule comprising:
   a heterologous 5' untranslated region (UTR), wherein the 5' untranslated region comprises an adenosine methylation motif, wherein the adenosine methylation motif is a nucleotide sequence DRACH, wherein D is A, G, or U; R is G or A; and H is A, C, or U;
   a modified residue in the adenosine methylation motif of the 5' untranslated region (UTR), wherein the modified residue is a methylated adenosine residue; and
   a 5' cap, wherein said mRNA molecule is a substrate of eIF4E-independent translation.

2. The mRNA molecule according to claim 1 further comprising:
   an internal ribosome entry site ("IRES") motif.

3. The mRNA molecule according to claim 1, wherein the mRNA molecule encodes for a full-length protein.

4. The mRNA molecule according to claim 1, wherein the 5' cap is heterologous to the mRNA molecule.

5. The mRNA molecule according to claim 1, comprising more than one methylated adenosine residue in the 5' untranslated region (UTR).

6. The mRNA molecule according to claim 1, wherein the methylated adenosine residue is $N^6$-methyladenosine ($m^6A$).

7. The mRNA molecule according to claim 1, wherein the RNA molecule comprises a single adenosine methylation motif.

8. The mRNA molecule according to claim 1, wherein the RNA molecule comprises multiple adenosine methylation motifs.

9. The mRNA molecule according to claim 1, wherein the RNA molecule comprises two adenosine methylation motifs.

10. The mRNA molecule according to claim 1, wherein the RNA molecule comprises three adenosine methylation motifs.

11. The mRNA molecule according to claim 1, wherein the RNA molecule comprises four adenosine methylation motifs.

12. The mRNA molecule according to claim 1, wherein the RNA molecule comprises five adenosine methylation motifs.

13. The mRNA molecule according to claim 1, wherein the RNA molecule comprises six adenosine methylation motifs.

14. The mRNA molecule according to claim 1, wherein the RNA molecule comprises seven adenosine methylation motifs.

15. The mRNA molecule according to claim 1, wherein the RNA molecule encodes a therapeutic protein or peptide sequence.

16. The mRNA molecule according to claim 1, wherein the therapeutic protein is down-regulated in a disease state, a stress state, or during a pathogen infection of a cell.

* * * * *

SEQUENCE LISTING

```
<160> NUMBER OF SEQ ID NOS: 60

<210> SEQ ID NO 1
<211> LENGTH: 54
<212> TYPE: RNA
<213> ORGANISM: Artificial
<220> FEATURE:
<223> OTHER INFORMATION: B-globin 5' UTR

<400> SEQUENCE: 1
gacacuugcu uuugacacaa cuguguuuac uugcaauccc ccaaaacaga caga         54

<210> SEQ ID NO 2
<211> LENGTH: 49
<212> TYPE: RNA
<213> ORGANISM: Artificial
<220> FEATURE:
<223> OTHER INFORMATION: B-globin 1 A mid 5' UTR

<400> SEQUENCE: 2
ggcucuugcu uuugccucuu cugugugacu ugccuucccc cuugucugc               49

<210> SEQ ID NO 3
<211> LENGTH: 49
<212> TYPE: RNA
<213> ORGANISM: Artificial
<220> FEATURE:
<223> OTHER INFORMATION: B-globin 3 As 5' UTR

<400> SEQUENCE: 3
gacucuugcu uuugccucuu cuguguugcu ugacuucccc cuuguugac               49

<210> SEQ ID NO 4
<211> LENGTH: 49
<212> TYPE: RNA
```

```
<213> ORGANISM: Artificial
<220> FEATURE:
<223> OTHER INFORMATION: B-globin 0 As 5' UTR

<400> SEQUENCE: 4
ggcucuugcu uuugccucuu cuguguugcu ugccuucccc cuugucugc        49

<210> SEQ ID NO 5
<211> LENGTH: 49
<212> TYPE: RNA
<213> ORGANISM: Artificial
<220> FEATURE:
<223> OTHER INFORMATION: B-globin 1 A 5' end 5' UTR

<400> SEQUENCE: 5
gacucuugcu uuugccucuu cuguguugcu ugccuucccc cuugucugc        49

<210> SEQ ID NO 6
<211> LENGTH: 49
<212> TYPE: RNA
<213> ORGANISM: Artificial
<220> FEATURE:
<223> OTHER INFORMATION: B-globin 1 A 3' end 5' UTR

<400> SEQUENCE: 6
ggcucuugcu uuugccucuu cuguguugcu ugccuucccc cuuguugac        49

<210> SEQ ID NO 7
<211> LENGTH: 42
<212> TYPE: RNA
<213> ORGANISM: Artificial
<220> FEATURE:
<223> OTHER INFORMATION: HIST2H2BE 5' UTR

<400> SEQUENCE: 7
acuucuuuuc uuggcuaagc cgcguuugua cugugucuua cc               42

<210> SEQ ID NO 8
<211> LENGTH: 49
<212> TYPE: RNA
<213> ORGANISM: Artificial
<220> FEATURE:
<223> OTHER INFORMATION: pGL4.34 vector 5' UTR

<400> SEQUENCE: 8
ggaagcucga cuuccagcuu ggcaauccgg uacuguuggu aaagccacc        49

<210> SEQ ID NO 9
<211> LENGTH: 82
<212> TYPE: RNA
<213> ORGANISM: Artificial
<220> FEATURE:
<223> OTHER INFORMATION: B-globin Hairpin 5' UTR

<400> SEQUENCE: 9
gggccccgcc cggugucggg cggggcccga cacugcuuu ugacacaacu guguuuacuu    60 gcaaucccccc aaaacagaca ga                                   82

<210> SEQ ID NO 10
<211> LENGTH: 29
<212> TYPE: RNA
<213> ORGANISM: Artificial
<220> FEATURE:
<223> OTHER INFORMATION: HSPA1A template

<400> SEQUENCE: 10
```

```
ucccuacgag accccuuccg accaggacc                                           29

<210> SEQ ID NO 11
<211> LENGTH: 23
<212> TYPE: DNA
<213> ORGANISM: Artificial
<220> FEATURE:
<223> OTHER INFORMATION: Primer

<400> SEQUENCE: 11
agggatgctc tggggaaggc tgg                                                 23

<210> SEQ ID NO 12
<211> LENGTH: 30
<212> TYPE: RNA
<213> ORGANISM: Artificial
<220> FEATURE:
<223> OTHER INFORMATION: Positive control

<400> SEQUENCE: 12
cgauccucgg ccaggaccag ccuuccccag                                          30

<210> SEQ ID NO 13
<211> LENGTH: 30
<212> TYPE: RNA
<213> ORGANISM: Artificial
<220> FEATURE:
<223> OTHER INFORMATION: Negative control

<400> SEQUENCE: 13
cgauccucgg ccaggaccag ccuuccccag                                          30

<210> SEQ ID NO 14
<211> LENGTH: 22
<212> TYPE: DNA
<213> ORGANISM: Artificial
<220> FEATURE:
<223> OTHER INFORMATION: Gapdh Forward primer

<400> SEQUENCE: 14
caaggagtaa gaaaccctgg ac                                                  22

<210> SEQ ID NO 15
<211> LENGTH: 22
<212> TYPE: DNA
<213> ORGANISM: Artificial
<220> FEATURE:
<223> OTHER INFORMATION: Gapdh Reverse primer

<400> SEQUENCE: 15
ggatggaaat tgtgagggag at                                                  22

<210> SEQ ID NO 16
<211> LENGTH: 20
<212> TYPE: DNA
<213> ORGANISM: Artificial
<220> FEATURE:
<223> OTHER INFORMATION: Hsp70 Forward primer

<400> SEQUENCE: 16
tggtgcagtc cgacatgaag                                                     20

<210> SEQ ID NO 17
<211> LENGTH: 22
<212> TYPE: DNA
```

<213> ORGANISM: Artificial
<220> FEATURE:
<223> OTHER INFORMATION: Hsp70 Reverse primer

<400> SEQUENCE: 17
gctgagagtc gttgaagtag gc                                    22

<210> SEQ ID NO 18
<211> LENGTH: 20
<212> TYPE: DNA
<213> ORGANISM: Artificial
<220> FEATURE:
<223> OTHER INFORMATION: Fluc Forward primer

<400> SEQUENCE: 18
atccggaagc gaccaacgcc                                       20

<210> SEQ ID NO 19
<211> LENGTH: 20
<212> TYPE: DNA
<213> ORGANISM: Artificial
<220> FEATURE:
<223> OTHER INFORMATION: Fluc Reverse primer

<400> SEQUENCE: 19
gtcgggaaga cctgccacgc                                       20

<210> SEQ ID NO 20
<211> LENGTH: 20
<212> TYPE: DNA
<213> ORGANISM: Artificial
<220> FEATURE:
<223> OTHER INFORMATION: pGL4.34 Luc Forward primer

<400> SEQUENCE: 20
ttcgtgagca agaaagggct                                       20

<210> SEQ ID NO 21
<211> LENGTH: 20
<212> TYPE: DNA
<213> ORGANISM: Artificial
<220> FEATURE:
<223> OTHER INFORMATION: pGL4.34 Luc Reverse primer

<400> SEQUENCE: 21
agtcgtactc gttgaagccg                                       20

<210> SEQ ID NO 22
<211> LENGTH: 20
<212> TYPE: DNA
<213> ORGANISM: Artificial
<220> FEATURE:
<223> OTHER INFORMATION: GAPDH Forward primer

<400> SEQUENCE: 22
aaatcaagtg gggcgatgct                                       20

<210> SEQ ID NO 23
<211> LENGTH: 20
<212> TYPE: DNA
<213> ORGANISM: Artificial
<220> FEATURE:
<223> OTHER INFORMATION: GAPDH Reverse primer

<400> SEQUENCE: 23
caaatgagcc ccagccttct                                       20

<210> SEQ ID NO 24
<211> LENGTH: 21
<212> TYPE: DNA
<213> ORGANISM: Artificial
<220> FEATURE:
<223> OTHER INFORMATION: SETD1A Forward primer

<400> SEQUENCE: 24
agcgggctat tctctcactt g                                    21

<210> SEQ ID NO 25
<211> LENGTH: 20
<212> TYPE: DNA
<213> ORGANISM: Artificial
<220> FEATURE:
<223> OTHER INFORMATION: SETD1A Reverse primer

<400> SEQUENCE: 25
gctttgcttc tcttccccgt                                      20

<210> SEQ ID NO 26
<211> LENGTH: 20
<212> TYPE: DNA
<213> ORGANISM: Artificial
<220> FEATURE:
<223> OTHER INFORMATION: ITPRIPL2 Forward primer

<400> SEQUENCE: 26
aacacttgag ctgggagagg                                      20

<210> SEQ ID NO 27
<211> LENGTH: 21
<212> TYPE: DNA
<213> ORGANISM: Artificial
<220> FEATURE:
<223> OTHER INFORMATION: ITPRIPL2 Reverse primer

<400> SEQUENCE: 27
gaagacgcgt agattgaggg t                                    21

<210> SEQ ID NO 28
<211> LENGTH: 20
<212> TYPE: DNA
<213> ORGANISM: Artificial
<220> FEATURE:
<223> OTHER INFORMATION: PNMA1 Forward primer

<400> SEQUENCE: 28
ctggctagtc tcccaaacgg                                      20

<210> SEQ ID NO 29
<211> LENGTH: 20
<212> TYPE: DNA
<213> ORGANISM: Artificial
<220> FEATURE:
<223> OTHER INFORMATION: PNMA1 Reverse primer

<400> SEQUENCE: 29
catcttgcgt ctgggtctgg                                      20

<210> SEQ ID NO 30
<211> LENGTH: 18
<212> TYPE: DNA
<213> ORGANISM: Artificial
<220> FEATURE:

<223> OTHER INFORMATION: BMP6 Forward primer

<400> SEQUENCE: 30
gagggccagg aagggggaa                                                18

<210> SEQ ID NO 31
<211> LENGTH: 15
<212> TYPE: DNA
<213> ORGANISM: Artificial
<220> FEATURE:
<223> OTHER INFORMATION: BMP6 Reverse primer

<400> SEQUENCE: 31
cgtggagcgg cggag                                                    15

<210> SEQ ID NO 32
<211> LENGTH: 18
<212> TYPE: DNA
<213> ORGANISM: Artificial
<220> FEATURE:
<223> OTHER INFORMATION: T7 phi 2.5 promoter sequence

<400> SEQUENCE: 32
taatacgact cactatta                                                 18

<210> SEQ ID NO 33
<211> LENGTH: 49
<212> TYPE: RNA
<213> ORGANISM: Artificial
<220> FEATURE:
<223> OTHER INFORMATION: pGL4.34 5' UTR

<400> SEQUENCE: 33
ggaagcucga cuuccagcuu ggcaauccgg uacuguuggu aaagccacc                49

<210> SEQ ID NO 34
<211> LENGTH: 54
<212> TYPE: RNA
<213> ORGANISM: Artificial
<220> FEATURE:
<223> OTHER INFORMATION: Beta-globin

<400> SEQUENCE: 34
gacacuugcu uuugacacaa cuguguuuac uugcaauccc ccaaaacaga caga          54

<210> SEQ ID NO 35
<211> LENGTH: 49
<212> TYPE: RNA
<213> ORGANISM: Artificial
<220> FEATURE:
<223> OTHER INFORMATION: Beta-globin 3 As

<400> SEQUENCE: 35
gacucuugcu uuugccucuu cuguguugcu ugacuucccc cuuguugac                49

<210> SEQ ID NO 36
<211> LENGTH: 49
<212> TYPE: RNA
<213> ORGANISM: Artificial
<220> FEATURE:
<223> OTHER INFORMATION: Beta-globin 1 A 5' end

<400> SEQUENCE: 36
gacucuugcu uuugccucuu cuguguugcu ugccuucccc cuugucugc                49

```
<210> SEQ ID NO 37
<211> LENGTH: 49
<212> TYPE: RNA
<213> ORGANISM: Artificial
<220> FEATURE:
<223> OTHER INFORMATION: Beta-globin 1 A mid

<400> SEQUENCE: 37
ggcucuugcu uuugccucuu cuguguagacu ugccuucccc cuugucugc          49

<210> SEQ ID NO 38
<211> LENGTH: 49
<212> TYPE: RNA
<213> ORGANISM: Artificial
<220> FEATURE:
<223> OTHER INFORMATION: Beta-globin 1 A 3' end

<400> SEQUENCE: 38
ggcucuugcu uuugccucuu cuguguugcu ugccuucccc cuuguugac          49

<210> SEQ ID NO 39
<211> LENGTH: 49
<212> TYPE: RNA
<213> ORGANISM: Artificial
<220> FEATURE:
<223> OTHER INFORMATION: Beta-globin 0 As

<400> SEQUENCE: 39
ggcucuugcu uuugccucuu cuguguugcu ugccuucccc cuugucugc          49

<210> SEQ ID NO 40
<211> LENGTH: 42
<212> TYPE: RNA
<213> ORGANISM: Artificial
<220> FEATURE:
<223> OTHER INFORMATION: HIST2H2BE

<400> SEQUENCE: 40
acuucuuuuc uuggcuaagc cgcguuugua cugugucuua cc                 42

<210> SEQ ID NO 41
<211> LENGTH: 82
<212> TYPE: RNA
<213> ORGANISM: Artificial
<220> FEATURE:
<223> OTHER INFORMATION: Beta-globin hairpin

<400> SEQUENCE: 41
gggccccgcc cggugucggg cggggcccga cacugcuuu ugacacaacu guguuuacuu    60 gcaaucccccc aaaacagaca ga                                          82

<210> SEQ ID NO 42
<211> LENGTH: 49
<212> TYPE: RNA
<213> ORGANISM: Artificial
<220> FEATURE:
<223> OTHER INFORMATION: Beta-globin 1 A mid UAC

<400> SEQUENCE: 42
ggcucuugcu uuugccucuu cuguguuacu ugccuucccc cuugucugc          49

<210> SEQ ID NO 43
<211> LENGTH: 49
<212> TYPE: RNA
<213> ORGANISM: Artificial
<220> FEATURE:
```

```
<223> OTHER INFORMATION: Beta-globin 1 A mid CAG

<400> SEQUENCE: 43
ggcucuugcu uuugccucuu cugugucagu ugccuucccc cuugucugc            49

<210> SEQ ID NO 44
<211> LENGTH: 92
<212> TYPE: RNA
<213> ORGANISM: Artificial
<220> FEATURE:
<223> OTHER INFORMATION: Beta-globin 2 AUG

<400> SEQUENCE: 44
gacacuugcu uuagaauugg acaacugugu uuacuugcaa uccccaaaa cagacugcau  60 cguccagug aggagaaguc ugcggagaau gg                               92

<210> SEQ ID NO 45
<211> LENGTH: 55
<212> TYPE: RNA
<213> ORGANISM: Artificial
<220> FEATURE:
<223> OTHER INFORMATION: Beta-globin

<400> SEQUENCE: 45
ggacacuugc uuuugacaca acuguguuua cuugcaaucc cccaaaacag acaga       55

<210> SEQ ID NO 46
<211> LENGTH: 23
<212> TYPE: DNA
<213> ORGANISM: Artificial
<220> FEATURE:
<223> OTHER INFORMATION: biotin-labeled probe

<400> SEQUENCE: 46
ttcataacat atctctgtct ctt                                         23

<210> SEQ ID NO 47
<211> LENGTH: 21
<212> TYPE: DNA
<213> ORGANISM: Artificial
<220> FEATURE:
<223> OTHER INFORMATION: Fto target sequence

<400> SEQUENCE: 47
gctgaggcag ttctggtttc a                                           21

<210> SEQ ID NO 48
<211> LENGTH: 21
<212> TYPE: DNA
<213> ORGANISM: Artificial
<220> FEATURE:
<223> OTHER INFORMATION: scramble control

<400> SEQUENCE: 48
cctaaggtta agtcgccctc g                                           21

<210> SEQ ID NO 49
<211> LENGTH: 84
<212> TYPE: RNA
<213> ORGANISM: Artificial
<220> FEATURE:
<223> OTHER INFORMATION: probe

<400> SEQUENCE: 49
gggacuggga cugggacugg gacugggacu gggacuggga cugggacugg gacugggacu  60
```

-continued

```
gggacugggga cugggacugg gacu                                          84

<210> SEQ ID NO 50
<211> LENGTH: 84
<212> TYPE: RNA
<213> ORGANISM: Artificial
<220> FEATURE:
<223> OTHER INFORMATION: probe

<400> SEQUENCE: 50
gguacuggua cugguacugg uacugguacu gguacuggua cugguacugg uacugguacu    60
gguacuggua cugguacugg uacu                                          84

<210> SEQ ID NO 51
<211> LENGTH: 90
<212> TYPE: RNA
<213> ORGANISM: Artificial
<220> FEATURE:
<223> OTHER INFORMATION: probe

<400> SEQUENCE: 51
ggcaguggca guggcagugg caguggcagu ggcaguggca guggcagugg caguggcagu    60
ggcaguggca guggcagugg caguggcagu                                    90

<210> SEQ ID NO 52
<211> LENGTH: 78
<212> TYPE: RNA
<213> ORGANISM: Artificial
<220> FEATURE:
<223> OTHER INFORMATION: probe

<400> SEQUENCE: 52
gggacuggga cugggacugg gacugggacu gggacuggga cugggacugg gacugggacu    60
gggacuggga cugggacu                                                 78

<210> SEQ ID NO 53
<211> LENGTH: 45
<212> TYPE: RNA
<213> ORGANISM: Artificial
<220> FEATURE:
<223> OTHER INFORMATION: probe

<400> SEQUENCE: 53
gugugugugu ggacuggacu ggacuggacu ggacuggacu ggacu                   45

<210> SEQ ID NO 54
<211> LENGTH: 84
<212> TYPE: RNA
<213> ORGANISM: Artificial
<220> FEATURE:
<223> OTHER INFORMATION: m6A RNA probe

<400> SEQUENCE: 54
gggacuggga cugggacugg gacugggacu gggacuggga cugggacugg gacugggacu    60
gggacuggga cugggacugg gacu                                          84

<210> SEQ ID NO 55
<211> LENGTH: 26
<212> TYPE: DNA
<213> ORGANISM: Artificial
<220> FEATURE:
<223> OTHER INFORMATION: Hsc70 Forward primer
```

```
<400> SEQUENCE: 55
cccaagcttg gtctcattga acgcgg                                      26

<210> SEQ ID NO 56
<211> LENGTH: 26
<212> TYPE: DNA
<213> ORGANISM: Artificial
<220> FEATURE:
<223> OTHER INFORMATION: Hsc70 Reverse primer

<400> SEQUENCE: 56
cgggatcccc ttagacatgg ttgctt                                      26

<210> SEQ ID NO 57
<211> LENGTH: 34
<212> TYPE: DNA
<213> ORGANISM: Artificial
<220> FEATURE:
<223> OTHER INFORMATION: Tubulin Forward primer

<400> SEQUENCE: 57
ggcaagcttt gcgcctgtgc tgaattccag ctgc                             34

<210> SEQ ID NO 58
<211> LENGTH: 29
<212> TYPE: DNA
<213> ORGANISM: Artificial
<220> FEATURE:
<223> OTHER INFORMATION: Tubulin Reverse primer

<400> SEQUENCE: 58
ggcggatccg catcgccgat cagacctag                                   29

<210> SEQ ID NO 59
<211> LENGTH: 36
<212> TYPE: DNA
<213> ORGANISM: Artificial
<220> FEATURE:
<223> OTHER INFORMATION: DNA Bridge 1

<400> SEQUENCE: 59
ggtcctggcc gaggatcggg aacgcgccgc tcgctc                           36

<210> SEQ ID NO 60
<211> LENGTH: 36
<212> TYPE: DNA
<213> ORGANISM: Artificial
<220> FEATURE:
<223> OTHER INFORMATION: DNA Bridge 2

<400> SEQUENCE: 60
ctccgcggca gggatgctct ggggaaggct ggtcct                           36
```